(12) United States Patent
Dashper et al.

(10) Patent No.: US 8,911,745 B2
(45) Date of Patent: Dec. 16, 2014

(54) IMMUNOLOGY TREATMENT FOR BIOFILMS

(71) Applicant: Oral Health Australia Pty Ltd, Carlton (AU)

(72) Inventors: Stuart Geoffrey Dashper, Carlton (AU); Eric Charles Reynolds, Carlton (AU); Paul David Veith, Carlton (AU); Ching Seng Ang, Preston (AU)

(73) Assignee: Oral Health Australia Pty Ltd., Carlton, Victoria (AU)

( * ) Notice: Subject to any disclaimer, the term of this patent is extended or adjusted under 35 U.S.C. 154(b) by 0 days.

(21) Appl. No.: 13/623,442

(22) Filed: Sep. 20, 2012

(65) Prior Publication Data

US 2013/0202641 A1     Aug. 8, 2013

Related U.S. Application Data

(62) Division of application No. 12/668,407, filed as application No. PCT/AU2008/001018 on Jul. 11, 2008, now abandoned.

(30) Foreign Application Priority Data

Jul. 12, 2007 (AU) .............................. 2007903787

(51) Int. Cl.
*A61K 39/02* (2006.01)
*C07K 14/195* (2006.01)

(52) U.S. Cl.
CPC ........... *A61K 39/0208* (2013.01); *C07K 14/195* (2013.01); *A61K 39/02* (2013.01)
USPC ...................... 424/190.1; 424/234.1; 530/350

(58) Field of Classification Search
CPC combination set(s) only.
See application file for complete search history.

(56) References Cited

U.S. PATENT DOCUMENTS

| | | | |
|---|---|---|---|
| 4,603,112 A | 7/1986 | Paoletti et al. | |
| 4,735,801 A | 4/1988 | Stocker | |
| 4,837,151 A | 6/1989 | Stocker | |
| 5,210,035 A | 5/1993 | Stocker | |
| 5,475,097 A | 12/1995 | Travis et al. | |
| 5,523,390 A | 6/1996 | Travis et al. | |
| 5,707,620 A | 1/1998 | Travis et al. | |
| 5,711,937 A | 1/1998 | Nishida et al. | |
| 6,129,917 A | 10/2000 | Potempa et al. | |
| 6,274,718 B1 | 8/2001 | Travis et al. | |
| 6,444,799 B1 | 9/2002 | Ross | |
| 6,511,666 B1 | 1/2003 | Reynolds et al. | |
| 6,528,038 B1 | 3/2003 | Reynolds et al. | |
| 6,576,226 B1 | 6/2003 | Jernberg | |
| 6,962,706 B1 | 11/2005 | O'Brien-Simpson et al. | |
| 7,204,991 B2 | 4/2007 | Barr et al. | |
| 7,262,271 B2 | 8/2007 | Reynolds et al. | |
| 7,341,727 B1 | 3/2008 | Tucker et al. | |
| 7,416,852 B2 | 8/2008 | Proguiske-Fox et al. | |
| 7,419,671 B2 * | 9/2008 | Reynolds et al. .......... 424/190.1 |
| 7,544,777 B2 | 6/2009 | Ross et al. | |
| 7,749,502 B2 | 7/2010 | Reynolds et al. | |
| 2003/0083287 A1 | 5/2003 | Burgess et al. | |
| 2005/0288866 A1 | 12/2005 | Sachdeva et al. | |
| 2006/0073161 A1 | 4/2006 | Breton | |
| 2007/0036734 A1 | 2/2007 | Tahara et al. | |
| 2008/0175867 A1 | 7/2008 | Reynolds et al. | |
| 2010/0034908 A1 | 2/2010 | Ross et al. | |
| 2010/0092471 A1 | 4/2010 | Dashper et al. | |
| 2010/0209362 A1 | 8/2010 | Dashper et al. | |
| 2011/0081358 A1 | 4/2011 | Reynolds et al. | |
| 2011/0104179 A1 | 5/2011 | Reynolds et al. | |
| 2011/0213129 A1 | 9/2011 | Reynolds et al. | |

FOREIGN PATENT DOCUMENTS

| | | |
|---|---|---|
| GB | 2 381 449 | 5/2003 |
| WO | WO 94/27606 | 12/1994 |
| WO | WO 95/07286 | 3/1995 |
| WO | WO 95/09181 A1 | 4/1995 |
| WO | WO 95/11298 | 4/1995 |
| WO | WO 95/26404 A1 | 10/1995 |
| WO | WO 97/34629 A1 | 9/1997 |
| WO | WO 00/75346 A1 | 12/2000 |
| WO | WO 03/055529 | 7/2003 |
| WO | WO 03/080113 | 10/2003 |
| WO | WO 96/17936 A2 | 3/2005 |
| WO | WO 2005/019249 | 3/2005 |
| WO | WO 2005/076010 A2 | 8/2005 |
| WO | WO 2008/016385 | 2/2008 |
| WO | WO 2008/124646 A2 | 10/2008 |

OTHER PUBLICATIONS

Office Action issued on Dec. 27, 2011 by the Examiner in U.S. Appl. No. 12/668,407 (US 2010/0297179).
Office Action issued on Apr. 23, 2012 by the Examiner in U.S. Appl. No. 12/668,407 (US 2010/0297179)
International Search Report issued on Sep. 12, 2008 in application No. PCT/AU2008/001018.
Supplementary Search Report issued on Feb. 9, 2011 in application No. EP 08 77 2643.

(Continued)

*Primary Examiner* — Padma V Baskar
(74) *Attorney, Agent, or Firm* — Foley & Lardner LLP

(57) ABSTRACT

The invention provides a composition for use in raising an immune response to *P. gingivalis* in a subject, the composition comprising an amount effective to raise an immune response of at least one polypeptide having an amino acid sequence substantially identical to at least 50 amino acids, or an antigenic or immunogenic portion, of one of the polypeptides corresponding to accession numbers selected from the group consisting of AAQ65462, AAQ65742, AAQ66991, AAQ65561, AAQ66831, AAQ66797, AAQ66469, AAQ66587, AAQ66654, AAQ66977, AAQ65797, AAQ65867, AAQ65868, AAQ65416, AAQ65449, AAQ66051, AAQ66377, AAQ66444, AAQ66538, AAQ67117 and AAQ67118. The invention also provides a method of preventing or treating a subject for *P. gingivalis* infection comprising administering to the subject a composition of the invention.

4 Claims, 6 Drawing Sheets

(56) References Cited

OTHER PUBLICATIONS

International Search Report issued on Nov. 1, 2005 in application No. PCT/AU2005/001463 (corresponding to US 2009/0175867 and US 2011/0081358).
International Search Report issued on Aug. 17, 2007 in application No. PCT/AU2007/000890 (corresponding to US 2010/0092471).
International Search Report issued on Oct. 13, 2009 in application No. PCT/AU2009/001112 (corresponding to U.S. Appl. No. 13/060,653).
International Search Report issued on Jan. 31, 1997 in application No. PCT/AU96/00673 (corresponding to US 6,511,666 and US 2007/0189982).
International Search Report issued on Jan. 28, 1999 in application No. PCT/AU98/01023 (corresponding to US 7,544,777 and US 2010/0034908).
International Search Report issued on Sep. 12, 2008 in application No. PCT/AU2008/001017 (corresponding to US 2010/0297179).
Office Action issued on Dec. 27, 2010 by the Examiner in U.S. Appl. No. 12/306,495 (US 2010/0092471).
Office Action issued on Jun. 3, 2010 by the Examiner in U.S. Appl. No. 12/306,495 (US 2010/0092471).
Office Action issued on Mar. 23, 2010 by the Examiner in U.S. Appl. No. 12/306,495 (US 2010/0092471).
Notice of Allowance issued on Dec. 5, 2008 by the Examiner in U.S. Appl. No. 11/589,261 (US 7,544,777).
Office Action issued on May 19, 2008 by the Examiner in U.S. Appl. No. 11/589,261 (US 7,544,777).
Office Action issued on Oct. 30, 2007 by the Examiner in U.S. Appl. No. 11/589,261 (US 7,544,777).
Office Action issued on Apr. 28, 2006 by the Examiner in U.S. Appl. No. 09/581,286.
Office Action issued on Sep. 16, 2005 by the Examiner in U.S. Appl. No. 09/581,286.
Office Action issued on Mar. 24, 2005 by the Examiner in U.S. Appl. No. 09/581,286.
Office Action issued on Aug. 25, 2004 by the Examiner in U.S. Appl. No. 09/581,286.
Office Action issued on Jan. 27, 2004 by the Examiner in U.S. Appl. No. 09/581,286.
Office Action issued on Oct. 1, 2002 by the Examiner in U.S. Appl. No. 09/581,286.
Office Action issued on Nov. 2, 2010 by the Examiner in U.S. Appl. No. 12/382,845 (US 2010/0034908).
Office Action issued on Sep. 17, 2010 by the Examiner in U.S. Appl. No. 11/654,512 (US 2007/0189982).
Office Action issued on Aug. 12, 2009 by the Examiner in U.S. Appl. No. 11/654,512 (US 2007/0189982).
Office Action issued on Oct. 23, 2008 by the Examiner in U.S. Appl. No. 11/654,512 (US 2007/0189982).
Office Action issued on Feb. 7, 2008 by the Examiner in U.S. Appl. No. 11/654,512 (US 2007/0189982).
Office Action issued on Aug. 21, 2007 by the Examiner in U.S. Appl. No. 11/654,512 (US 2007/0189982).
Office Action issued on Dec. 21, 2011 by the Examiner in U.S. Appl. No. 11/729,218 (US 2008/0175867).
Office Action issued on Oct. 29, 2009 by the Examiner in U.S. Appl. No. 11/729,218 (US 2008/0175867).
Office Action issued on Apr. 10, 2009 by the Examiner in U.S. Appl. No. 11/729,218 (US 2008/0175867).
Office Action issued on Aug. 28, 2008 by the Examiner in U.S. Appl. No. 11/729,218 (US 2008/0175867).
Office Action issued on May 12, 2010 by the Examiner in U.S. Appl. No. 11/663,671 (US 2009/0169568).
Office Action issued on Nov. 4, 2009 by the Examiner in U.S. Appl. No. 11/663,671 (US 2009/0169568).
Office Action issued on Jul. 9, 2010 by the Examiner in U.S. Appl. No. 12/382,845 (US 2010/0034908).
Notice of Allowance issued by the Examiner on Nov. 1, 2011 in U.S. Appl. No. 12/382,845 (US 2010/0034908).
Office Action issued by the Examiner on Nov. 2, 2010 in U.S. Appl. No. 12/382,845 (US 2010/0034908).
Office Action issued by the Examiner on Jul. 9, 2010 in U.S. Appl. No. 12/382,845 (US 2010/0034908).
Office Action issued by Examiner on Nov. 25, 2011 in U.S. Appl. No. 12/668,652 (US 2010/0209362).
Rosenstein et al., "Hypothesis: The Humoral Immune Response to Oral Bacteria Provides a Stimulus for the Development of Rheumatoid Arthritis," Inflammation, vol. 28, No. 6, pp. 311-318, 2004.
McGraw et al., "Purification, Characterization, and Sequence Analysis of a Potential Virulence Factor from *Porphyromonas gingivalis*, Peptidylarginine Deiminase," Infection and Immunity, vol. 67, No. 7, pp. 3248-3256, Jul. 1999.
Kyte et al., "A simple method for displaying the hydropathic character of a protein," *Journal of Molecular Biology*, vol. 157, Issue 1, pp. 105-132, May 1982, Abstract.
Aduse Opoku et al., "Characterization, Genetic Analysis, and Expression of a Protease Antigen (PrpRl) of *Porphyromonas gingivalis* W50," Infection & Immunity, vol. 63, No. 12, pp. 4744-4754, Dec. 1995.
Barkocy-Gallagher et al., "Analysis of the *prtP* Gene Encoding Porphypain, a Cysteine Proteinase of *Porphyromonas gingivalis*," *J. of Bacteriolgy*, vol. 178, No. 10, May 1996.
Bedi, "Comparative Study of Four Proteases from Spent Culture Media of *Porphyromonas gingivalis* (FAY-19M-1)," *Preparative Biochemistry*, pp. 133-154, Aug. 1995.
Ciborowski, "Purification and Characterization of Two Forms of a High-Molecular-Weight Cysteine Proteinase (Porphypain) from *Porphyromonas gingivalis*," *J. of Bacteriology*, pp. 4549-4557, 1994.
Okamoto et al., "Structural Characterization of Argingipain, a Novel Arginine-Specific Cysteine Proteinase as a Major Periodontal Pathogenic Factor from *Porphyromonas gingivalis*," *Archives of Biochemistry & Biophysics*, vol. 316, No. 2, pp. 917-925, Feb. 1, 1995.
Pavloff et al., "Molecular Cloning and Structural Characterization of the Arg-gingipain Proteinase of *Porphyromonas gingivalis*," *J. of Biol. Chem.*, vol. 270, No. 3, pp. 1007-1010, Jan. 20, 1995.
Pike et al., "Lysine- and Arginine-specific Proteinases from *Porphyromonas gingivalis*," *J. of Biol. Chem.*, vol. 269, No. 1, pp. 406-411, Jan. 7, 1994.
Slakeski et al., "Characterization of a *Porphyromonas gingivalis* Gene prtR That Encodes an Arginine-Specific Thiol Porteinase and Multiple Adhesins," *Biochem. & Biophys. Res. Comm.*, vol. 224, pp. 605-610, 1996.
Yoshimura, "Characterization of a Trypsin-Like Protease From the Bacterium *Bacteroides gingivalis* Isolated From Human Dental Plaque," *Archs. Oral, Biol.*, vol. 29, No. 7, pp. 559-564, 1984.
Albandar et al., Destructive periodontal disease in adults 30 years of age and older in the United States, 1988-1994, Journal of Periodontology, vol. 70, pp. 13-29, 1999.
Alm et al., The MicrobesOnline Web site for comparative genomics, Genome Research, vol. 15, pp. 1015-1022, 2005.
Bramanti et al. Roles of porphyrins and host iron transport proteins in regulation of growth of *Porphyromonas gingivalis* W50, Journal of Bacteriology, vol. 173, pp. 7330-7339, 1991.
Brochu et al., Acquisition of iron from human transferrin by *Porphyromonas gingivalis*: a role for Arg- and Lys-gingipain activities, Oral Microbiology and Immunology, vol. 16, pp. 79-87, 2001.
Capestany et al., Role of the *Poiphyromonas gingivalis* InlJ Protein in Homotypic and Heterotypic Biofilm Development, Infection and Immunity, vol. 74, pp. 3002-3005, 2006.
Carter et al., Humanization of an Anti-p185HER2 Antibody for Human Cancer Therapy, Proceedings of the National Academy of Science USA, vol. 89, pp. 4285-4289, 1989.
Chen et al., *Porphyromonas gingivalis* gingipains and adhesion to epithelial cells, Infection and Immunity, vol. 69, pp. 3048-3056, 2001.
Cossart et al., Bacterial invasion: the paradigms of enteroinvasive pathogens, Science, vol. 304, pp. 242-248, 2004.
Curtiss et al., A virulent *Salmonella typhimurium* Acya Acrp oral vaccine strains expressing a streptococcal colonization and virulence antigen, Vaccine, vol. 6, pp. 155-160, 1988.

(56) References Cited

OTHER PUBLICATIONS

Dashper et al., Characterization of a novel outer membrane hemin-binding protein of *Porphyromonas gingivalis*, Journal of Bacteriololgy., vol. 182, pp. 6456-6462, 2000.

Dashper et al., Sodium ion-driven serine/threonine transport in *Porphyromonas gingivalis*, Journal of Bacteriology, vol. 183, pp. 4142-4148, 2001.

Dashper et al., Hemoglobin hydrolysis and haem acquisition by *Porphyromonas gingivalis*, Oral Microbiology and Immunology, vol. 9, pp. 50-56, 2004.

Dashper et al., A novel *Porphyromonas gingivalis* FeoB plays a role in manganese accumulation, The Journal of Biological Chemistry, vol. 280, pp. 28095-28102, 2005.

Database Ref. Seq, Accession Nos. NC_002950.2 and N13_904903, Jan. 12, 2009.

Devereaux et al., A comprehensive set of sequence analysis programs for the VAX, Nucleic Acids Research, vol. 12, pp. 387-395, 1984.

Diaz et al., The effect of oxygen on the growth and physiology of *Porphyromonas gingivalis*, Oral Microbiology and Immunology, vol. 19, pp. 88-94, 2004.

Diaz et al., Role of oxyR in the oral anaerobe *Porphyromonas gingivalis*, Journal of Bacteriology, vol. 188, pp. 2454-2462, 2006.

Dramsi et al., Entry of *Listeria monocytogenes* into hepatoeytes requires expression of in inIB, a surface protein of the intemalin multigene family, Molecular Microbiology, vol. 16, pp. 251-261, 1995.

Duran-Pinedo et al., The RprY response regulator of *Porphyromonas gingivalis*, Molecular Microbiology, vol. 64, pp. 1416, 2007.

Eymann et al., A comprehensive proteome map of growing *Bacillus subtilis* cells, Proteomics, vol. 4, pp. 2849-2876, 2004.

Fletcher et al., Virulence of a *Porphyramonas gingivalis* W83 mutant defective in the prtH gene, Infection and Immunity, vol. 63, pp. 1521-1528, 1995.

Genco et al., Characterization of a Tn4351-generated hemin uptake mutant of *Porphyramonas gingivalis*: evidence for the coordinate regulation of virulence factors by hemin, Infection and Immunity, vol. 63, pp. 2459-2466, 1995.

Guina et al., Quantitative proteomic analysis indicates increased synthesis of a quinolone by *Pseudomonas aeruginosa* isolates from cystic fibrosis airways, Proceedings of the National Academy of Science USA, vol. 100, pp. 2771-2776, 2003.

Haffajee et al., Microbial etiological agents of destructive periodontal diseases, Periodontology 2000, vol. 5, pp. 78-111, 1994.

Huse et al., Generation of a large combinatorial library of the immunoglobulin repertoire in phage lambda, Science, vol. 246, pp. 1275-1281, 1989.

Jones et al., Replacing the complementarity-determining regions in a human antibody with those from a mouse, Nature, vol. 321, pp. 522-525, 1986.

Lamont et aL, Interaction of *Porphyromonas gingivalis* with gingival epithelial cells maintained in culture, Oral Microbiology and Immunology, vol. 7, pp. 364-367, 1992.

Lamont et al., *Porphyromonas gingivalis* invasion of gingival epithelial cells, Infection and Immunity, vol. 63, pp. 3878-3885, 1995.

Li et al., Protein profiling with cleavable isotope-coded affinity tag (cICAT) reagents: the yeast salinity stress response, Molecular and Cellular Proteomics, vol. 2, pp. 1198-1204, 2003.

Marino et al., A framework for interpreting the leucine-rich repeats of the *Listeria* intemalins, Proceedings of the National Academy of Science USA, vol. 97, pp. 8784-8788, 2000.

McKee et al., Effect of hemin on the physiology and virulence of *Bacteroides gingivalis* W50, Infection and Immunity, vol. 52, pp. 349-355, 1986.

Moore et al., The bacteria of periodontal diseases, Periodontology 2000, vol. 5, pp. 66-77, 1994.

Needleman et al., A general method applicable to the search for similarities in the amino acid sequence of two proteins, Journal of Molecular Biology, vol. 48, pp. 443-453, 1970.

Nelson et al., "Complete Genome Sequence of the Oral Pathogenic Bacterium *Porphyromonas ginginvalis* Strain W83," J. Bacteriol., vol. 185, No. 18, pp. 5591-5601, 2003.

Okano et al., Proteomics-based analysis of a counter-oxidative stress system in *Porphyromonas gingivalis*, Proteomics, vol. 6, pp. 251-258, 2006.

Park et al., Identification of *Porphyromonas gingivalis* genes specifically expressed in human gingival epithelial cells by using differential display reverse transcription-PCR, Infection and Immunity, vol. 72, pp. 3752-3758, 2004.

Pathirana et al., Flow cytometric analysis of adherence of *Porphyromonas gingivalis* to oral epithelial cells, Infection and Immunity, vol. 75, pp. 2484-2492, 2007.

Peng et al., Evaluation of multidimensional chromatography coupled with tandem mass spectrometry (LC/LC-MS/MS) for large-scale protein analysis: the yeast proteome, Journal of Proteome Research, vol. 2, pp. 43-50, 2003.

Price et al., A novel method for accurate operon predictions in all sequenced prokaryotes, Nucleic Acids Research, vol. 33, pp. 880-892, 2005.

Reichman et al., Reshaping human antibodies for therapy, Natu e, vol. 332, pp. 323-327, 1988.

Ross et al., Identification of vaccine candidate antigens from a genomic analysis of *Porphyromonas gingivalis*, Vaccine, vol. 19, pp. 4135-4142, 2001.

Sabet et al., LPXTG protein In1J, a newly identified internalin involved in *Listeria* monocytogenes virulence, Infection and Immunity, vol. 73, pp. 6912-6922, 2005.

Schifferle et al., Effect of protoporphyrin DC limitation on *Porphyromonas gingivalis*, Journal of Endodonics, vol. 22, pp. 352-355, 1996.

Schramm et al., Nucleotide sequence of the colicin B activity gene cba: consensus pentapeptide among TonB-dependent colicins and receptors, Journal of Bacteriology, vol. 169, pp. 3350-3357, 1987.

Schubert at al., Structure of internalin, a major invasion protein of *Listeria* monocytogenes, in complex with its human receptor E-cadherin, Cell, vol. 111, pp. 825-836, 2002.

Seers et aL, The RgpB C-terminal domain has a role in attachment of RgpB to the outer membrane and belongs to a novel C-terminal-domain family found in *Porphyromonas gingivalis*, Journal of Bacteriolgy, vol. 188, pp. 6376-6386, 2006.

Shah et al., The porphyrin pigmentation of subspecies of *Bacteroides melaninogenicus*, Biochemical Journal, vol. 180, pp. 45-50, 1979.

Sharp et al., The codon Adaptation Index—a measure of directional synonymous codon usage bias, and its potential applications, Nucleic Acids Research, vol. 15, pp. 1281-1295, 1987.

Shi at al., Genetic analyses of proteolysis, hemoglobin binding, and hemagglutination of *Porphyromonas gingivalis*. Construction of mutants with a combination of rgpA, rgpl3, kgp, and hagA, The Journal of Biological Chemistry, vol. 274, pp. 17955-17604, 1999.

Shizukuishi et al., Effect of concentration of compounds containing iron on the growth of *Porphyromonas gingivalis*, FEMS Microbiology Letters, vol. 131, pp. 313-317, 1995.

Simpson et al., Characterization and expression of HmuR, a Tonl3-dependent hemoglobin receptor of *Porphyromonas gingivalis*, Journal of Bacteriology, vol. 182, pp. 5737-5748, 2000.

Smalley et al. Hacinin-binding proteins of *Porphyromonas gingivalis* W50 grown in a chemostat under haemin-1 imitation. Journal of General Microbiology, 1993, vol. 139, pp. 2145-2150.

Smalley et al., The periodontopathogen *Porphyromonas gingivalis* binds iron protoporphyrin IX in the mu-oxo dimeric form: an oxidative buffer and possible pathogenic mechanism, Biochemical Journal, vol. 331 (Pt3), pp. 681-685, 1998.

Smalley et al., The periodontal pathogen *Porphyromonas gingivalis* harnesses the chemistry of the mu-oxo bishaem of iron protoporphyrin IX to protect against hydrogen peroxide, FEMS Microbiology Letters, vol. 183, pp. 159-164, 2000.

Supek et al., INCA: synonymous codon usage analysis and clustering by means of self-organizing map, Bioinformatics, vol. 20, pp. 2329-2330, 2004.

Thompson et al., Clustal W: improving the sensitivity of progressive multiple sequence alignment through sequence weighting, position-

(56) References Cited

OTHER PUBLICATIONS specific gap penalties and weight matrix choice, Nucleic Acids Research, vol. 22, pp. 4673-4680, 1994.

Tribble et al., A *Porphyromonas gingivalis* haloacid dehalogenase family phosphatase interacts with human phosphoproteins and is important for invasion, Proceedings of the National Academy of Science USA, vol. 103, pp. 11027-11032, 2006.

Veith et al., Identification of a novel heterodimetric outer membrane protein *Porphyromonas gingivalis* by two-dimensional gel electrophoreses and peptide mass fingerprinting, European Journal of Biochemistry, vol. 268, pp. 4748-4757, 2001.

Wang et al., An analysis of the proteomic profile for Thermoanaerobacter tengcongensis under optimal culture conditions, Proteomics, vol. 4, pp. 136-150, 2004.

Washburn et al., Large-scale analysis of the yeast proteome by multidimensional protein identification technology, Nature Biotechnology, vol. 19, pp. 242-247, 2001.

Yu et al., Predicting subcellular localization of proteins for Gram-negative bacteria by support vector machines based on n-peptide compositions, Protein Science, vol. 13, pp. 1402-1406, 2004.

Zhang et al., Differential protein expression by *Porphyromonas gingivalis* in response to secreted epithelial cell components, Proteomics, vol. 5, pp. 198-211, 2005.

Houghten et al., "Relative Importance of Position and Individual Amino Acid Residues in Peptide Antigen-Antibody Interactions: Implications in the Mechanism of Antigenic Drift and Antigenic Shift Vaccines," 1986, Fred Brown, Ed.

Lederman et al., "A Single Amino Acid Substitution in a Common African Allele of the CD4 Molecule Ablates Binding of the Monoclonal Antibody, OKT4," Molecular Immunology, vol. 28, pp. 1171-1181, 1991.

Li et al., "β-Endorphin omission analogs: Disssociation of immunoreactivity from other biological activities," Proc. Natl. Acad. Sci. USA, vol. 77, pp. 3211-3214, 1980.

Campbell, "Assay Techniques," Monoclonal Antibody Technology, Chapter 2, 1986.

Bohgal et al., "A cell-associated protein complex of *Porphyromonas gingivalis* W50 composed of Arg- and Lys-specific cysteine proteinases and adhesins," Microbiology, vol. 143, pp. 2485-2495, 1997.

O'Brien-Simpson et al., "RgpA-Kgp Peptide-Based Immunogens Provide Protection Against *Porphyromonas gingivalis* Challenge in Murine Lesion Model," Infection and Immunity, 68(7): 4055-4063, 2000.

Hu et al., "Coptidis rhizome inhibits growth and proteases of oral bacteria," Oral Diseases, vol. 6, No. 5, pp. 297-302, Sep. 1, 2000.

Dashper et al., "Inhibition of *Porphyromonas gingivalis* biofilm by oxante," Antimicrobial Agents and Chemotherapy, vol. 54, No. 3, pp. 1311-1314, Mar. 1, 2010.

European Search Report issued on May 14, 2013 in application No. EP 13 15 2880.

\* cited by examiner

SEQUENCE LISTING

```
<160> NUMBER OF SEQ ID NOS: 92

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg His Pro Glu Tyr Ala Val Ser Val Leu Leu Arg
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Asn Leu Gln Ala Leu Val Gly Arg
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Asn Ala Asn Asn Val Asp Leu Asn Arg
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Cys Thr Glu Ser Leu Val Asn Arg
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Asp Leu Gly Glu Glu His Phe Lys
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Ala Cys Phe Lys Val Glu Gly Pro Lys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Cys Cys Asp Lys Pro Leu Leu Glu Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Tyr Glu Ala Thr Leu Glu Glu Cys Cys Ala Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Leu Val Thr Asp Leu Thr Lys Val His Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Ile Cys Asp Asn Gln Asp Thr Ile Ser Ser Lys
1               5                   10

<210> SEQ ID NO 11
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Thr Ala Leu Val Glu Leu Leu Lys
1               5

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Val Asn Glu Leu Thr Glu Phe Ala Lys
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Gly Glu Tyr Gly Phe Gln Asn Ala Leu Ile Val Arg
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Pro Cys Thr Glu Asp Tyr Leu Ser Leu Ile Leu Asn Arg
1               5                   10

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Val Pro Gln Val Ser Thr Pro Thr Leu Val Glu Val Ser Arg
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Phe Thr Phe His Ala Asp Ile Cys Thr Leu Pro Asp Thr Glu Lys
```

```
<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Pro Cys Phe Ser Ala Leu Thr Pro Asp Glu Thr Tyr Val Pro Lys
1               5                   10                  15

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Glu Phe Val Glu Val Thr Lys
1               5

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: ICAT-modified Cys

<400> SEQUENCE: 19

Thr Tyr Met Ile Asp Thr Asn Asp Ser Glu Asn Asp Cys Ile Ala Arg
1               5                   10                  15

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser His Cys Ile Ala Glu Val Glu Lys
1               5

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Cys Cys Asp Lys Pro Leu Leu Glu Lys
1               5                   10

<210> SEQ ID NO 22
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

His Pro Glu Tyr Ala Val Ser Val Leu Leu Arg
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Ile Cys Asp Asn Gln Asp Thr Ile Ser Ser Lys
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Leu Lys Glu Cys Cys Asp Lys Pro Leu Leu Glu Lys
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Leu His Thr Leu Phe Gly Asp Glu Leu Cys Lys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Val Pro Gln Val Ser Thr Pro Thr Leu Val Glu Val Ser Arg
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Cys Cys His Gly Asp Leu Leu Glu Cys Ala Asp Asp Arg
```

```
1               5                   10

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Leu Phe Thr Phe His Ala Asp Ile Cys Thr Leu Pro Asp Thr Glu Lys
1               5                   10                  15

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Phe Lys Asp Leu Gly Glu Glu His Phe Lys
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Glu Thr Tyr Gly Asp Met Ala Asp Cys Cys Glu Lys
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: ICAT-modified Cys

<400> SEQUENCE: 31

Ile Met Glu Cys Val Pro Asn Phe Ser Glu Gly Arg
1               5                   10

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: ICAT-modified Cys

<400> SEQUENCE: 32

Ile Ala Gly Glu Leu Leu Pro Cys Val Phe His Val Ser Ala Arg
1               5                   10                  15
```

```
<210> SEQ ID NO 33
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: ICAT-modified Cys

<400> SEQUENCE: 33

Ala Phe Asp Asn Gly Ile Ile Cys Ser Gly Glu Gln Ser Ile Ile Tyr
1               5                   10                  15

Asn Glu Ala Asp Lys
            20

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ICAT-modified Cys

<400> SEQUENCE: 34

Cys Ser Ala His Ala Val Arg
1               5

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: ICAT-modified Cys

<400> SEQUENCE: 35

Glu Tyr Gln Ala Thr His Asn Gln Glu Ala Val Asp Asn Ile Cys Arg
1               5                   10                  15

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: ICAT-modified Cys

<400> SEQUENCE: 36

Gly Val Gly Ala Glu Asp Val Ile Cys Lys
1               5                   10

<210> SEQ ID NO 37
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: ICAT-modified Cys

<400> SEQUENCE: 37

Asn His Gly Ala Tyr Phe Cys Asp Glu Ala Glu Gly Asp Arg
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: ICAT-modified Cys

<400> SEQUENCE: 38

Thr Cys Asn Ala Ile Ile Ile Ala Pro His Pro Arg
1               5                   10

<210> SEQ ID NO 39
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: ICAT-modified Cys

<400> SEQUENCE: 39

Glu Leu Ile Ile Val Pro Thr Thr Cys Gly Thr Gly Ser Glu Val Thr
1               5                   10                  15

Asn Ile Ser Ile Ala Glu Ile Lys
            20

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: ICAT-modified Cys

<400> SEQUENCE: 40

Ile Leu Asn Cys Gln Pro Glu Tyr Val Tyr Pro Lys
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (7)..(7)
<223> OTHER INFORMATION: ICAT-modified Cys

<400> SEQUENCE: 41

Leu Asp Glu Leu Leu Gly Cys Leu Leu Thr Lys
1               5                   10

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: ICAT-modified Cys

<400> SEQUENCE: 42

Ala Gly Asn Tyr Met Ile Asp Leu Leu Leu Ala Asn Val Cys Lys
1               5                   10                  15

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: ICAT-modified Cys

<400> SEQUENCE: 43

Thr Ala Ser Cys Phe Gln Arg
1               5

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: ICAT-modified Cys

<400> SEQUENCE: 44

Thr Asp Ile Ser Glu Ser Ala Ala Asp Val Leu Asp Glu Pro Ile Val
1               5                   10                  15

Val Cys Arg

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: ICAT-modified Cys
```

```
<400> SEQUENCE: 45

Met Ile Ile Thr Ala Ala Ile Cys Gly Ala Glu Val Leu Lys
1               5                   10

<210> SEQ ID NO 46
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: ICAT-modified Cys

<400> SEQUENCE: 46

Ala Val Cys Pro Asp Val Ile Ile Gln Pro Ser Thr Gly Gly Ala Val
1               5                   10                  15

Gly Met Thr Asn Asp Glu Arg
            20

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: ICAT-modified Cys

<400> SEQUENCE: 47

Leu Tyr Cys Ala Glu Thr Ala Met Asp Met Thr Thr Lys
1               5                   10

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: ICAT-modified Cys

<400> SEQUENCE: 48

Ser Ile Ala Gln Phe Gln Asn Thr Gln Phe Gln Leu Ala Asp Leu Gln
1               5                   10                  15

Cys Arg

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: ICAT-modified Cys

<400> SEQUENCE: 49
```

Val Thr Ala Ile Leu Cys Gly Tyr Lys
1               5

<210> SEQ ID NO 50
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: ICAT-modified Cys

<400> SEQUENCE: 50

Thr Gly Leu Thr Ala Asp Cys Thr Ser Leu Glu Ile Gly Asp Glu Arg
1               5                   10                  15

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: ICAT-modified Cys

<400> SEQUENCE: 51

Val Leu Val Leu Asn Cys Gly Ser Ser Ser Val Lys
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: ICAT-modified Cys

<400> SEQUENCE: 52

Ala Cys Glu Ile Leu Gly Leu Asp Tyr Asp Lys
1               5                   10

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: ICAT-modified Cys

<400> SEQUENCE: 53

Val Glu Glu Cys Ile Pro Leu Ala Pro Leu His Asn Pro Ala Asn Leu
1               5                   10                  15

Lys

-continued

```
<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: ICAT-modified Cys

<400> SEQUENCE: 54

Ala Ala Glu Leu Val Glu Asn Pro Leu Tyr Leu Gly Cys Leu Ile Val
1               5                   10                  15

Lys

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: ICAT-modified Cys

<400> SEQUENCE: 55

Gly Cys Ser Val Glu Asp Ile Tyr Arg
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ICAT-modified Cys

<400> SEQUENCE: 56

Cys Met Leu Asp Leu Arg
1               5

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: ICAT-modified Cys

<400> SEQUENCE: 57

Leu Arg Pro Glu Ser Thr Gly Phe Gly Ala Val Tyr Phe Val Gln Asn
1               5                   10                  15

Met Cys Lys

<210> SEQ ID NO 58
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: ICAT-modified Cys

<400> SEQUENCE: 58

Ala Val Ile Ile Val Cys Asp Gly Asn Phe His Gly Arg
1               5                   10

<210> SEQ ID NO 59
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: ICAT-modified Cys

<400> SEQUENCE: 59

Tyr Phe Asp Phe Leu Ser Ala Tyr Ser Ala Val Asn Gln Gly His Cys
1               5                   10                  15

His Pro Lys

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: ICAT-modified Cys

<400> SEQUENCE: 60

Gly Gln Leu Pro Phe Cys Gln Asp Thr Gly Thr Ala Ile Ile Leu Gly
1               5                   10                  15

Lys

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: ICAT-modified Cys
<220> FEATURE:
<221> NAME/KEY: MOD_RES
<222> LOCATION: (13)..(13)
<223> OTHER INFORMATION: ICAT-modified Cys

<400> SEQUENCE: 61

His Gly Ala Ser Cys Pro Val Gly Met Gly Val Ser Cys Ser Ala Asp
1               5                   10                  15

Arg
```

```
<210> SEQ ID NO 62
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: ICAT-modified Cys

<400> SEQUENCE: 62

Phe Asn Gly Gln Ser Val Gly Ile Val Ala Asn Gln Pro Gln Val Met
1               5                   10                  15

Ala Gly Cys Leu Asp Ser Asn Ala Ser Arg
            20                  25

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ICAT-modified Cys

<400> SEQUENCE: 63

Cys Thr Asn Phe Gly Ile Asp Lys
1               5

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: ICAT-modified Cys

<400> SEQUENCE: 64

Met Asp Glu Leu Gly Phe Gly Asn Cys Thr Asn Thr Arg
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: ICAT-modified Cys

<400> SEQUENCE: 65

Ala Pro Val Val Phe Asp His Asp Cys Arg
1               5                   10

<210> SEQ ID NO 66
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: ICAT-modified Cys

<400> SEQUENCE: 66

Leu Ala Glu Val Ser Asn Ala Ile Ile Asp Gln Cys Val Ala Gln Gly
1               5                   10                  15

Val Pro Phe Ala Arg
            20

<210> SEQ ID NO 67
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ICAT-modified Cys

<400> SEQUENCE: 67

Cys Gly Leu His Glu Phe Asn Leu Pro Ala Met Gln Pro Gly Ser Ser
1               5                   10                  15

Ile Met Pro Gly Lys
            20

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: ICAT-modified Cys

<400> SEQUENCE: 68

Val Asn Pro Val Ile Pro Glu Val Met Asn Gln Ile Cys Tyr Lys
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: ICAT-modified Cys

<400> SEQUENCE: 69

Ile Ala Asp Met Leu Ala Leu Leu Asp Gly Thr Cys Leu Val Thr Arg
1               5                   10                  15

<210> SEQ ID NO 70
<211> LENGTH: 23
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: ICAT-modified Cys

<400> SEQUENCE: 70

```
Leu Thr Pro Asn Leu Cys Leu Tyr Asp Pro Phe Ala Val Gly Leu Glu
1               5                   10                  15
Gly Val Ala Glu Glu Ile Arg
            20
```

<210> SEQ ID NO 71
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: ICAT-modified Cys

<400> SEQUENCE: 71

```
Met Asn Ser Asp Glu Leu Phe Glu Glu Ile Thr Tyr Pro Gly Tyr Thr
1               5                   10                  15
Ile Cys Arg
```

<210> SEQ ID NO 72
<211> LENGTH: 554
<212> TYPE: PRT
<213> ORGANISM: Porphyromonas gingivalis

<400> SEQUENCE: 72

```
Met Arg Ile Lys Pro Ser Leu Lys Thr Met Lys Lys Ile Ser Ala Tyr
1               5                   10                  15
Val Ile Gly Ala Ala Leu Ser Val Ala Ser Gly Val Pro Ser Val Tyr
                20                  25                  30
Ala Gln Gly Glu Ala Asp Ala Ile Arg Tyr Ser Arg Thr Glu Leu Gly
            35                  40                  45
Gly Ser Ala Arg Phe Arg Ser Met Ala Gly Ala Phe Gly Ala Leu Gly
        50                  55                  60
Gly Asp Phe Ser Ala Ile Gly Gln Asn Pro Ala Gly Leu Gly Ile Phe
65                  70                  75                  80
Arg Ser Ser Glu Val Ser Ala Thr Ile Asp Phe Ser Ser Ile Ser Asn
                85                  90                  95
Gln Ala Ala Trp Gln Gly Ser Ser Glu Thr Phe Asn Lys Asn Lys Leu
            100                 105                 110
Leu Phe Thr Gly Ile Gly Tyr Val Gly Ser Trp Gly Lys Ala Asn Glu
        115                 120                 125
Asp Val Ser Val Asn Phe Gly Leu Gly Ala Lys Arg Val Leu Asp Tyr
    130                 135                 140
Glu Arg Ser Phe Arg Ile Ala Gly Gly Glu Gln Lys Phe Ser Val Ala
145                 150                 155                 160
Asp Tyr Val Ala Ala Gln Thr Pro Gly Lys Ala Asn Pro Ser His Phe
                165                 170                 175
Asn Tyr Asn Gly Leu Glu Ser Ser Trp Leu Thr Asp Leu Gly Tyr Asn
            180                 185                 190
```

```
Ala Gly Trp Ile Ala Gln Leu Pro Gly Gly Tyr Gly Phe Glu Ser Ile
            195                 200                 205

Phe Lys Tyr Lys Gln Asn Gly Glu Tyr Gln Ile Phe Gly Pro Ser Ser
    210                 215                 220

Thr Ala Phe Asp Leu Lys Glu Thr Gly His Val Trp Asn Tyr Asp Phe
225                 230                 235                 240

Gly Leu Gly Ile Asn Ile Gln Asp Thr Trp Tyr Leu Gly Ala Ser Met
                245                 250                 255

Thr Tyr Ser Asp Leu Gln Phe Asp Thr Asn Thr Phe Tyr Gln Glu Asn
            260                 265                 270

Phe Ser Phe Asn Asn Gly Ala Ile Asn Asp Tyr Leu Lys Leu Glu Asn
    275                 280                 285

Thr Leu Ser Thr Ser Gly Ser Gly Leu Asn Ile Gly Ile Gly Ala Ile
290                 295                 300

Tyr Arg Pro Ala Asp Ala Val Arg Ile Gly Leu Ser Tyr Tyr Thr Pro
305                 310                 315                 320

Thr Trp Tyr Trp Met Lys Ser Tyr Tyr Arg Ala Tyr Gly Ser Ser Tyr
                325                 330                 335

Tyr Ser Gln Gly Val Asp Ser Asn Gly Gln Pro Leu Pro Glu Asn Leu
            340                 345                 350

Tyr Phe Met Ser Ser Gln Thr Pro Glu Ser Tyr Asn Thr Tyr Gln Met
    355                 360                 365

Ser Ser Pro Gly Arg Phe Val Ala Ser Leu Ala Val Ala Gly Lys
370                 375                 380

Ile Gly Leu Leu Ser Met Asp Tyr Glu Leu Glu Ser Tyr Gly Gln Ile
385                 390                 395                 400

Lys Leu Lys Asp Glu Asn Gly Thr Ala Tyr Val Asp Asn Lys Phe Ile
                405                 410                 415

Ser Glu Asp Phe Gly Ser Arg His Thr Ile Arg Leu Gly Gly Glu Leu
            420                 425                 430

Arg Pro Ile Ser Arg Leu Ser Leu Arg Ala Gly Tyr Ser His Thr Ser
    435                 440                 445

Asn Pro Ile Lys Asn Glu Lys Leu Lys Ala Phe Asp Gly Ser Ala Gln
450                 455                 460

Val Thr Val Phe Pro Met Gly Ala Met Pro His Tyr Glu Leu Pro Gly
465                 470                 475                 480

Asn Ser Tyr Thr Val Thr Gly Leu Gly Tyr Arg Phe Thr Arg Asn
                485                 490                 495

Leu Ser Gly Asp Leu Ala Val Ile Tyr Arg Asn Glu Lys Ser Tyr Tyr
            500                 505                 510

Tyr Thr Phe Gly Arg Met Val Ser Asp Asp Pro Asn Pro Ala Asn Val
    515                 520                 525

Leu Glu Val Glu Ser Pro Ala Pro Ala Lys Leu Thr Arg Ser Asn Phe
530                 535                 540

Arg Leu Ala Met Thr Met Ser Tyr Arg Phe
545                 550

<210> SEQ ID NO 73
<211> LENGTH: 821
<212> TYPE: PRT
<213> ORGANISM: Porphyromonas gingivalis

<400> SEQUENCE: 73

Met Lys Lys Lys Asn Phe Leu Leu Leu Gly Ile Phe Val Ala Leu Leu
1               5                   10                  15
```

-continued

```
Thr Phe Ile Gly Ser Met Gln Ala Gln Gln Ala Lys Asp Tyr Phe Asn
             20                  25                  30
Phe Asp Glu Arg Gly Glu Ala Tyr Phe Ser Phe Lys Val Pro Asp Arg
         35                  40                  45
Ala Val Leu Gln Glu Leu Ala Leu Ile Met Ser Ile Asp Glu Phe Asp
 50                  55                  60
Pro Val Thr Asn Glu Ala Ile Ala Tyr Ala Ser Glu Glu Glu Phe Glu
 65                  70                  75                  80
Ala Phe Leu Arg Tyr Gly Leu Lys Pro Thr Phe Leu Thr Pro Pro Ser
                 85                  90                  95
Met Gln Arg Ala Val Glu Met Phe Asp Tyr Arg Ser Gly Glu Lys Tyr
            100                 105                 110
Glu Trp Asn Ala Tyr Pro Thr Tyr Glu Ala Tyr Ile Ser Met Met Glu
        115                 120                 125
Glu Phe Gln Thr Lys Tyr Pro Ser Leu Cys Thr Thr Ser Val Ile Gly
    130                 135                 140
Lys Ser Val Lys Asp Arg Lys Leu Met Ile Cys Lys Leu Thr Ser Ser
145                 150                 155                 160
Ala Asn Thr Gly Lys Lys Pro Arg Val Leu Tyr Thr Ser Thr Met His
                165                 170                 175
Gly Asp Glu Thr Thr Gly Tyr Val Val Leu Arg Leu Ile Asp His
            180                 185                 190
Leu Leu Ser Asn Tyr Glu Ser Asp Pro Arg Ile Lys Asn Ile Leu Asp
        195                 200                 205
Lys Thr Glu Val Trp Ile Cys Pro Leu Thr Asn Pro Asp Gly Ala Tyr
    210                 215                 220
Arg Ala Gly Asn His Thr Val Gln Gly Ala Thr Arg Tyr Asn Ala Asn
225                 230                 235                 240
Asn Val Asp Leu Asn Arg Asn Phe Lys Asp Asp Val Ala Gly Asp His
                245                 250                 255
Pro Asp Gly Lys Pro Trp Gln Pro Glu Ala Thr Ala Phe Met Asp Leu
            260                 265                 270
Glu Gly Asn Thr Ser Phe Val Leu Gly Ala Asn Ile His Gly Gly Thr
        275                 280                 285
Glu Val Val Asn Tyr Pro Trp Asp Asn Lys Lys Glu Arg His Ala Asp
    290                 295                 300
Asp Glu Trp Tyr Lys Leu Ile Ser Arg Asn Tyr Ala Ala Ala Cys Gln
305                 310                 315                 320
Ser Ile Ser Ala Ser Tyr Met Thr Ser Thr Asn Ser Gly Ile Ile
                325                 330                 335
Asn Gly Ser Asp Trp Tyr Val Ile Arg Gly Ser Arg Gln Asp Asn Ala
            340                 345                 350
Asn Tyr Phe His Arg Leu Arg Glu Ile Thr Leu Glu Ile Ser Asn Thr
        355                 360                 365
Lys Leu Val Pro Ala Ser Gln Leu Pro Lys Tyr Trp Asn Leu Asn Lys
    370                 375                 380
Glu Ser Leu Leu Ala Leu Ile Glu Glu Ser Leu Tyr Gly Ile His Gly
385                 390                 395                 400
Thr Val Thr Ser Ala Ala Asn Gly Gln Pro Leu Lys Cys Gln Ile Leu
                405                 410                 415
Ile Glu Asn His Asp Lys Arg Asn Ser Asp Val Tyr Ser Asp Ala Thr
            420                 425                 430
```

Thr Gly Tyr Tyr Val Arg Pro Ile Lys Ala Gly Tyr Thr Val Lys
        435                 440                 445

Tyr Lys Ala Glu Gly Tyr Pro Glu Ala Thr Arg Thr Ile Thr Ile Lys
450                 455                 460

Asp Lys Glu Thr Val Ile Met Asp Ile Ala Leu Gly Asn Ser Val Pro
465                 470                 475                 480

Leu Pro Val Pro Asp Phe Thr Ala Ser Pro Met Thr Ile Ser Val Gly
            485                 490                 495

Glu Ser Val Gln Phe Gln Asp Gln Thr Thr Asn Asn Pro Thr Asn Trp
        500                 505                 510

Glu Trp Thr Phe Glu Gly Gly Gln Pro Ala Met Ser Thr Glu Gln Asn
        515                 520                 525

Pro Leu Val Ser Tyr Ser His Pro Gly Gln Tyr Asp Val Thr Leu Lys
        530                 535                 540

Val Trp Asn Ala Ser Gly Ser Asn Thr Ile Thr Lys Glu Lys Phe Ile
545                 550                 555                 560

Thr Val Asn Ala Val Met Pro Val Ala Glu Phe Val Gly Thr Pro Thr
                565                 570                 575

Glu Ile Glu Glu Gly Gln Thr Val Ser Phe Gln Asn Gln Ser Thr Asn
            580                 585                 590

Ala Thr Asn Tyr Val Trp Ile Phe Asp Gly Gly Thr Pro Ala Thr Ser
        595                 600                 605

Glu Asp Glu Asn Pro Thr Val Leu Tyr Ser Lys Ala Gly Gln Tyr Asp
        610                 615                 620

Val Thr Leu Lys Ala Ile Ser Ala Ser Gly Glu Thr Val Lys Thr Lys
625                 630                 635                 640

Glu Lys Tyr Ile Thr Val Lys Lys Ala Pro Val Pro Ala Pro Val Ala
                645                 650                 655

Asp Phe Glu Gly Thr Pro Arg Lys Val Lys Lys Gly Glu Thr Val Thr
            660                 665                 670

Phe Lys Asp Leu Ser Thr Asn Asn Pro Thr Ser Trp Leu Trp Val Phe
        675                 680                 685

Glu Gly Gly Ser Pro Ala Thr Ser Thr Glu Gln Asn Pro Val Val Thr
        690                 695                 700

Tyr Asn Glu Thr Gly Lys Tyr Asp Val Gln Leu Thr Ala Thr Asn Glu
705                 710                 715                 720

Gly Gly Ser Asn Val Lys Lys Ala Glu Asp Tyr Ile Glu Val Ile Leu
                725                 730                 735

Asp Asp Ser Val Glu Asp Ile Val Ala Gln Thr Gly Ile Val Ile Arg
            740                 745                 750

Pro Gln Asn Gly Thr Lys Gln Ile Leu Ile Glu Ala Asn Ala Ala Ile
        755                 760                 765

Lys Ala Ile Val Leu Tyr Asp Ile Asn Gly Arg Val Val Leu Lys Thr
770                 775                 780

Thr Pro Asn Gln Leu Arg Ser Thr Val Asp Leu Ser Ile Leu Pro Glu
785                 790                 795                 800

Gly Ile Tyr Thr Ile Asn Ile Lys Thr Glu Lys Ser Ala Arg Thr Glu
                805                 810                 815

Lys Ile His Ile Gly
            820

<210> SEQ ID NO 74
<211> LENGTH: 940
<212> TYPE: PRT

<213> ORGANISM: Porphyromonas gingivalis

<400> SEQUENCE: 74

```
Met Asn Lys Phe Tyr Lys Ser Leu Leu Gln Ser Gly Leu Ala Ala Phe
1               5                   10                  15

Val Ser Met Ala Thr Ala Leu Thr Ala Ser Ala Gln Ile Ser Phe Gly
            20                  25                  30

Gly Glu Pro Leu Ser Phe Ser Arg Ser Ala Gly Thr His Ser Phe
        35                  40                  45

Asp Asp Ala Met Thr Ile Arg Leu Thr Pro Asp Phe Asn Pro Glu Asp
    50                  55                  60

Leu Ile Ala Gln Ser Arg Trp Gln Ser Gln Arg Asp Gly Arg Pro Val
65                  70                  75                  80

Arg Ile Gly Gln Val Ile Pro Val Asp Val Asp Phe Ala Ser Lys Ala
                    85                  90                  95

Ser His Ile Ser Ser Ile Gly Asp Val Asp Val Tyr Arg Leu Gln Phe
                100                 105                 110

Lys Leu Glu Gly Ala Lys Ala Ile Thr Leu Tyr Tyr Asp Ala Phe Asn
            115                 120                 125

Ile Pro Glu Gly Gly Arg Leu Tyr Ile Tyr Thr Pro Asp His Glu Ile
    130                 135                 140

Val Leu Gly Ala Tyr Thr Asn Ala Thr His Arg Arg Asn Gly Ala Phe
145                 150                 155                 160

Ala Thr Glu Pro Val Pro Gly Ser Glu Leu Ile Met Asp Tyr Glu Val
                    165                 170                 175

Ser Arg Gly Gly Thr Leu Pro Asp Ile Lys Ile Ser Gly Ala Gly Tyr
                180                 185                 190

Ile Phe Asp Lys Val Gly Gly Arg Pro Val Thr Asp Asn His Tyr Gly
            195                 200                 205

Ile Gly Glu Asp Asp Ser Asp Ser Asp Cys Glu Ile Asn Ile Asn Cys
    210                 215                 220

Pro Glu Gly Ala Asp Trp Gln Ala Glu Lys Asn Gly Val Val Gln Met
225                 230                 235                 240

Ile Met Val Lys Gly Gln Tyr Ile Ser Met Cys Ser Gly Asn Leu Leu
                    245                 250                 255

Asn Asn Thr Lys Gly Asp Phe Thr Pro Leu Ile Ile Ser Ala Gly His
                260                 265                 270

Cys Ala Ser Ile Thr Thr Asn Phe Gly Val Thr Gln Ser Glu Leu Asp
            275                 280                 285

Lys Trp Ile Phe Thr Phe His Tyr Glu Lys Arg Gly Cys Ser Asn Gly
    290                 295                 300

Thr Leu Ala Ile Phe Arg Gly Asn Ser Ile Ile Gly Ala Ser Met Lys
305                 310                 315                 320

Ala Phe Leu Pro Ile Lys Gly Lys Ser Asp Gly Leu Leu Gln Leu
                    325                 330                 335

Asn Asp Glu Val Pro Leu Arg Tyr Arg Val Tyr Tyr Asn Gly Trp Asp
                340                 345                 350

Ser Thr Pro Asp Ile Pro Ser Ser Gly Ala Gly Ile His His Pro Ala
            355                 360                 365

Gly Asp Ala Met Lys Ile Ser Ile Leu Lys Lys Thr Pro Ala Leu Asn
    370                 375                 380

Thr Trp Ile Ser Ser Ser Gly Ser Gly Gly Thr Asp Asp His Phe Tyr
385                 390                 395                 400
```

```
Phe Lys Tyr Asp Gln Gly Gly Thr Glu Gly Ser Ser Gly Ser Ser
                405                 410                 415
Leu Phe Asn Gln Asn Lys His Val Val Gly Thr Leu Thr Gly Gly Ala
            420                 425                 430
Gly Asn Cys Gly Gly Thr Glu Phe Tyr Gly Arg Leu Asn Ser His Trp
        435                 440                 445
Asn Glu Tyr Ala Ser Asp Gly Asn Thr Ser Arg Met Asp Ile Tyr Leu
    450                 455                 460
Asp Pro Gln Asn Asn Gly Gln Thr Thr Ile Leu Asn Gly Thr Tyr Arg
465                 470                 475                 480
Asp Gly Tyr Lys Pro Leu Pro Ser Val Pro Arg Leu Leu Gln Ser
                485                 490                 495
Thr Gly Asp Gln Val Glu Leu Asn Trp Thr Ala Val Pro Ala Asp Gln
            500                 505                 510
Tyr Pro Ser Ser Tyr Gln Val Glu Tyr His Ile Phe Arg Asn Gly Lys
        515                 520                 525
Glu Ile Ala Thr Thr Lys Glu Leu Ser Tyr Ser Asp Ala Ile Asp Glu
    530                 535                 540
Ser Ile Ile Gly Ser Gly Ile Ile Arg Tyr Glu Val Ser Ala Arg Phe
545                 550                 555                 560
Ile Tyr Pro Ser Pro Leu Asp Gly Val Glu Ser Tyr Lys Asp Thr Asp
                565                 570                 575
Lys Thr Ser Ala Asp Leu Ala Ile Gly Asp Ile Gln Thr Lys Leu Lys
            580                 585                 590
Pro Asp Val Thr Pro Leu Pro Gly Gly Gly Val Ser Leu Ser Trp Lys
        595                 600                 605
Val Pro Phe Leu Ser Gln Leu Val Ser Arg Phe Gly Glu Ser Pro Asn
    610                 615                 620
Pro Val Phe Lys Thr Phe Glu Val Pro Tyr Val Ser Ala Ala Ala
625                 630                 635                 640
Gln Thr Pro Asn Pro Pro Val Gly Val Val Ile Ala Asp Lys Phe Met
                645                 650                 655
Ala Gly Thr Tyr Pro Glu Lys Ala Ala Ile Ala Ala Val Tyr Val Met
            660                 665                 670
Pro Ser Ala Pro Asp Ser Thr Phe His Leu Phe Leu Lys Ser Asn Thr
        675                 680                 685
Asn Arg Arg Leu Gln Lys Val Thr Thr Pro Ser Asp Trp Gln Ala Gly
    690                 695                 700
Thr Trp Leu Arg Ile Asn Leu Asp Lys Pro Phe Pro Val Asn Asn Asp
705                 710                 715                 720
His Met Leu Phe Ala Gly Ile Arg Met Pro Asn Lys Tyr Lys Leu Asn
                725                 730                 735
Arg Ala Ile Arg Tyr Val Arg Asn Pro Asp Asn Leu Phe Ser Ile Thr
            740                 745                 750
Gly Lys Lys Ile Ser Tyr Asn Asn Gly Val Ser Phe Glu Gly Tyr Gly
        755                 760                 765
Ile Pro Ser Leu Leu Gly Tyr Met Ala Ile Lys Tyr Leu Val Val Asn
    770                 775                 780
Thr Asp Ala Pro Lys Ile Asp Met Ser Leu Val Gln Glu Pro Tyr Ala
785                 790                 795                 800
Lys Gly Thr Asn Val Ala Pro Phe Pro Glu Leu Val Gly Ile Tyr Val
                805                 810                 815
Tyr Lys Asn Gly Thr Phe Ile Gly Thr Gln Asp Pro Ser Val Thr Thr
```

```
              820             825             830
Tyr Ser Val Ser Asp Gly Thr Glu Ser Asp Glu Tyr Glu Ile Lys Leu
            835             840             845
Val Tyr Lys Gly Ser Gly Ile Ser Asn Gly Val Ala Gln Ile Glu Asn
            850             855             860
Asn Asn Ala Val Val Ala Tyr Pro Ser Val Val Thr Asp Arg Phe Ser
865             870             875             880
Ile Lys Asn Ala His Met Val His Ala Ala Leu Tyr Ser Leu Asp
            885             890             895
Gly Lys Gln Val Arg Ser Trp Asn Asn Leu Arg Asn Gly Val Thr Phe
            900             905             910
Ser Val Gln Gly Leu Thr Ala Gly Thr Tyr Met Leu Val Met Gln Thr
            915             920             925
Ala Asn Gly Pro Val Ser Gln Lys Ile Val Lys Gln
            930             935             940

<210> SEQ ID NO 75
<211> LENGTH: 1706
<212> TYPE: PRT
<213> ORGANISM: Porphyromonas gingivalis

<400> SEQUENCE: 75

Met Lys Asn Leu Asn Lys Phe Val Ser Ile Ala Leu Cys Ser Ser Leu
1               5                   10                  15
Leu Gly Gly Met Ala Phe Ala Gln Gln Thr Glu Leu Gly Arg Asn Pro
            20                  25                  30
Asn Val Arg Leu Leu Glu Ser Thr Gln Gln Ser Val Thr Lys Val Gln
        35                  40                  45
Phe Arg Met Asp Asn Leu Lys Phe Thr Glu Val Gln Thr Pro Lys Gly
    50                  55                  60
Met Ala Gln Val Pro Thr Tyr Thr Glu Gly Val Asn Leu Ser Glu Lys
65                  70                  75                  80
Gly Met Pro Thr Leu Pro Ile Leu Ser Arg Ser Leu Ala Val Ser Asp
                85                  90                  95
Thr Arg Glu Met Lys Val Glu Val Ser Ser Lys Phe Ile Glu Lys
            100                 105                 110
Lys Asn Val Leu Ile Ala Pro Ser Lys Gly Met Ile Met Arg Asn Glu
        115                 120                 125
Asp Pro Lys Lys Ile Pro Tyr Val Tyr Gly Lys Ser Tyr Ser Gln Asn
    130                 135                 140
Lys Phe Phe Pro Gly Glu Ile Ala Thr Leu Asp Asp Pro Phe Ile Leu
145                 150                 155                 160
Arg Asp Val Arg Gly Gln Val Val Asn Phe Ala Pro Leu Gln Tyr Asn
                165                 170                 175
Pro Val Thr Lys Thr Leu Arg Ile Tyr Thr Glu Ile Thr Val Ala Val
            180                 185                 190
Ser Glu Thr Ser Glu Gln Gly Lys Asn Ile Leu Asn Lys Lys Gly Thr
        195                 200                 205
Phe Ala Gly Phe Glu Asp Thr Tyr Lys Arg Met Phe Met Asn Tyr Glu
    210                 215                 220
Pro Gly Arg Tyr Thr Pro Val Glu Lys Gln Asn Gly Arg Met Ile
225                 230                 235                 240
Val Ile Val Ala Lys Lys Tyr Glu Gly Asp Ile Lys Asp Phe Val Asp
                245                 250                 255
```

-continued

```
Trp Lys Asn Gln Arg Gly Leu Arg Thr Glu Val Lys Val Ala Glu Asp
            260                 265                 270

Ile Ala Ser Pro Val Thr Ala Asn Ala Ile Gln Gln Phe Val Lys Gln
        275                 280                 285

Glu Tyr Glu Lys Glu Gly Asn Asp Leu Thr Tyr Val Leu Leu Ile Gly
    290                 295                 300

Asp His Lys Asp Ile Pro Ala Lys Ile Thr Pro Gly Ile Lys Ser Asp
305                 310                 315                 320

Gln Val Tyr Gly Gln Ile Val Gly Asn Asp His Tyr Asn Glu Val Phe
                325                 330                 335

Ile Gly Arg Phe Ser Cys Glu Ser Lys Glu Asp Leu Lys Thr Gln Ile
            340                 345                 350

Asp Arg Thr Ile His Tyr Glu Arg Asn Ile Thr Thr Glu Asp Lys Trp
        355                 360                 365

Leu Gly Gln Ala Leu Cys Ile Ala Ser Ala Glu Gly Gly Pro Ser Ala
    370                 375                 380

Asp Asn Gly Glu Ser Asp Ile Gln His Glu Asn Val Ile Ala Asn Leu
385                 390                 395                 400

Leu Thr Gln Tyr Gly Tyr Thr Lys Ile Ile Lys Cys Tyr Asp Pro Gly
                405                 410                 415

Val Thr Pro Lys Asn Ile Ile Asp Ala Phe Asn Gly Gly Ile Ser Leu
            420                 425                 430

Ala Asn Tyr Thr Gly His Gly Ser Glu Thr Ala Trp Gly Thr Ser His
        435                 440                 445

Phe Gly Thr Thr His Val Lys Gln Leu Thr Asn Ser Asn Gln Leu Pro
    450                 455                 460

Phe Ile Phe Asp Val Ala Cys Val Asn Gly Asp Phe Leu Phe Ser Met
465                 470                 475                 480

Pro Cys Phe Ala Glu Ala Leu Met Arg Ala Gln Lys Asp Gly Lys Pro
                485                 490                 495

Thr Gly Thr Val Ala Ile Ile Ala Ser Thr Ile Asn Gln Ser Trp Ala
            500                 505                 510

Ser Pro Met Arg Gly Gln Asp Glu Met Asn Glu Ile Leu Cys Glu Lys
        515                 520                 525

His Pro Asn Asn Ile Lys Arg Thr Phe Gly Gly Val Thr Met Asn Gly
    530                 535                 540

Met Phe Ala Met Val Glu Lys Tyr Lys Lys Asp Gly Glu Lys Met Leu
545                 550                 555                 560

Asp Thr Trp Thr Val Phe Gly Asp Pro Ser Leu Leu Val Arg Thr Leu
                565                 570                 575

Val Pro Thr Lys Met Gln Val Thr Ala Pro Ala Gln Ile Asn Leu Thr
            580                 585                 590

Asp Ala Ser Val Asn Val Ser Cys Asp Tyr Asn Gly Ala Ile Ala Thr
        595                 600                 605

Ile Ser Ala Asn Gly Lys Met Phe Gly Ser Ala Val Val Glu Asn Gly
    610                 615                 620

Thr Ala Thr Ile Asn Leu Thr Gly Leu Thr Asn Glu Ser Thr Leu Thr
625                 630                 635                 640

Leu Thr Val Val Gly Tyr Asn Lys Glu Thr Val Ile Lys Thr Ile Asn
                645                 650                 655

Thr Asn Gly Glu Pro Asn Pro Tyr Gln Pro Val Ser Asn Leu Thr Ala
            660                 665                 670

Thr Thr Gln Gly Gln Lys Val Thr Leu Lys Trp Asp Ala Pro Ser Thr
```

```
            675                 680                 685
Lys Thr Asn Ala Thr Asn Thr Ala Arg Ser Val Asp Gly Ile Arg
    690                 695                 700
Glu Leu Val Leu Leu Ser Val Ser Asp Ala Pro Glu Leu Leu Arg Ser
705                 710                 715                 720
Gly Gln Ala Glu Ile Val Leu Glu Ala His Asp Val Trp Asn Asp Gly
                725                 730                 735
Ser Gly Tyr Gln Ile Leu Leu Asp Ala Asp His Asp Gln Tyr Gly Gln
            740                 745                 750
Val Ile Pro Ser Asp Thr His Thr Leu Trp Pro Asn Cys Ser Val Pro
            755                 760                 765
Ala Asn Leu Phe Ala Pro Phe Glu Tyr Thr Val Pro Glu Asn Ala Asp
            770                 775                 780
Pro Ser Cys Ser Pro Thr Asn Met Ile Met Asp Gly Thr Ala Ser Val
785                 790                 795                 800
Asn Ile Pro Ala Gly Thr Tyr Asp Phe Ala Ile Ala Ala Pro Gln Ala
                805                 810                 815
Asn Ala Lys Ile Trp Ile Ala Gly Gln Gly Pro Thr Lys Glu Asp Asp
            820                 825                 830
Tyr Val Phe Glu Ala Gly Lys Lys Tyr His Phe Leu Met Lys Lys Met
            835                 840                 845
Gly Ser Gly Asp Gly Thr Glu Leu Thr Ile Ser Glu Gly Gly Gly Ser
850                 855                 860
Asp Tyr Thr Tyr Thr Val Tyr Arg Asp Gly Thr Lys Ile Lys Glu Gly
865                 870                 875                 880
Leu Thr Ala Thr Thr Phe Glu Glu Asp Gly Val Ala Ala Gly Asn His
                885                 890                 895
Glu Tyr Cys Val Glu Val Lys Tyr Thr Ala Gly Val Ser Pro Lys Val
                900                 905                 910
Cys Lys Asp Val Thr Val Glu Gly Ser Asn Glu Phe Ala Pro Val Gln
            915                 920                 925
Asn Leu Thr Gly Ser Ala Val Gly Gln Lys Val Thr Leu Lys Trp Asp
    930                 935                 940
Ala Pro Asn Gly Thr Pro Asn Pro Asn Pro Asn Pro Asn Pro Asn Pro
945                 950                 955                 960
Asn Pro Gly Thr Thr Thr Leu Ser Glu Ser Phe Glu Asn Gly Ile Pro
                965                 970                 975
Ala Ser Trp Lys Thr Ile Asp Ala Asp Gly Asp Gly His Gly Trp Lys
            980                 985                 990
Pro Gly Asn Ala Pro Gly Ile Ala Gly Tyr Asn Ser Asn Gly Cys Val
    995                 1000                1005
Tyr Ser Glu Ser Phe Gly Leu Gly Gly Ile Gly Val Leu Thr Pro
    1010                1015                1020
Asp Asn Tyr Leu Ile Thr Pro Ala Leu Asp Leu Pro Asn Gly Gly
    1025                1030                1035
Lys Leu Thr Phe Trp Val Cys Ala Gln Asp Ala Asn Tyr Ala Ser
    1040                1045                1050
Glu His Tyr Ala Val Tyr Ala Ser Ser Thr Gly Asn Asp Ala Ser
    1055                1060                1065
Asn Phe Thr Asn Ala Leu Leu Glu Glu Thr Ile Thr Ala Lys Gly
    1070                1075                1080
Val Arg Ser Pro Glu Ala Ile Arg Gly Arg Ile Gln Gly Thr Trp
    1085                1090                1095
```

```
Arg Gln Lys Thr Val Asp Leu Pro Ala Gly Thr Lys Tyr Val Ala
    1100            1105                1110

Phe Arg His Phe Gln Ser Thr Asp Met Phe Tyr Ile Asp Leu Asp
    1115            1120                1125

Glu Val Glu Ile Lys Ala Asn Gly Lys Arg Ala Asp Phe Thr Glu
    1130            1135                1140

Thr Phe Glu Ser Ser Thr His Gly Glu Ala Pro Ala Glu Trp Thr
    1145            1150                1155

Thr Ile Asp Ala Asp Gly Asp Gly Gln Gly Trp Leu Cys Leu Ser
    1160            1165                1170

Ser Gly Gln Leu Asp Trp Leu Thr Ala His Gly Gly Thr Asn Val
    1175            1180                1185

Val Ser Ser Phe Ser Trp Asn Gly Met Ala Leu Asn Pro Asp Asn
    1190            1195                1200

Tyr Leu Ile Ser Lys Asp Val Thr Gly Ala Thr Lys Val Lys Tyr
    1205            1210                1215

Tyr Tyr Ala Val Asn Asp Gly Phe Pro Gly Asp His Tyr Ala Val
    1220            1225                1230

Met Ile Ser Lys Thr Gly Thr Asn Ala Gly Asp Phe Thr Val Val
    1235            1240                1245

Phe Glu Glu Thr Pro Asn Gly Ile Asn Lys Gly Gly Ala Arg Phe
    1250            1255                1260

Gly Leu Ser Thr Glu Ala Asp Gly Ala Lys Pro Gln Ser Val Trp
    1265            1270                1275

Ile Glu Arg Thr Val Asp Leu Pro Ala Gly Thr Lys Tyr Val Ala
    1280            1285                1290

Phe Arg His Tyr Asn Cys Ser Asp Leu Asn Tyr Ile Leu Leu Asp
    1295            1300                1305

Asp Ile Gln Phe Thr Met Gly Gly Ser Pro Thr Pro Thr Asp Tyr
    1310            1315                1320

Thr Tyr Thr Val Tyr Arg Asp Gly Thr Lys Ile Lys Glu Gly Leu
    1325            1330                1335

Thr Glu Thr Thr Phe Glu Glu Asp Gly Val Ala Thr Gly Asn His
    1340            1345                1350

Glu Tyr Cys Val Glu Val Lys Tyr Thr Ala Gly Val Ser Pro Lys
    1355            1360                1365

Lys Cys Val Asn Val Thr Val Asn Ser Thr Gln Phe Asn Pro Val
    1370            1375                1380

Lys Asn Leu Lys Ala Gln Pro Asp Gly Gly Asp Val Val Leu Lys
    1385            1390                1395

Trp Glu Ala Pro Ser Ala Lys Lys Thr Glu Gly Ser Arg Glu Val
    1400            1405                1410

Lys Arg Ile Gly Asp Gly Leu Phe Val Thr Ile Glu Pro Ala Asn
    1415            1420                1425

Asp Val Arg Ala Asn Glu Ala Lys Val Val Leu Ala Ala Asp Asn
    1430            1435                1440

Val Trp Gly Asp Asn Thr Gly Tyr Gln Phe Leu Leu Asp Ala Asp
    1445            1450                1455

His Asn Thr Phe Gly Ser Val Ile Pro Ala Thr Gly Pro Leu Phe
    1460            1465                1470

Thr Gly Thr Ala Ser Ser Asp Leu Tyr Ser Ala Asn Phe Glu Tyr
    1475            1480                1485
```

```
Leu Ile Pro Ala Asn Ala Asp Pro Val Val Thr Thr Gln Asn Ile
    1490                1495                1500

Ile Val Thr Gly Gln Gly Glu Val Val Ile Pro Gly Gly Val Tyr
    1505                1510                1515

Asp Tyr Cys Ile Thr Asn Pro Glu Pro Ala Ser Gly Lys Met Trp
    1520                1525                1530

Ile Ala Gly Asp Gly Gly Asn Gln Pro Ala Arg Tyr Asp Asp Phe
    1535                1540                1545

Thr Phe Glu Ala Gly Lys Lys Tyr Thr Phe Thr Met Arg Arg Ala
    1550                1555                1560

Gly Met Gly Asp Gly Thr Asp Met Glu Val Glu Asp Asp Ser Pro
    1565                1570                1575

Ala Ser Tyr Thr Tyr Thr Val Tyr Arg Asp Gly Thr Lys Ile Lys
    1580                1585                1590

Glu Gly Leu Thr Glu Thr Thr Tyr Arg Asp Ala Gly Met Ser Ala
    1595                1600                1605

Gln Ser His Glu Tyr Cys Val Glu Val Lys Tyr Thr Ala Gly Val
    1610                1615                1620

Ser Pro Lys Val Cys Val Asp Tyr Ile Pro Asp Gly Val Ala Asp
    1625                1630                1635

Val Thr Ala Gln Lys Pro Tyr Thr Leu Thr Val Gly Lys Thr
    1640                1645                1650

Ile Thr Val Thr Cys Gln Gly Glu Ala Met Ile Tyr Asp Met Asn
    1655                1660                1665

Gly Arg Arg Leu Ala Ala Gly Arg Asn Thr Val Val Tyr Thr Ala
    1670                1675                1680

Gln Gly Gly Tyr Tyr Ala Val Met Val Val Asp Gly Lys Ser
    1685                1690                1695

Tyr Val Glu Lys Leu Ala Ile Lys
    1700                1705

<210> SEQ ID NO 76
<211> LENGTH: 484
<212> TYPE: PRT
<213> ORGANISM: Porphyromonas gingivalis

<400> SEQUENCE: 76

Met Lys Arg Lys Pro Leu Phe Ser Ala Leu Val Ile Leu Ser Gly Phe
1               5                   10                  15

Phe Gly Ser Val His Pro Ala Ser Ala Gln Lys Val Pro Ala Pro Val
            20                  25                  30

Asp Gly Glu Arg Ile Ile Met Glu Leu Ser Glu Ala Asp Val Glu Cys
        35                  40                  45

Thr Ile Lys Ile Glu Ala Glu Asp Gly Tyr Ala Asn Asp Ile Trp Ala
    50                  55                  60

Asp Leu Asn Gly Asn Gly Lys Tyr Asp Ser Gly Glu Arg Leu Asp Ser
65                  70                  75                  80

Gly Glu Phe Arg Asp Val Glu Phe Arg Gln Thr Lys Ala Ile Val Tyr
                85                  90                  95

Gly Lys Met Ala Lys Phe Leu Phe Arg Gly Ser Ser Ala Gly Asp Tyr
                100                 105                 110

Gly Ala Thr Phe Ile Asp Ile Ser Asn Cys Thr Gly Leu Thr Ala Phe
            115                 120                 125

Asp Cys Phe Ala Asn Leu Leu Thr Glu Leu Asp Leu Ser Lys Ala Asn
        130                 135                 140
```

-continued

Gly Leu Thr Phe Val Asn Cys Gly Lys Asn Gln Leu Thr Lys Leu Asp
145                 150                 155                 160

Leu Pro Ala Asn Ala Asp Ile Glu Thr Leu Asn Cys Ser Lys Asn Lys
                165                 170                 175

Ile Thr Ser Leu Asn Leu Ser Thr Tyr Thr Lys Leu Lys Glu Leu Tyr
            180                 185                 190

Val Gly Asp Asn Gly Leu Thr Ala Leu Asp Leu Ser Ala Asn Thr Leu
        195                 200                 205

Leu Glu Glu Leu Val Tyr Ser Asn Asn Glu Val Thr Thr Ile Asn Leu
210                 215                 220

Ser Ala Asn Thr Asn Leu Lys Ser Leu Tyr Cys Ile Asn Asn Lys Met
225                 230                 235                 240

Thr Gly Leu Asp Val Ala Ala Asn Lys Glu Leu Lys Ile Leu His Cys
                245                 250                 255

Asn Asn Asn Gln Leu Thr Ala Leu Asn Leu Ser Ala Asn Thr Lys Leu
            260                 265                 270

Thr Thr Leu Ser Phe Phe Asn Asn Glu Leu Thr Asn Ile Asp Leu Ser
        275                 280                 285

Asp Asn Thr Ala Leu Glu Trp Leu Phe Cys Asn Gly Asn Lys Leu Thr
290                 295                 300

Lys Leu Asp Val Ser Ala Asn Ala Asn Leu Ile Ala Leu Gln Cys Ser
305                 310                 315                 320

Asn Asn Gln Leu Thr Ala Leu Asp Leu Ser Lys Thr Pro Lys Leu Thr
                325                 330                 335

Thr Leu Asn Cys Tyr Ser Asn Arg Ile Lys Asp Thr Ala Met Arg Ala
            340                 345                 350

Leu Ile Glu Ser Leu Pro Thr Ile Thr Glu Gly Glu Gly Arg Phe Val
        355                 360                 365

Pro Tyr Asn Asp Asp Glu Gly Gly Glu Glu Asn Val Cys Thr Thr
370                 375                 380

Glu His Val Glu Met Ala Lys Ala Lys Asn Trp Lys Val Leu Thr Ser
385                 390                 395                 400

Trp Gly Glu Pro Phe Pro Gly Ile Thr Ala Leu Ile Ser Ile Glu Gly
                405                 410                 415

Glu Ser Glu Tyr Ser Val Tyr Ala Gln Asp Gly Ile Leu Tyr Leu Ser
            420                 425                 430

Gly Met Glu Gln Gly Leu Pro Val Gln Val Tyr Thr Val Gly Gly Ser
        435                 440                 445

Met Met Tyr Ser Ser Val Ala Ser Gly Ser Ala Met Glu Ile Gln Leu
450                 455                 460

Pro Arg Gly Ala Ala Tyr Val Val Arg Ile Gly Ser His Ala Ile Lys
465                 470                 475                 480

Thr Ala Met Pro

<210> SEQ ID NO 77
<211> LENGTH: 2105
<212> TYPE: PRT
<213> ORGANISM: Porphyromonas gingivalis

<400> SEQUENCE: 77

Met Ala Arg Ile Ile Leu Glu Ala His Asp Val Trp Glu Asp Gly Thr
1               5                   10                  15

Gly Tyr Gln Met Leu Trp Asp Ala Asp His Asn Gln Tyr Gly Ala Ser
            20                  25                  30

```
Ile Pro Glu Glu Ser Phe Trp Phe Ala Asn Gly Thr Ile Pro Ala Gly
         35                  40                  45

Leu Tyr Asp Pro Phe Glu Tyr Lys Val Pro Val Asn Ala Asp Ala Ser
 50                  55                  60

Phe Ser Pro Thr Asn Phe Val Leu Asp Gly Thr Ala Ser Ala Asp Ile
 65                  70                  75                  80

Pro Ala Gly Thr Tyr Asp Tyr Val Ile Ile Asn Pro Asn Pro Gly Ile
                 85                  90                  95

Ile Tyr Ile Val Gly Glu Gly Val Ser Lys Gly Asn Asp Tyr Val Val
                100                 105                 110

Glu Ala Gly Lys Thr Tyr His Phe Thr Val Gln Arg Gln Gly Pro Gly
                115                 120                 125

Asp Ala Ala Ser Val Val Val Thr Gly Glu Gly Gly Asn Glu Phe Ala
        130                 135                 140

Pro Val Gln Asn Leu Gln Trp Ser Val Ser Gly Gln Thr Val Thr Leu
145                 150                 155                 160

Thr Trp Gln Ala Pro Ala Ser Asp Lys Arg Thr Tyr Val Leu Asn Glu
                165                 170                 175

Ser Phe Asp Thr Gln Thr Leu Pro Asn Gly Trp Thr Met Ile Asp Ala
                180                 185                 190

Asp Gly Asp Gly His Asn Trp Leu Ser Thr Ile Asn Val Tyr Asn Thr
        195                 200                 205

Ala Thr His Thr Gly Asp Gly Ala Met Phe Ser Lys Ser Trp Thr Ala
        210                 215                 220

Ser Ser Gly Ala Lys Ile Asp Leu Ser Pro Asp Asn Tyr Leu Val Thr
225                 230                 235                 240

Pro Lys Phe Thr Val Pro Glu Asn Gly Lys Leu Ser Tyr Trp Val Ser
                245                 250                 255

Ser Gln Glu Pro Trp Thr Asn Glu His Tyr Gly Val Phe Leu Ser Thr
                260                 265                 270

Thr Gly Asn Glu Ala Ala Asn Phe Thr Ile Lys Leu Leu Glu Glu Thr
        275                 280                 285

Leu Gly Ser Gly Lys Pro Ala Pro Met Asn Leu Val Lys Ser Glu Gly
        290                 295                 300

Val Lys Ala Pro Ala Pro Tyr Gln Glu Arg Thr Ile Asp Leu Ser Ala
305                 310                 315                 320

Tyr Ala Gly Gln Gln Val Tyr Leu Ala Phe Arg His Phe Gly Cys Thr
                325                 330                 335

Gly Ile Phe Arg Leu Tyr Leu Asp Asp Val Ala Val Ser Gly Glu Gly
                340                 345                 350

Ser Ser Asn Asp Tyr Thr Tyr Thr Val Tyr Arg Asp Asn Val Val Ile
        355                 360                 365

Ala Gln Asn Leu Thr Ala Thr Thr Phe Asn Gln Glu Asn Val Ala Pro
370                 375                 380

Gly Gln Tyr Asn Tyr Cys Val Glu Val Lys Tyr Thr Ala Gly Val Ser
385                 390                 395                 400

Pro Lys Val Cys Lys Asp Val Thr Val Glu Gly Ser Asn Glu Phe Ala
                405                 410                 415

Pro Val Gln Asn Leu Thr Gly Ser Ala Val Gly Gln Lys Val Thr Leu
                420                 425                 430

Lys Trp Asp Ala Pro Asn Gly Thr Pro Asn Pro Asn Pro Gly Thr Thr
                435                 440                 445
```

-continued

```
Thr Leu Ser Glu Ser Phe Glu Asn Gly Ile Pro Ala Ser Trp Lys Thr
450                 455                 460

Ile Asp Ala Asp Gly Asp Gly Asn Asn Trp Thr Thr Pro Pro Pro
465                 470                 475                 480

Gly Gly Ser Ser Phe Ala Gly His Asn Ser Ala Ile Cys Val Ser Ser
                    485                 490                 495

Ala Ser Tyr Ile Asn Phe Glu Gly Pro Gln Asn Pro Asp Asn Tyr Leu
                500                 505                 510

Val Thr Pro Glu Leu Ser Leu Pro Asn Gly Gly Thr Leu Thr Phe Trp
                515                 520                 525

Val Cys Ala Gln Asp Ala Asn Tyr Ala Ser Glu His Tyr Ala Val Tyr
530                 535                 540

Ala Ser Ser Thr Gly Asn Asp Ala Ser Asn Phe Ala Asn Ala Leu Leu
545                 550                 555                 560

Glu Glu Val Leu Thr Ala Lys Thr Val Val Thr Ala Pro Glu Ala Ile
                565                 570                 575

Arg Gly Thr Arg Val Gln Gly Thr Trp Tyr Gln Lys Thr Val Gln Leu
                580                 585                 590

Pro Ala Gly Thr Lys Tyr Val Ala Phe Arg His Phe Gly Cys Thr Asp
                595                 600                 605

Phe Phe Trp Ile Asn Leu Asp Asp Val Glu Ile Lys Ala Asn Gly Lys
610                 615                 620

Arg Ala Asp Phe Thr Glu Thr Phe Glu Ser Ser Thr His Gly Glu Ala
625                 630                 635                 640

Pro Ala Glu Trp Thr Thr Ile Asp Ala Asp Gly Asp Gly Gln Gly Trp
                645                 650                 655

Leu Cys Leu Ser Ser Gly Gln Leu Gly Trp Leu Thr Ala His Gly Gly
                660                 665                 670

Thr Asn Val Val Ala Ser Phe Ser Trp Asn Gly Met Ala Leu Asn Pro
            675                 680                 685

Asp Asn Tyr Leu Ile Ser Lys Asp Val Thr Gly Ala Thr Lys Val Lys
            690                 695                 700

Tyr Tyr Tyr Ala Val Asn Asp Gly Phe Pro Gly Asp His Tyr Ala Val
705                 710                 715                 720

Met Ile Ser Lys Thr Gly Thr Asn Ala Gly Asp Phe Thr Val Val Phe
                725                 730                 735

Glu Glu Thr Pro Asn Gly Ile Asn Lys Gly Gly Ala Arg Phe Gly Leu
                740                 745                 750

Ser Thr Glu Ala Asn Gly Ala Lys Pro Gln Ser Val Trp Ile Glu Arg
                755                 760                 765

Thr Val Asp Leu Pro Ala Gly Thr Lys Tyr Val Ala Phe Arg His Tyr
770                 775                 780

Asn Cys Ser Asp Leu Asn Tyr Ile Leu Leu Asp Asp Ile Gln Phe Thr
785                 790                 795                 800

Met Gly Gly Ser Pro Thr Pro Thr Asp Tyr Thr Tyr Thr Val Tyr Arg
                805                 810                 815

Asp Gly Thr Lys Ile Lys Glu Gly Leu Thr Glu Thr Phe Glu Glu
                820                 825                 830

Asp Gly Val Ala Thr Gly Asn His Glu Tyr Cys Val Glu Val Lys Tyr
                835                 840                 845

Thr Ala Gly Val Ser Pro Lys Glu Cys Val Asn Val Thr Val Asp Pro
850                 855                 860

Val Gln Phe Asn Pro Val Gln Asn Leu Thr Gly Ser Ala Val Gly Gln
```

```
                865                 870                 875                 880
Lys Val Thr Leu Lys Trp Asp Ala Pro Asn Gly Thr Pro Asn Pro Asn
                    885                 890                 895

Pro Gly Thr Thr Thr Leu Ser Glu Ser Phe Glu Asn Gly Ile Pro Ala
                900                 905                 910

Ser Trp Lys Thr Ile Asp Ala Asp Gly Asp Gly Asn Asn Trp Thr Thr
            915                 920                 925

Thr Pro Pro Gly Gly Thr Ser Phe Ala Gly His Asn Ser Ala Ile
        930                 935                 940

Cys Val Ser Ser Ala Ser Tyr Ile Asn Phe Glu Gly Pro Gln Asn Pro
945                 950                 955                 960

Asp Asn Tyr Leu Val Thr Pro Glu Leu Ser Leu Pro Asn Gly Thr
                965                 970                 975

Leu Thr Phe Trp Val Cys Ala Gln Asp Ala Asn Tyr Ala Ser Glu His
                    980                 985                 990

Tyr Ala Val Tyr Ala Ser Ser Thr Gly Asn Asp Ala Ser Asn Phe Ala
                995                 1000                1005

Asn Ala Leu Leu Glu Glu Val Leu Thr Ala Lys Thr Val Val Thr
        1010                1015                1020

Ala Pro Glu Ala Ile Arg Gly Thr Arg Val Gln Gly Thr Trp Tyr
        1025                1030                1035

Gln Lys Thr Val Gln Leu Pro Ala Gly Thr Lys Tyr Val Ala Phe
        1040                1045                1050

Arg His Phe Gly Cys Thr Asp Phe Phe Trp Ile Asn Leu Asp Asp
        1055                1060                1065

Val Glu Ile Lys Ala Asn Gly Lys Arg Ala Asp Phe Thr Glu Thr
        1070                1075                1080

Phe Glu Ser Ser Thr His Gly Glu Ala Pro Ala Glu Trp Thr Thr
        1085                1090                1095

Ile Asp Ala Asp Gly Asp Gln Gly Trp Leu Cys Leu Ser Ser
        1100                1105                1110

Gly Gln Leu Asp Trp Leu Thr Ala His Gly Gly Thr Asn Val Val
        1115                1120                1125

Ala Ser Phe Ser Trp Asn Gly Met Ala Leu Asn Pro Asp Asn Tyr
        1130                1135                1140

Leu Ile Ser Lys Asp Val Thr Gly Ala Thr Lys Val Lys Tyr Tyr
        1145                1150                1155

Tyr Ala Val Asn Asp Gly Phe Pro Gly Asp His Tyr Ala Val Met
        1160                1165                1170

Ile Ser Lys Thr Gly Thr Asn Ala Gly Asp Phe Thr Val Val Phe
        1175                1180                1185

Glu Glu Thr Pro Asn Gly Ile Asn Lys Gly Gly Ala Arg Phe Gly
        1190                1195                1200

Leu Ser Thr Glu Ala Asn Gly Ala Lys Pro Gln Ser Val Trp Ile
        1205                1210                1215

Glu Arg Thr Val Asp Leu Pro Ala Gly Thr Lys Tyr Val Ala Phe
        1220                1225                1230

Arg His Tyr Asn Cys Ser Asp Leu Asn Tyr Ile Leu Leu Asp Asp
        1235                1240                1245

Ile Gln Phe Thr Met Gly Gly Ser Pro Thr Pro Thr Asp Tyr Thr
        1250                1255                1260

Tyr Thr Val Tyr Arg Asp Gly Thr Lys Ile Lys Glu Gly Leu Thr
        1265                1270                1275
```

-continued

```
Glu Thr Thr Phe Glu Glu Asp Gly Val Ala Thr Gly Asn His Glu
    1280                1285                1290

Tyr Cys Val Glu Val Lys Tyr Thr Ala Gly Val Ser Pro Lys Glu
    1295                1300                1305

Cys Val Asn Val Thr Val Asp Pro Val Gln Phe Asn Pro Val Gln
    1310                1315                1320

Asn Leu Thr Gly Ser Ala Val Gly Gln Lys Val Thr Leu Lys Trp
    1325                1330                1335

Asp Ala Pro Asn Gly Thr Pro Asn Pro Asn Pro Gly Thr Thr Thr
    1340                1345                1350

Leu Ser Glu Ser Phe Glu Asn Gly Ile Pro Ala Ser Trp Lys Thr
    1355                1360                1365

Ile Asp Ala Asp Gly Asp Gly Asn Asn Trp Thr Thr Thr Pro Pro
    1370                1375                1380

Pro Gly Gly Thr Ser Phe Ala Gly His Asn Ser Ala Ile Cys Val
    1385                1390                1395

Ser Ser Ala Ser Tyr Ile Asn Phe Glu Gly Pro Gln Asn Pro Asp
    1400                1405                1410

Asn Tyr Leu Val Thr Pro Glu Leu Ser Leu Pro Asn Gly Gly Thr
    1415                1420                1425

Leu Thr Phe Trp Val Cys Ala Gln Asp Ala Asn Tyr Ala Ser Glu
    1430                1435                1440

His Tyr Ala Val Tyr Ala Ser Ser Thr Gly Asn Asp Ala Ser Asn
    1445                1450                1455

Phe Ala Asn Ala Leu Leu Glu Glu Val Leu Thr Ala Lys Thr Val
    1460                1465                1470

Val Thr Ala Pro Glu Ala Ile Arg Gly Thr Arg Val Gln Gly Thr
    1475                1480                1485

Trp Tyr Gln Lys Thr Val Gln Leu Pro Ala Gly Thr Lys Tyr Val
    1490                1495                1500

Ala Phe Arg His Phe Gly Cys Thr Asp Phe Phe Trp Ile Asn Leu
    1505                1510                1515

Asp Asp Val Glu Ile Lys Ala Asn Gly Lys Arg Ala Asp Phe Thr
    1520                1525                1530

Glu Thr Phe Glu Ser Ser Thr His Gly Glu Ala Pro Ala Glu Trp
    1535                1540                1545

Thr Thr Ile Asp Ala Asp Gly Asp Gly Gln Gly Trp Leu Cys Leu
    1550                1555                1560

Ser Ser Gly Gln Leu Gly Trp Leu Thr Ala His Gly Gly Thr Asn
    1565                1570                1575

Val Val Ala Ser Phe Ser Trp Asn Gly Met Ala Leu Asn Pro Asp
    1580                1585                1590

Asn Tyr Leu Ile Ser Lys Asp Val Thr Gly Ala Thr Lys Val Lys
    1595                1600                1605

Tyr Tyr Tyr Ala Val Asn Asp Gly Phe Pro Gly Asp His Tyr Ala
    1610                1615                1620

Val Met Ile Ser Lys Thr Gly Thr Asn Ala Gly Asp Phe Thr Val
    1625                1630                1635

Val Phe Glu Glu Thr Pro Asn Gly Ile Asn Lys Gly Gly Ala Arg
    1640                1645                1650

Phe Gly Leu Ser Thr Glu Ala Asn Gly Ala Lys Pro Gln Ser Val
    1655                1660                1665
```

```
Trp Ile Glu Arg Thr Val Asp Leu Pro Ala Gly Thr Lys Tyr Val
1670                1675                1680

Ala Phe Arg His Tyr Asn Cys Ser Asp Leu Asn Tyr Ile Leu Leu
1685                1690                1695

Asp Asp Ile Gln Phe Thr Met Gly Gly Ser Pro Thr Pro Thr Asp
1700                1705                1710

Tyr Thr Tyr Thr Val Tyr Arg Asp Gly Thr Lys Ile Lys Glu Gly
1715                1720                1725

Leu Thr Glu Thr Thr Phe Glu Glu Asp Gly Val Ala Thr Gly Asn
1730                1735                1740

His Glu Tyr Cys Val Glu Val Lys Tyr Thr Ala Gly Val Ser Pro
1745                1750                1755

Lys Glu Cys Val Asn Val Thr Ile Asn Pro Thr Gln Phe Asn Pro
1760                1765                1770

Val Gln Asn Leu Thr Ala Glu Gln Ala Pro Asn Ser Met Asp Ala
1775                1780                1785

Ile Leu Lys Trp Asn Ala Pro Ala Ser Lys Arg Ala Glu Val Leu
1790                1795                1800

Asn Glu Asp Phe Glu Asn Gly Ile Pro Ala Ser Trp Lys Thr Ile
1805                1810                1815

Asp Ala Asp Gly Asp Gly Asn Asn Trp Thr Thr Thr Pro Pro Pro
1820                1825                1830

Gly Gly Ser Ser Phe Ala Gly His Asn Ser Ala Ile Cys Val Ser
1835                1840                1845

Ser Ala Ser Tyr Ile Asn Phe Glu Gly Pro Gln Asn Pro Asp Asn
1850                1855                1860

Tyr Leu Val Thr Pro Glu Leu Ser Leu Pro Gly Gly Gly Thr Leu
1865                1870                1875

Thr Phe Trp Val Cys Ala Gln Asp Ala Asn Tyr Ala Ser Glu His
1880                1885                1890

Tyr Ala Val Tyr Ala Ser Ser Thr Gly Asn Asp Ala Ser Asn Phe
1895                1900                1905

Ala Asn Ala Leu Leu Glu Glu Val Leu Thr Ala Lys Thr Val Val
1910                1915                1920

Thr Ala Pro Glu Ala Ile Arg Gly Thr Arg Val Gln Gly Thr Trp
1925                1930                1935

Tyr Gln Lys Thr Val Gln Leu Pro Ala Gly Thr Lys Tyr Val Ala
1940                1945                1950

Phe Arg His Phe Gly Cys Thr Asp Phe Phe Trp Ile Asn Leu Asp
1955                1960                1965

Asp Val Val Ile Thr Ser Gly Asn Ala Pro Ser Tyr Thr Tyr Thr
1970                1975                1980

Ile Tyr Arg Asn Asn Thr Gln Ile Ala Ser Gly Val Thr Glu Thr
1985                1990                1995

Thr Tyr Arg Asp Pro Asp Leu Ala Thr Gly Phe Tyr Thr Tyr Gly
2000                2005                2010

Val Lys Val Val Tyr Pro Asn Gly Glu Ser Ala Ile Glu Thr Ala
2015                2020                2025

Thr Leu Asn Ile Thr Ser Leu Ala Asp Val Thr Ala Gln Lys Pro
2030                2035                2040

Tyr Thr Leu Thr Val Val Gly Lys Thr Ile Thr Val Thr Cys Gln
2045                2050                2055

Gly Glu Ala Met Ile Tyr Asp Met Asn Gly Arg Arg Leu Ala Ala
```

```
                    2060               2065               2070
Gly Arg Asn Thr Val Val Tyr Thr Ala Gln Gly Gly His Tyr Ala
    2075               2080               2085

Val Met Val Val Val Asp Gly Lys Ser Tyr Val Glu Lys Leu Ala
    2090               2095               2100

Val Lys
    2105

<210> SEQ ID NO 78
<211> LENGTH: 405
<212> TYPE: PRT
<213> ORGANISM: Porphyromonas gingivalis

<400> SEQUENCE: 78

Met Lys Lys Thr Thr Ile Ile Ser Leu Ile Val Phe Gly Ala Phe Phe
1               5                   10                  15

Ala Ala Val Gly Gln Thr Lys Asp Asn Ser Ser Tyr Lys Pro Phe Ser
                20                  25                  30

Lys Glu Asp Ile Ala Gly Gly Val Tyr Ser Leu Pro Thr Gln Asn Arg
            35                  40                  45

Ala Gln Lys Asp Asn Ala Glu Trp Leu Leu Thr Ala Thr Val Ser Thr
        50                  55                  60

Asn Gln Ser Ala Asp Thr His Phe Ile Phe Asp Glu Asn Asn Arg Tyr
65                  70                  75                  80

Ile Ala Arg Asp Ile Lys Ala Asn Gly Val Arg Lys Ser Thr Asp Ser
                85                  90                  95

Ile Tyr Tyr Asp Ala Asn Gly Arg Ile Ser His Val Asp Leu Tyr Ile
            100                 105                 110

Ser Phe Ser Gly Gly Glu Pro Ala Leu Asp Thr Arg Phe Lys Tyr Thr
        115                 120                 125

Tyr Asp Asp Glu Gly Lys Met Thr Val Arg Glu Val Phe Met Leu Val
    130                 135                 140

Met Asp Pro Asn Thr Pro Ile Ser Arg Leu Glu Tyr His Tyr Asp Ala
145                 150                 155                 160

Gln Gly Arg Leu Thr His Trp Ile Ser Phe Ala Phe Gly Ala Glu Ser
                165                 170                 175

Gln Lys Asn Thr Tyr His Tyr Asn Glu Lys Gly Leu Leu Val Ser Glu
            180                 185                 190

Val Leu Ser Asn Ala Met Gly Thr Thr Tyr Ser Asp Thr Gly Lys Thr
        195                 200                 205

Glu Tyr Ser Tyr Asp Asp Ala Asp Asn Met Val Lys Ala Glu Tyr Phe
    210                 215                 220

Val Val Gln Gln Gly Lys Ala Trp Gln Val Leu Lys Arg Glu Glu Tyr
225                 230                 235                 240

Thr Tyr Glu Asp Asn Ile Cys Ile Gln Tyr Leu Ala Ile Asn Gly Thr
                245                 250                 255

Asp Thr Lys Val Tyr Lys Arg Asp Ile Glu Ser Asp Lys Ser Ile Ser
            260                 265                 270

Ala Asn Val Ile Asp Ile Pro Ser Met Pro Glu Gln Thr Trp Pro Asn
        275                 280                 285

Met Tyr Gly Phe Asn Ala Lys Arg Leu Lys Glu Thr Tyr Ser Ser Tyr
    290                 295                 300

Glu Gly Asp Val Ala Thr Pro Ile Phe Asp Tyr Ile Tyr Thr Tyr Lys
305                 310                 315                 320
```

```
Ala Leu Thr Ser Met Ala Thr Pro Ser Thr Glu Ala Gln Val Ala Val
            325                 330                 335

Tyr Leu Asn Pro Ser Thr Asp Arg Leu Val Ile Leu Ala Asn Gly Ile
            340                 345                 350

Thr His Leu Ser Met Tyr Asp Leu Gln Gly Lys Leu Ile Arg Asp Cys
            355                 360                 365

Ala Leu Ser Gly Asp Lys Val Glu Met Gly Val Gly Ser Leu Thr Lys
            370                 375                 380

Gly Thr Tyr Leu Leu Lys Val Asn Thr Asp Gln Gly Ala Phe Val Arg
385                 390                 395                 400

Lys Val Val Ile Arg
            405

<210> SEQ ID NO 79
<211> LENGTH: 871
<212> TYPE: PRT
<213> ORGANISM: Porphyromonas gingivalis

<400> SEQUENCE: 79

Met Leu Cys Leu Met Arg Lys Arg Ile Leu Gln Leu Phe Leu Thr Ala
1               5                   10                  15

Leu Leu Leu Ala Leu Gly Ser Ser Leu Ala Ile Ala Gln Thr Val Val
            20                  25                  30

Thr Gly Lys Val Ile Asp Ser Glu Thr Ser Glu Pro Leu Ile Gly Val
            35                  40                  45

Ser Val Ser Thr Gly Gln Gly Ala Ser Leu Arg Gly Val Thr Thr Asp
            50                  55                  60

Met Asp Gly Gly Phe Arg Phe Glu Val Pro Ala Lys Ser Val Leu Thr
65              70                  75                  80

Phe Arg Cys Val Gly Tyr Ala Thr Val Thr Arg Ser Ile Gly Arg Gly
            85                  90                  95

Ser Gln Glu Asp Leu Gly Thr Ile Leu Leu Asp Pro Gln Ala Ile Gly
            100                 105                 110

Leu Asp Glu Ile Gln Val Ile Ala Ser Val Val Pro Lys Asp Arg Met
            115                 120                 125

Thr Pro Val Pro Val Ser Asn Ile Arg Val Ala Asp Ile Gln Ala Ala
            130                 135                 140

Ser Leu Asn Val Glu Phe Pro Glu Leu Val Lys Ser Thr Pro Ser Thr
145                 150                 155                 160

Tyr Thr Thr Lys Gly Ser Gly Phe Gly Asp Gly Arg Thr Asn Val
            165                 170                 175

Arg Gly Phe Asp Thr Tyr Asn Phe Gly Val Leu Ile Asn Gly Val Pro
            180                 185                 190

Val Asn Gly Met Glu Asp Gly Lys Val Tyr Trp Ser Asn Trp Ser Gly
            195                 200                 205

Leu Met Asn Gln Ala Ser Thr Ile Gln Ile Gln Arg Gly Leu Gly Ala
            210                 215                 220

Ser Lys Leu Gly Ile Ser Ser Val Gly Gly Thr Met Asn Ile Thr
225                 230                 235                 240

Lys Thr Thr Asp Ala Asn Thr Gly Gly Ser Ala Tyr Val Gly Met Gly
            245                 250                 255

Asn Asp Gly Leu His Lys Glu Ser Phe Ser Ile Ser Thr Gly Met Asn
            260                 265                 270

Asp Gly Trp Ala Ile Thr Ile Ala Gly Ser His Met Thr Gly Leu Gly
            275                 280                 285
```

```
Tyr Val Lys Gly Leu Lys Gly Arg Ala Phe Ser Tyr Phe Asn Val
    290             295             300
Ser Lys Lys Phe Asn Glu Arg His Thr Leu Ser Leu Thr Gly Phe Gly
305             310             315             320
Ala Pro Gln Trp His Asn Gln Arg Ser Ser Lys Tyr Ser Val Ala Asp
                325             330             335
Tyr Asp Lys Tyr Gly Ile Arg His Asn Gln Ser Phe Gly Tyr Leu Arg
            340             345             350
Gly Glu Leu Thr Pro Thr Ala Tyr Ala Tyr Asn Thr Tyr His Lys Pro
        355             360             365
Gln Phe Ser Leu Asn His Phe Trp Lys Met Asp Glu Asn Thr Ser Leu
    370             375             380
Tyr Thr Ala Ala Tyr Ala Ser Leu Ala Thr Gly Gly Arg Arg Ala
385             390             395             400
Tyr Gly Lys Asn Ser Lys Trp Val Leu Ile Asn Tyr Asn Thr Gly Gln
                405             410             415
Pro Tyr Glu Gln Thr Lys Val Thr Pro Asp Gly Leu Ile Asp Tyr Asp
            420             425             430
Ala Val Leu Ala Ala Asn Ala Ala Ser Asn Gly Ser Glu Ala Ile
        435             440             445
Phe Ala Leu Gly Ser Asn Ser His Lys Trp Phe Gly Leu Leu Ser Ser
    450             455             460
Phe Lys Lys Lys Leu Asn Ser Ser Leu Thr Leu Thr Ala Gly Tyr Asp
465             470             475             480
Gly Arg Tyr Tyr Arg Gly Asp His Tyr Asp Lys Ile Thr Asp Leu Leu
                485             490             495
Gly Gly Ser Tyr Tyr Ile Glu Asp Pro Lys Thr Lys Leu Ala Tyr His
            500             505             510
Ala Glu Gly Gln Gln Leu Lys Val Gly Asp Ile Val Asn Arg Asp Tyr
        515             520             525
Thr Gly Glu Ile Met Trp His Gly Leu Phe Ala Gln Met Glu His Ser
    530             535             540
Ser Glu Trp Ile Asp Ala Phe Val Ser Gly Ser Ile Asn Tyr Glu Leu
545             550             555             560
Tyr Arg Asn His Asn Tyr Gly Gly Ser Lys Ser Thr Gly Tyr Leu Pro
                565             570             575
Gly Val Ser Pro Trp Lys Ser Phe Leu Pro Trp Ser Gly Lys Ala Gly
            580             585             590
Leu Ser Tyr Lys Phe Ala Gln Gly His Asn Val Phe Ala Asn Gly Gly
        595             600             605
Phe Phe Thr Arg Ala Pro Leu Phe Gly Asn Ile Tyr Ala Ala Gly Ala
    610             615             620
Ile Ile Pro Asn Asp Lys Ala Asn Met Glu Lys Val Leu Thr Gly Glu
625             630             635             640
Val Gly Tyr Gly Phe Thr Asn His Lys Asn Phe Glu Phe Asn Ile Asn
                645             650             655
Gly Tyr Tyr Thr Lys Trp Met Asp Arg Val Thr Ser Lys Arg Ile Gly
            660             665             670
Asn Glu Tyr Val Tyr Leu Asn Gly Val Asp Ala Val His Cys Gly Val
        675             680             685
Glu Ala Glu Val Ser Tyr Arg Pro Ile Arg Gln Ile Asp Leu Arg Gly
    690             695             700
```

Met Phe Ser Leu Gly Asp Trp Thr Trp Gln Asn Asn Val Ser Tyr Thr
705                 710                 715                 720

Ser Tyr Asp Glu Ala Gly Asn Glu Thr Gly Gln Asp Ile Thr Tyr Ile
            725                 730                 735

Lys Gly Leu His Val Gly Asp Ala Ala Gln Met Thr Ala Ala Val Ser
        740                 745                 750

Ala Asp Ile Glu Leu Phe Lys Gly Phe His Val Ile Gly Lys Tyr Asn
        755                 760                 765

Phe Leu Gly Lys Asn Tyr Ala Gly Phe Asn Pro Ala Thr Arg Asn Ala
770                 775                 780

Gln Gln Tyr Glu Ala Asp Gly Lys Glu Ile Val Glu Ser Trp Lys Leu
785                 790                 795                 800

Pro Asp Val Gly Leu Phe Asp Leu Ser Ala Ser Tyr Asn Phe Lys Leu
            805                 810                 815

Gly Ser Leu Ser Thr Thr Phe Tyr Phe Asn Met Asp Asn Val Ala Asp
            820                 825                 830

Lys Arg Tyr Val Ser Asp Ala Asp Asn Ile Ile Gly Lys Lys His
        835                 840                 845

Asp Glu Ala Ser Ala Leu Val Trp Tyr Gly Phe Gly Arg Thr Trp Ser
850                 855                 860

Thr Gly Ile Arg Val Asn Phe
865                 870

<210> SEQ ID NO 80
<211> LENGTH: 142
<212> TYPE: PRT
<213> ORGANISM: Porphyromonas gingivalis

<400> SEQUENCE: 80

Met Ala Leu His Arg Tyr Asp Val Arg Leu Asn Cys Gly Glu Ser Gly
1               5                   10                  15

Lys Gly Lys Gly Gly Ala Val Phe Ser Gly Lys Thr Glu Met Asp Gln
            20                  25                  30

Ala Thr Thr Val Pro Thr Asp Gly Tyr Thr Val Asp Val Leu Gly Arg
        35                  40                  45

Ile Thr Val Lys Tyr Glu Met Gly Pro Asp Gly His Gln Met Glu Tyr
    50                  55                  60

Glu Glu Gln Gly Phe Ser Glu Val Ile Thr Gly Lys Lys Asn Ala Gln
65                  70                  75                  80

Gly Phe Ala Ser Gly Gly Trp Leu Glu Phe Ser His Gly Pro Ala Gly
                85                  90                  95

Pro Thr Tyr Lys Leu Ser Lys Arg Val Phe Val Arg Gly Ala Asp
            100                 105                 110

Gly Asn Ile Ala Lys Val Gln Phe Thr Asp Tyr Gln Asp Ala Glu Leu
        115                 120                 125

Lys Lys Gly Val Ile Thr Phe Thr Tyr Thr Tyr Pro Val Lys
    130                 135                 140

<210> SEQ ID NO 81
<211> LENGTH: 833
<212> TYPE: PRT
<213> ORGANISM: Porphyromonas gingivalis

<400> SEQUENCE: 81

Met Lys Gln Leu Asn Ile Ile Ser Phe Ile Ile Ala Phe Leu Phe Leu
1               5                   10                  15

```
Gly Thr Ser Ala Ser Ala Gln Gln Ser Gly Gly Ser Val Thr Gly Thr
            20                  25                  30

Val Val Asp Lys Ser Ser Lys Glu Pro Ile Ala Tyr Val Gln Val Phe
        35                  40                  45

Val Lys Gly Thr Thr Leu Gly Thr Ser Thr Asp Ala Asn Gly Asn Tyr
    50                  55                  60

Ser Ile Lys Gly Ile Pro Ser Gly Asn Gln Thr Ile Val Ala Arg Leu
65                  70                  75                  80

Met Gly Tyr Ser Thr Cys Glu Glu Lys Val His Ile Glu Lys Gly Gly
                85                  90                  95

Ser Arg His Val Asp Leu Tyr Leu Thr Glu Glu Ile Leu Ser Leu Asp
            100                 105                 110

Gly Val Val Ser Ala Asn Arg Asn Glu Thr Phe Arg Arg Gln Ala
        115                 120                 125

Pro Ser Leu Val Thr Val Leu Ser Pro Glu Leu Phe Leu Lys Thr Asn
    130                 135                 140

Ser Thr Asn Leu Ser Gln Gly Leu Lys Phe Gln Pro Gly Leu Arg Val
145                 150                 155                 160

Glu Asp Asn Cys Gln Asn Cys Gly Phe Asn Gln Val Arg Ile Asn Gly
                165                 170                 175

Leu Glu Gly Ala Tyr Ser Gln Ile Leu Ile Asp Ser His Pro Ile Phe
            180                 185                 190

Ser Ser Leu Ala Gly Val Tyr Gly Leu Glu Gln Met Pro Ala Asn Met
        195                 200                 205

Ile Glu Arg Val Glu Val Ile Arg Gly Gly Ser Ala Leu Phe Gly
    210                 215                 220

Ser Asn Ala Val Gly Gly Val Ile Asn Val Ile Thr Lys Glu Pro Leu
225                 230                 235                 240

Arg Asn Ser Ala Glu Ile Ser His Ser Thr Met Thr Phe Asp His Ala
                245                 250                 255

Lys Gly Trp Gly Ser Phe Gln Asn Thr Thr Gln Phe Asn Gly Ser Met
            260                 265                 270

Leu Thr Glu Asp Arg Lys Ala Gly Val Met Val Phe Gly Gln His Asn
        275                 280                 285

Tyr Arg Pro Gly Gln Asp Ile Asp Gly Asp Asn Phe Thr Glu Leu Pro
    290                 295                 300

Asn Leu Arg Asn Arg Ser Leu Gly Phe Arg Ser Tyr Tyr Lys Thr Gly
305                 310                 315                 320

Leu Tyr Ser Lys Ala Thr Leu Glu Tyr His Ser Met Gln Glu Tyr Arg
                325                 330                 335

Arg Gly Gly Asp Arg Leu Asp Asn Pro Pro Phe Glu Ala Gln Ile Ala
            340                 345                 350

Glu Tyr Leu Gln His Tyr Ile Asn Gly Gly Ser Phe Lys Phe Asp Gln
        355                 360                 365

Gly Phe Ser Gly Gly Lys Asp Phe Phe Ser Leu Tyr Ala Ser Ala Gln
    370                 375                 380

Asp Val Gln Arg Arg Ser Tyr Tyr Gly Gly Gly Asp Tyr Thr Glu Asn
385                 390                 395                 400

Leu Leu Asn Gly Ala Val Gln Ser Gly Ser Thr Glu Ser Asp Glu Tyr
                405                 410                 415

Asn Asp Ala Phe Thr Ala Leu Thr Ser Tyr Gly Thr Thr Lys Gly Phe
            420                 425                 430

Asp Leu Gln Gly Gly Gly Met Tyr Arg His Thr Phe Gly Glu Asn Trp
```

```
              435                 440                 445
Asp Phe Thr Gly Gly Leu Glu Tyr Ile Tyr Gly Gln Leu Asp Asp Arg
450                 455                 460
Ser Gly Tyr Arg Pro Ser Lys Ile Asp Gln Asn Thr Ser Thr Phe Ser
465                 470                 475                 480
Gln Tyr Asp Gln Leu Glu Tyr Lys Thr Glu Lys Leu Ser Ala Leu Ile
                485                 490                 495
Gly Ala Arg Ile Asp Tyr Val Leu Leu Asn Gln Asp Gly Lys Arg Tyr
                500                 505                 510
Ile Asp Pro Leu Phe Ile Phe Ser Pro Arg Ala Asn Val Arg Tyr Asn
                515                 520                 525
Pro Asn Lys Asn Leu Ser Phe Arg Leu Ser Tyr Ser Glu Gly Phe Arg
530                 535                 540
Ala Pro Gln Tyr Phe Asp Glu Asp Leu His Val Glu Leu Ala Gly Gly
545                 550                 555                 560
Thr Pro Ile Ser Arg Val Leu Ser Pro Asn Leu Lys Glu Glu Arg Ser
                565                 570                 575
Arg Ser Ile Ser Ala Ser Phe Asp Tyr Tyr His Arg Ala Asp Glu Trp
                580                 585                 590
Gln Phe Asn Ile Met Gly Glu Ala Phe Ser Thr Phe Ile Ser Asn Gln
                595                 600                 605
Phe Lys Pro Ser Asp Lys Val Glu Thr Thr Ser Asp Gly Lys Glu Trp
610                 615                 620
Ile Ile Arg Thr Ile Tyr Asn Asp Lys Asp Gly Val Ser Lys Val Tyr
625                 630                 635                 640
Gly Val Asn Leu Glu Gly Arg Ile Ala Tyr Asn Lys Ser Phe Asp Leu
                645                 650                 655
Gln Leu Gly Gly Thr Trp Gln Arg Ser Arg Tyr Gly Ser Ile Tyr Thr
                660                 665                 670
Ala Val Glu Ala Asp Lys Thr Thr Gly Gln Ala Glu Ile Ser Val Lys
                675                 680                 685
Asp Tyr Val Arg Thr Pro Asn Leu Tyr Gly Tyr Phe Val Ala Thr Val
                690                 695                 700
Arg Pro Thr Glu His Phe Ala Ile Asn Leu Ser Gly Thr Phe Thr Gly
705                 710                 715                 720
Lys Met Asp Val Val His Glu Ala Tyr Glu Gly Asp Ile Pro Ala Glu
                725                 730                 735
His Ile Ala Pro Asp Gly Ser Phe Asp Phe Glu Met Asn Gly Gln Gln
                740                 745                 750
Phe Lys Gly Leu Ala Glu Gly His Ala Lys Leu Val Lys Thr Pro Ala
                755                 760                 765
Phe Ala Asp Ile Asp Leu Lys Leu Ser His Asp Phe His Leu Ala Ser
                770                 775                 780
Thr Met Thr Leu Glu Leu Asn Ala Gly Ile Gln Asn Ile Phe Asn Ser
785                 790                 795                 800
Tyr Gln Lys Asp Thr Asp Lys Gly Pro Gly Arg Ala Ser Thr Tyr Val
                805                 810                 815
Tyr Gly Pro Met Gln Pro Arg Arg Ile Phe Val Gly Thr Lys Ile Asn
                820                 825                 830

Phe

<210> SEQ ID NO 82
<211> LENGTH: 229
```

<212> TYPE: PRT
<213> ORGANISM: Porphyromonas gingivalis

<400> SEQUENCE: 82

Met Met Lys Lys Ala Phe Val Phe Val Leu Leu Val Cys Leu Phe Ser
1               5                   10                  15

Ser Phe Ser Ser Ser Ala Gln Thr Thr Thr Asn Ser Ser Arg Ser Tyr
            20                  25                  30

Phe Thr Gly Arg Ile Glu Lys Val Ser Leu Asn Leu Gly Val Pro Pro
        35                  40                  45

Val Ser Thr Glu Val Trp Gly Met Thr His Asp Ala Asn Gly Leu Pro
    50                  55                  60

Phe Glu Ile Pro Ile Ser Phe Ser Arg Phe Asn Ser Gln Gly Asp Ile
65                  70                  75                  80

Ala Thr Thr Tyr Tyr Ile Ala Asn Ser Glu Ala Thr Leu Asn Glu Trp
                85                  90                  95

Cys Asp Tyr Ala His Pro Gly Gly Ile Val Arg Val Glu Gly Arg Phe
            100                 105                 110

Trp Lys Met Thr Tyr Asn Ile Pro Thr Tyr Asn Ala Val Cys Thr Arg
        115                 120                 125

Ile Thr Phe Glu Asn Gln Glu Ile Glu Gly Thr Ile Val Leu Ile Pro
    130                 135                 140

Lys Pro Lys Val Ser Leu Pro His Val Ser Glu Ser Val Pro Cys Ile
145                 150                 155                 160

Arg Thr Glu Ala Gly Arg Glu Phe Ile Leu Cys Glu Glu Asp Asp Thr
                165                 170                 175

Phe Val Ser His Asp Gly Asn Glu Val Thr Ile Gly Gly Lys Pro Phe
            180                 185                 190

Leu Leu Asn Thr Asn Val Lys Ile Val Gly Asp Val Ser Gln Lys Tyr
        195                 200                 205

Ala Val Gly Val Gly Glu Ile Arg Phe Leu Gln Ile Cys Ala Gln Thr
    210                 215                 220

Val Ser Gln Gln Lys
225

<210> SEQ ID NO 83
<211> LENGTH: 380
<212> TYPE: PRT
<213> ORGANISM: Porphyromonas gingivalis

<400> SEQUENCE: 83

Met Lys Ala Lys Ser Leu Leu Ala Leu Ala Gly Leu Ala Cys Thr
1               5                   10                  15

Phe Ser Ala Thr Ala Gln Glu Ala Thr Thr Gln Asn Lys Ala Gly Met
            20                  25                  30

His Thr Ala Phe Gln Arg Asp Lys Ala Ser Asp His Trp Phe Ile Asp
        35                  40                  45

Ile Ala Gly Gly Ala Gly Met Ala Leu Ser Gly Trp Asn Asn Asp Val
    50                  55                  60

Asp Phe Val Asp Arg Leu Ser Ile Val Pro Thr Phe Gly Ile Gly Lys
65                  70                  75                  80

Trp His Glu Pro Tyr Phe Gly Thr Arg Leu Gln Phe Thr Gly Phe Asp
                85                  90                  95

Ile Tyr Gly Phe Pro Gln Gly Ser Lys Glu Arg Asn His Asn Tyr Phe
            100                 105                 110

```
Gly Asn Ala His Leu Asp Phe Met Phe Asp Leu Thr Asn Tyr Phe Gly
            115                 120                 125

Val Tyr Arg Pro Asn Arg Val Phe His Ile Ile Pro Trp Ala Gly Ile
    130                 135                 140

Gly Phe Gly Tyr Lys Phe His Ser Glu Asn Ala Asn Gly Glu Lys Val
145                 150                 155                 160

Gly Ser Lys Asp Asp Met Thr Gly Thr Val Asn Val Gly Leu Met Leu
                165                 170                 175

Lys Phe Arg Leu Ser Arg Val Val Asp Phe Asn Ile Glu Gly Gln Ala
            180                 185                 190

Phe Ala Gly Lys Met Asn Phe Ile Gly Thr Lys Arg Gly Lys Ala Asp
        195                 200                 205

Phe Pro Val Met Ala Thr Ala Gly Leu Thr Phe Asn Leu Gly Lys Thr
    210                 215                 220

Glu Trp Thr Glu Ile Val Pro Met Asp Tyr Ala Leu Val Asn Asp Leu
225                 230                 235                 240

Asn Asn Gln Ile Asn Ser Leu Arg Gly Gln Val Glu Glu Leu Ser Arg
                245                 250                 255

Arg Pro Val Ser Cys Pro Glu Cys Pro Glu Pro Thr Gln Pro Thr Val
            260                 265                 270

Thr Arg Val Val Val Asp Asn Val Val Tyr Phe Arg Ile Asn Ser Ala
        275                 280                 285

Lys Ile Asp Arg Asn Gln Glu Ile Asn Val Tyr Asn Thr Ala Glu Tyr
    290                 295                 300

Ala Lys Thr Asn Asn Ala Pro Ile Lys Val Val Gly Tyr Ala Asp Glu
305                 310                 315                 320

Lys Thr Gly Thr Ala Ala Tyr Asn Met Lys Leu Ser Glu Arg Arg Ala
                325                 330                 335

Lys Ala Val Ala Lys Met Leu Glu Lys Tyr Gly Val Ser Ala Asp Arg
            340                 345                 350

Ile Thr Ile Glu Trp Lys Gly Ser Ser Glu Gln Ile Tyr Glu Glu Asn
        355                 360                 365

Ala Trp Asn Arg Ile Val Val Met Thr Ala Ala Glu
    370                 375                 380

<210> SEQ ID NO 84
<211> LENGTH: 391
<212> TYPE: PRT
<213> ORGANISM: Porphyromonas gingivalis

<400> SEQUENCE: 84

Met Lys Val Lys Tyr Leu Met Leu Thr Leu Val Gly Ala Ile Ala Leu
1               5                   10                  15

Asn Ala Ser Ala Gln Glu Asn Thr Val Pro Ala Thr Gly Gln Leu Pro
                20                  25                  30

Ala Lys Asn Val Ala Phe Ala Arg Asn Lys Ala Gly Ser Asn Trp Phe
            35                  40                  45

Val Thr Leu Gln Gly Gly Val Ala Ala Gln Phe Leu Asn Asp Asn Asn
    50                  55                  60

Asn Lys Asp Leu Met Asp Arg Leu Gly Ala Ile Gly Ser Leu Ser Val
65                  70                  75                  80

Gly Lys Tyr His Ser Pro Phe Phe Ala Thr Arg Leu Gln Ile Asn Gly
                85                  90                  95

Gly Gln Ala His Thr Phe Leu Gly Lys Asn Gly Glu Gln Glu Ile Asn
            100                 105                 110
```

```
Thr Asn Phe Gly Ala Ala His Phe Asp Phe Met Phe Asp Val Val Asn
            115                 120                 125

Tyr Phe Ala Pro Tyr Arg Glu Asn Arg Phe Phe His Leu Ile Pro Trp
            130                 135                 140

Val Gly Val Gly Tyr Gln His Lys Phe Ile Gly Ser Glu Trp Ser Lys
145                 150                 155                 160

Asp Asn Val Glu Ser Leu Thr Ala Asn Val Gly Val Met Met Ala Phe
                165                 170                 175

Arg Leu Gly Lys Arg Val Asp Phe Val Ile Glu Ala Gln Ala Ala His
            180                 185                 190

Ser Asn Leu Asn Leu Ser Arg Ala Tyr Asn Ala Lys Lys Thr Pro Val
            195                 200                 205

Phe Glu Asp Pro Ala Gly Arg Tyr Tyr Asn Gly Phe Gln Gly Met Ala
            210                 215                 220

Thr Ala Gly Leu Asn Phe Arg Leu Gly Ala Val Gly Phe Asn Ala Ile
225                 230                 235                 240

Glu Pro Met Asp Tyr Ala Leu Ile Asn Asp Leu Asn Gly Gln Ile Asn
                245                 250                 255

Arg Leu Arg Ser Glu Val Glu Glu Leu Ser Lys Arg Pro Val Ser Cys
            260                 265                 270

Pro Glu Cys Pro Glu Val Thr Pro Val Thr Lys Thr Glu Asn Ile Leu
            275                 280                 285

Thr Glu Lys Ala Val Leu Phe Arg Phe Asp Ser His Val Val Asp Lys
            290                 295                 300

Asp Gln Leu Ile Asn Leu Tyr Asp Val Ala Gln Phe Val Lys Glu Thr
305                 310                 315                 320

Asn Glu Pro Ile Thr Val Val Gly Tyr Ala Asp Pro Thr Gly Asn Thr
                325                 330                 335

Gln Tyr Asn Glu Lys Leu Ser Glu Arg Arg Ala Lys Ala Val Val Asp
            340                 345                 350

Val Leu Thr Gly Lys Tyr Gly Val Pro Ser Glu Leu Ile Ser Val Glu
            355                 360                 365

Trp Lys Gly Asp Ser Thr Gln Pro Phe Ser Lys Lys Ala Trp Asn Arg
            370                 375                 380

Val Val Ile Val Arg Ser Lys
385                 390

<210> SEQ ID NO 85
<211> LENGTH: 333
<212> TYPE: PRT
<213> ORGANISM: Porphyromonas gingivalis

<400> SEQUENCE: 85

Met Lys Lys Tyr Leu Tyr Ala Ser Leu Leu Thr Ser Val Leu Leu
1               5                   10                  15

Phe Ser Cys Ser Lys Asn Asn Pro Asn Glu Pro Val Asp Arg Ser
            20                  25                  30

Ile Glu Ile Ser Ile Arg Val Asp Asp Phe Thr Lys Thr Gly Glu Ala
            35                  40                  45

Val Arg Tyr Glu Arg Asn Gln Gly Ser Ala Ala Glu Arg Leu Ile Thr
        50                  55                  60

Asn Leu Tyr Leu Leu Leu Phe Asp Gln Ser Gly Ala Asn Pro Ala Lys
65                  70                  75                  80

Tyr Tyr Ile Thr Gly Asn Thr Phe Thr Gly Gly Thr Trp Leu Pro Asp
```

```
                    85                  90                  95
Asp Met Lys Val Lys Leu Asp Met Thr Gln Ser Glu Ala Gly Glu Arg
                100                 105                 110

Lys Val Tyr Val Ala Asn Val Asp Asn Ala Val Lys Thr Ala Leu
            115                 120                 125

Asp Ala Val Ala Asn Glu Ser Asp Leu Gln Thr Val Lys Arg Thr Thr
        130                 135                 140

Ala Met Pro Trp Ser Thr Asp Ile Ala Ser Pro Phe Leu Met Ser Gly
145                 150                 155                 160

Asn Lys Thr His Asp Phe Leu Ala Asn Arg Leu Leu Asp Asn Val Pro
                165                 170                 175

Leu Val Arg Ala Ile Ala Lys Val Glu Leu Asn Ile Ser Leu Ser Glu
            180                 185                 190

Lys Phe Gln Ile Val Pro Ile Val Asn Gly Ser Leu Ser Glu Phe
        195                 200                 205

Lys Phe Arg Tyr Val Asn Phe Asp Lys Glu Thr Tyr Val Val Lys Pro
        210                 215                 220

Thr Thr Lys Pro Asp Asn Leu Ile Ser Ser Ala Asn Gly Val Trp Pro
225                 230                 235                 240

Gln Ile Thr Asp Trp Thr Val Trp Gly Ala Ser Leu Asn Thr Ser Pro
                245                 250                 255

Ala Pro Asp Ala Gly Thr Gly Tyr Thr Leu Asp Ala Asn Gly Lys Val
            260                 265                 270

Thr Ala Leu Arg Ile Val Thr Tyr Leu Asn Glu Arg Asp Ser Lys Gly
        275                 280                 285

Ala Thr Val Glu Val Ala Leu Pro Arg Val Asp Gly Thr Leu Pro
        290                 295                 300

Pro Pro Glu Phe Gly Pro Glu Leu Tyr Arg Leu Pro Leu Pro Asp Lys
305                 310                 315                 320

Ile Leu Arg Asn His Trp Tyr Lys Tyr Glu Val Glu Ile
                325                 330

<210> SEQ ID NO 86
<211> LENGTH: 319
<212> TYPE: PRT
<213> ORGANISM: Porphyromonas gingivalis

<400> SEQUENCE: 86

Met Val Leu Ile Arg Leu Arg Pro Cys Ser Ala Val Glu Lys Asp Leu
1               5                   10                  15

Ile His Ala Cys Ser Pro Ser Ala Ser Ala Leu Val Ser Lys Asn Glu
                20                  25                  30

Lys Ala Met Lys Arg Phe Phe Leu Thr Thr Ala Ile Leu Leu Ser Ser
            35                  40                  45

Val Leu Ala Ser Tyr Ala Asp Ser Leu Pro Ser Ala Val Arg Asp Thr
        50                  55                  60

Val Ile Arg Ala Gly Glu Lys Thr Ile Met Ile Lys Asp Gly Glu Asp
65                  70                  75                  80

Asp Phe Glu Val Ile Ile Gln Glu Ser Met Pro Ser Gly Asp Thr Ile
                85                  90                  95

Arg Asn Glu Lys Ile Phe Arg Gly Val Tyr Arg Asn Gly Arg Ser Ile
                100                 105                 110

Glu Gln Arg Phe Arg Asn Thr Leu Ile Asn Arg Pro Asn Arg Asp Lys
            115                 120                 125
```

```
Glu Met Pro Val Trp Gly Thr Tyr Gly Phe Gly Ser Phe Glu Trp Gly
    130                 135                 140

Glu Leu Lys Val Asp Asp Ser His Ser Asp Ile Gly Arg Ser His Ser
145                 150                 155                 160

Tyr Arg Val Ser Ile Gln Ile Phe Gly Asp Ile Tyr Arg Leu Asn Lys
                165                 170                 175

Tyr Leu Val Leu Thr Tyr Ala Leu Gly Trp Asp Ala Asp Ile Tyr Arg
            180                 185                 190

Ile Thr Asp Ser Lys Thr Leu Lys Asn Ile Asp Gly Val Thr Thr Val
        195                 200                 205

Val Asp Val Pro Gly Arg Ala Glu Cys Thr Leu Thr Ala Ala Tyr Leu
210                 215                 220

Lys Ala Met Pro Ala Leu Ala Phe Asn Gly Val Arg Ser Asn Leu Thr
225                 230                 235                 240

Val Tyr Ile Ala Pro Val Leu Arg Ala Lys Val Tyr Ser Ala Ala Thr
                245                 250                 255

Thr Asp Gly Pro Asp Gly Arg Leu Glu Lys Leu Arg Arg Val Lys Leu
            260                 265                 270

Asn Thr Phe Ser Val Glu Ala Arg Ala Gly Ile Asn Tyr Arg Asn Ala
        275                 280                 285

Gly Ile Phe Phe Thr Tyr Ser Leu Thr Pro Leu Phe Arg Ser Gly Lys
    290                 295                 300

Gly Pro Lys Leu His Pro Tyr Thr Ile Gly Leu Ser Leu Ser Leu
305                 310                 315

<210> SEQ ID NO 87
<211> LENGTH: 237
<212> TYPE: PRT
<213> ORGANISM: Porphyromonas gingivalis

<400> SEQUENCE: 87

Met Asn Lys Lys Asn Ile Ile Ile Gly Ser Ile Ile Ala Val Leu Ala
1               5                   10                  15

Ile Leu Leu Ile Thr Ser Phe Leu Trp Asn Arg Asp Val Arg Asn Lys
            20                  25                  30

Leu Arg Ile Ala Gln His Asn Val Glu Ala Ala Leu Asp Ser Ile Arg
        35                  40                  45

Tyr Leu Lys Asp Ala Asn Gly Asn Leu Tyr Ala Glu Lys Lys Ser Phe
    50                  55                  60

Ile Ala Thr Ile Ser Glu Leu Lys Glu Leu Asn Thr Glu Met Tyr Glu
65                  70                  75                  80

Asn Ile Gln Ser Leu Gln Lys Lys Leu Gln Lys Lys Ile Leu Ala Gly
            85                  90                  95

Ser Asp Ile Gly Val Val Val Asp Thr Ile Tyr Gln Asp Lys Ile
        100                 105                 110

Ile Glu Tyr Thr Leu Asp Ser Leu Val Asn Ile Pro Phe Ser Asp Gln
    115                 120                 125

Thr Ile Asn Ala Asn Ser Leu Val Arg Ile His Arg Asp Asn Ile Arg
130                 135                 140

Leu Gln Gln Phe Thr Tyr Asn Leu Asp Ile Pro Leu Glu Val Tyr Phe
145                 150                 155                 160

Thr Lys Asp Tyr Gln Ile Ile Ala Arg Ser Lys Asn Glu Asn Val Thr
                165                 170                 175

Phe Ser Lys Leu Asn Ser Phe Ile Asp Pro Ser Val Thr Lys Tyr Arg
            180                 185                 190
```

```
Asn Arg Lys Arg Trp Gly Phe Gly Ile Gln Ala Gly Val Gly Phe Met
        195                 200                 205

Pro Gly Tyr Asp Leu Val Arg Lys Asp Leu Val Pro Ala Val Gly Pro
    210                 215                 220

Tyr Leu Gly Val Gly Ile Ser Tyr His Ile Leu Gln Trp
225                 230                 235

<210> SEQ ID NO 88
<211> LENGTH: 446
<212> TYPE: PRT
<213> ORGANISM: Porphyromonas gingivalis

<400> SEQUENCE: 88

Met Thr Thr Met Lys Ile Arg Tyr Leu Leu Ser Ile Phe Leu Phe Cys
1                 5                  10                 15

Cys Phe Met Gly Ala Thr Gly Ala Met Ala Thr Lys Pro Val Leu Pro
                20                  25                  30

Leu Ser Gln Leu Gln Asn Pro Pro Leu Ala Asp Thr Asp Ser Leu Pro
            35                  40                  45

Thr Ser Pro Ile Val Ser Gly Arg Leu Leu Met Asn Tyr Leu Gln Leu
    50                  55                  60

Pro Leu Val Ala Glu Asn Ser Ser Gly Pro Leu Ala Ala Gly Met Trp
65                  70                  75                  80

Gln Ile Thr Met Pro Glu Ile Pro Ser Arg Leu Gln Gln Val Arg Arg
                85                  90                  95

Thr Glu Pro Leu Pro Val Pro Asp Leu Ser Asp Met Ile Ala Glu Val
                100                 105                 110

Glu Leu Ala Arg Arg Val Leu Thr Glu Leu Gln Tyr Arg Arg Leu Asp
            115                 120                 125

Leu Phe Thr Tyr Ser Arg Thr Glu Leu Glu Pro Phe Ala Pro Asp Tyr
    130                 135                 140

Ser Tyr Ile Lys Pro Gln Asp Ile Gln Leu Ile Asp Gly Gly Ala Leu
145                 150                 155                 160

Ser Asp Arg Ile Ile Met Pro Glu Lys Ile Arg Gly Ile Glu Leu Lys
                165                 170                 175

Pro Arg Tyr Trp Phe Phe Ser Met Glu Thr Met Leu Gln Phe Ser Gln
                180                 185                 190

Asn Tyr Ile Ser Glu Asn Trp Tyr Lys Gly Gly Ser Ser Asn Leu Asn
            195                 200                 205

Ile Met Phe Gly Asn Leu Ile Val Arg Gln Tyr Arg Asn Lys Lys Ile
    210                 215                 220

Arg Trp Lys Asn Glu Leu Glu Asn Lys Leu Ser Val Phe Asn Ala Ala
225                 230                 235                 240

Lys Asp Thr Val Asn Arg Tyr Arg Val Ala Glu Asp Leu Leu Arg Leu
                245                 250                 255

Arg Ser Asn Phe Gly Tyr Lys Ala Phe Lys Gln Trp Tyr Tyr Ser Phe
                260                 265                 270

Asp Ala Glu Met Arg Thr Gln Leu Phe Thr Asn Arg Ala Glu Asn Ser
            275                 280                 285

Leu Lys Lys Gln Ser Ala Phe Leu Ala Pro Met Ile Phe Asn Ser Gly
    290                 295                 300

Ile Gly Met Lys Tyr Glu Leu Asp Thr Lys Ser Lys Lys Val Tyr Gly
305                 310                 315                 320

Lys Ser Ala Lys Leu Gly Leu Phe Leu Ser Pro Leu Ser Tyr Ile Leu
```

```
                   325                 330                 335
Lys Trp Ser Ile Arg Asp Asp Ile Asp Leu Ala Arg His Gly Phe Pro
                340                 345                 350

Glu Gly Lys Thr Ile Val His Glu Leu Gly Ser Ala Ile Lys Ala Glu
                355                 360                 365

Leu Val Trp Asn Phe Asp Ser Arg Leu Ser Trp Gln Ser Arg Leu Tyr
            370                 375                 380

Ala Asn Thr Thr Tyr Asp Asn Thr Val Ala Glu Phe Glu Asn Ala Leu
385                 390                 395                 400

Asn Leu Ser Leu Ser Lys Leu Leu Ser Thr Arg Ile Tyr Leu Tyr Leu
                405                 410                 415

Arg Tyr Asp Asp Ser Val Ser Leu Pro Asp Gly Lys Gly Thr Tyr Trp
                420                 425                 430

Gln Val Asn Glu Leu Val Ser Ile Gly Leu Tyr Phe His Leu
                435                 440                 445

<210> SEQ ID NO 89
<211> LENGTH: 379
<212> TYPE: PRT
<213> ORGANISM: Porphyromonas gingivalis

<400> SEQUENCE: 89

Met Val Leu Arg Pro His Tyr Ala Asp Gly Gly Thr Val Ser His Thr
1               5                   10                  15

Ile Lys Glu Ile Ile Gln Gln Asn Asn Asp Gln Glu Met Lys
                20                  25                  30

Val Lys His Leu Leu Ala Ala Ser Leu Met Met Leu Gly Thr Gly Asn
            35                  40                  45

Ile Cys Ala Gln Lys Ser Ala Asn Ser Ile Phe Asn Ala Ile Lys Glu
        50                  55                  60

Arg Val Ser Leu Ser Gly Tyr Ala Gln Ala Gly Phe Ser Ser Leu Trp
65                  70                  75                  80

Leu Pro Thr Ala Ser Ser Glu Lys Glu Asn Tyr Asn Thr Phe Asp Val
                85                  90                  95

Lys Arg Ile Thr Leu Arg Ala Asn Val Ala Ile Thr Asp Lys Trp Ser
                100                 105                 110

Val Thr Phe Ile Pro Asp Phe Ala Lys Arg Tyr Thr Asn Leu Glu Leu
            115                 120                 125

Tyr Thr Ser Phe Arg Thr Cys Ser Gly Phe Gly Ile Arg Leu Gly Gln
        130                 135                 140

Phe Lys Thr Ala Phe Ser Ile Glu Asn Gln Leu Ser Pro Thr Thr Ile
145                 150                 155                 160

Glu Thr Ile Ser Cys Gly Ser Met Ala Thr Asn Phe Leu Ala Ala Gly
                165                 170                 175

Asn Gly Ser Asp Pro Leu Met Gly Ala Gln Ser Gly Arg Asp Val Gly
            180                 185                 190

Leu Glu Ile Tyr Gly Asp Leu Phe Asn Asp Ile Leu Gly Tyr Arg Leu
        195                 200                 205

Gly Val Leu Asn Gly Gln Gly Ile Asn Thr Leu Asp Gly Ser Lys His
    210                 215                 220

Lys Thr Leu Glu Gly Ser Leu Thr Leu Arg Pro Ile Glu Cys Leu Ser
225                 230                 235                 240

Phe Thr Gly Ser Phe Met Ser Gly Lys Thr Ala Ala Leu Asn Asp Ala
                245                 250                 255
```

```
Pro Ile Lys Ile Asn Ser Lys Gln Ile Met Ala Gly Asp Leu Tyr Asp
            260                 265                 270

Arg Ser Arg Trp Ser Val Gly Gly Met Phe Arg Ser Lys Tyr Leu Asp
            275                 280                 285

Leu Arg Ser Glu Tyr Leu Glu Gly Lys Asp Asp Met Ile Ser Lys
            290                 295                 300

Gly Phe Tyr Val Thr Gly Val Gly Arg Leu Phe Lys Asn Leu Asp Ile
305                 310                 315                 320

Ile Gly Ser Tyr Asp Phe Met Asp Leu Tyr Glu Arg Gln Gln Val His
                325                 330                 335

Asn Ile Thr Ala Gly Leu Gln Tyr Trp Phe Phe Pro Lys Cys Arg Leu
            340                 345                 350

Gln Ala Gln Tyr Val Leu Ser Asn Pro Lys Gly Glu Tyr Asn Asn Thr
            355                 360                 365

His Ala Leu Leu Thr Gln Val Gln Val Ala Phe
            370                 375

<210> SEQ ID NO 90
<211> LENGTH: 891
<212> TYPE: PRT
<213> ORGANISM: Porphyromonas gingivalis

<400> SEQUENCE: 90

Met His Ile Phe Gly Tyr Val Ala Arg Asn Val Leu Phe Val Leu Phe
1               5                   10                  15

Gly Leu Ile Phe Gly Tyr Glu Val Ser Tyr Ala Gln Thr Ile Thr Ile
            20                  25                  30

Lys Gly Gln Val Leu Asp Glu Lys Lys Gln Pro Val Ser Tyr Ala Ser
            35                  40                  45

Val Val Ile Ser Thr Asp Ser Leu Ser Lys Lys Asp Ile Ser Tyr Ala
    50                  55                  60

Val Thr Asp Glu His Gly Gln Phe Arg Ile Gly Gln Leu Ser Ala Ile
65                  70                  75                  80

Pro Asp Lys Arg Trp Ile His Val Arg Ser Ile Gly Tyr Leu Gly Phe
                85                  90                  95

His Lys Gln Ile Ser Leu Arg Ala Val Lys Ser Pro Leu Asp Ile Thr
            100                 105                 110

Leu Thr Glu Asp Thr Lys Glu Leu Glu Glu Val Val Val Ala Arg
            115                 120                 125

Ala Arg Asp Ala Tyr Ala Lys Gly Asp Thr Ile Val Phe Asn Ser Lys
130                 135                 140

Asn Tyr Thr Leu Gly Asn Glu Arg Asn Leu Gly Asp Val Val Lys Lys
145                 150                 155                 160

Met Pro Gly Met Glu Val Asp Gln Thr Gly Asn Ile Ser Tyr Gln Gly
                165                 170                 175

Lys Lys Ile Gly Lys Val Leu Val Asp Gly Gln Asp Ile Leu Ser Ser
            180                 185                 190

Ser Ser Gly Val Ala Met Asn Thr Leu Pro Pro Asp Phe Ala Asn Ser
            195                 200                 205

Ile Glu Leu Leu Ser Asn Tyr Thr Asp Gly Asp Ile Ala His Ala Phe
            210                 215                 220

Lys Ala Glu Glu Gln Leu Ala Leu Asn Leu Lys Ser Asn Lys Lys Val
225                 230                 235                 240

Ala Leu Ser Gly Ser Phe Glu Gly Gly Gly Leu Lys Asp Lys Phe
                245                 250                 255
```

```
Ile Ser Lys Ala Ser Leu Ile Thr Val Leu Pro Lys Ile Ser Ala Ser
            260                 265                 270

Thr Ile Ile Asn Ala Asn Asn Thr Gly Glu Ala Val Phe Ser Ile Gln
            275                 280                 285

Asp Tyr Met Ser Asn Ile Ile Asp Phe Glu Ser Ile Arg Ser Gly Ala
            290                 295                 300

Ser Thr Gln Thr Ser Leu Ser Leu Ser Pro Glu Glu Gln Gln Leu Leu
305                 310                 315                 320

Leu Pro Pro Thr Asn Glu His Ala Arg Thr Ala Gly Leu Ala Asn Ile
            325                 330                 335

Asn Ile Ser Trp Thr Pro His Ser Ser Tyr Lys Leu Arg Ala Ser Thr
            340                 345                 350

Leu Phe Asn Lys Gly Lys Ser Glu Gly Ala His Thr Lys Thr Asp Thr
            355                 360                 365

Tyr Thr Leu Pro Glu Asn Tyr Phe Thr Asn Ile Ser Thr Gly Thr Ala
            370                 375                 380

Asp Lys Glu Thr Gln Leu Val Ser Gln Tyr Leu Ser Gln Lys Trp Ile
385                 390                 395                 400

Pro Ser Arg Phe Phe Ser Val Ser Ala Lys Thr Lys Ile Asp Ile Arg
            405                 410                 415

Asn His Asn Ala Asp Asn Ile Tyr Ala Asn Thr Phe Asn Asp Asn His
            420                 425                 430

Ile His Ala Leu Glu Lys Pro Lys Asn His Phe Ser Gly Ile Lys Gln
            435                 440                 445

Asp Ile Glu Met Lys Trp Leu Leu Ser Lys Gly Leu Leu Phe Gly Gly
            450                 455                 460

Gly Ser Phe Val Phe Asn Lys Gly Lys Ile Asn Ser Asp Ile Tyr Thr
465                 470                 475                 480

Asp Val Leu Leu Leu Pro Leu Pro His Ile Asn Gly Asn Ser Ile Tyr
            485                 490                 495

Pro Tyr Phe His Glu His Ile Lys Lys Asp Met Glu Lys Gly Phe Asn
            500                 505                 510

Ala Tyr Val Gly Gly Met Tyr Pro Val Leu Asn Asn Ile Tyr Leu Arg
            515                 520                 525

Gly Glu Phe Ser Met Ser Met Asn Trp Asn Glu Leu Lys Met Ala Tyr
            530                 535                 540

Pro Thr Ser Ile Asn Glu Glu Thr Ala Asp Leu Arg Val Phe Arg Pro
545                 550                 555                 560

Tyr Ile Ser Leu Met Lys Asn Lys Gly Val Phe Arg Phe Asn Ile Gly
            565                 570                 575

Ser Tyr Phe Ser Ser Tyr Arg Gln Lys Thr Ser Pro Glu Leu Leu Arg
            580                 585                 590

Glu Lys Ser Leu Phe Tyr Ile Glu Pro His Ala Ser Ile Glu Leu Val
            595                 600                 605

Met Ser Asn Gln His Arg Leu Met Leu Ser Val Ser Glu Ala Val Ser
            610                 615                 620

Pro Ser Thr Ile Asp Tyr Phe Ser Gln Gln Ile Leu Ala Lys Gly Tyr
625                 630                 635                 640

Asn Asn Leu Gln Leu Pro Ser Lys Leu Ser Asn Pro Phe Ala Lys Arg
            645                 650                 655

Phe Lys Gly Asn Leu Ser Tyr Ala Tyr Phe Ser Leu Phe Asn Arg Leu
            660                 665                 670
```

```
Ser Met Tyr Gly Asn Leu Ser Tyr Ile Lys Asp Arg Asp Thr His Ile
            675                 680                 685

Thr Val Thr Thr Ser Lys Gly Leu Leu Ile Ser Asn Phe Tyr Gln Asp
    690                 695                 700

Gly Gly Trp Ser Asn Thr Leu Arg Thr Asn Ala Tyr Leu Ser Lys Gly
705                 710                 715                 720

Ile Gly Thr Leu Pro Leu Asp Ile Lys Leu Ser Gly Lys Tyr Thr Leu
                725                 730                 735

Ser Lys His Asn Leu Met Arg Val Asp Lys Glu Asp Glu Leu Ile Asn
            740                 745                 750

Lys Arg Val Asp Ala Lys Leu Asp Leu Ile Ser Arg Leu Tyr Gln Ser
        755                 760                 765

Pro Val Asn Phe Glu Ile Gly Val Arg Phe Ser Arg Leu Asp Gln Lys
    770                 775                 780

Phe Thr Tyr Ser Asn Ile His Ser Trp Asn Gln Glu Phe Gly Gly Phe
785                 790                 795                 800

Ala Thr Thr His Val Asn Ile Gly Asn Phe Val Phe Ser Val Ser Gly
                805                 810                 815

Lys Ser Asn Arg Ile Glu Asp Ala Glu Ala Lys Arg Tyr Phe Arg Asp
            820                 825                 830

Leu Asp Phe Ser Leu Lys Tyr Lys Leu Ser Lys Leu Asp Ile Lys Leu
        835                 840                 845

Gln Gly Glu Asn Val Phe His Leu Lys Asp Asn Glu Trp Met Lys Glu
    850                 855                 860

Ile Leu Thr Pro Thr Val Gln Ser Thr Ile Leu Tyr Arg Arg Leu Pro
865                 870                 875                 880

Gly His Ile Leu Leu Ser Leu Ser Tyr Thr Leu
                885                 890
```

<210> SEQ ID NO 91
<211> LENGTH: 479
<212> TYPE: PRT
<213> ORGANISM: Porphyromonas gingivalis

<400> SEQUENCE: 91

```
Met Lys Arg Ile Gln Leu Thr Leu Ile Ala Leu Phe Ala Ala Val Ala
1               5                   10                  15

Gly Leu Val Ala Gln Asn Ala Tyr Glu Gly Val Ile Ser Tyr Lys Ile
                20                  25                  30

Ser Leu Asp Lys Thr Gly Asn Lys Val Val Leu Asn Gly Ala Ala Asp
            35                  40                  45

Met Ser Asn Leu Lys Leu Lys Ser Thr Gln Met Ile Ile Val Thr Pro
        50                  55                  60

Ile Leu Arg Ser Glu Asp Gly Thr Ser Arg Val Glu Phe Pro Ser Val
65                  70                  75                  80

Val Ile Thr Gly Arg Asn Arg Thr Lys Ala Leu Lys Arg Glu Ile Ala
                85                  90                  95

Phe Ser Ser Ala Leu Pro Gln Ala Lys His Ala Ala Gln Tyr Ile Arg
            100                 105                 110

Arg His Asn Gly Lys Ser Glu Gln Phe Ala Phe Thr Gly Glu His Ala
        115                 120                 125

Tyr Ala Ser Trp Met Met Asp Ala Lys Phe Val Val Arg Glu Glu Val
    130                 135                 140

Arg Gly Cys Ala Lys Cys Pro Val Gly Leu Ser Ser Asn Ile Val Pro
145                 150                 155                 160
```

Phe Asp Pro Leu Phe Asn Pro Ala Glu Ala Pro Tyr Leu Ala His
                165                 170                 175

Ile Thr Pro Ala Glu Glu Val Glu Lys Gln Arg Glu Ser Ser Phe Asp
                180                 185                 190

Ala Tyr Ile Asn Phe Lys Val Asn Lys Ala Asp Val Leu Pro Glu Tyr
                195                 200                 205

Arg Asn Asn Lys Ala Glu Leu Glu Lys Ile Lys Glu Phe Val Ser Thr
210                 215                 220

Val Lys Ala Asn Pro Asn Tyr Ser Val Asn Lys Met Ile Ile Glu Gly
225                 230                 235                 240

Phe Ala Ser Pro Glu Ala Ser Ile Ala His Asn Lys Ala Leu Ser Glu
                245                 250                 255

Arg Arg Ala Lys Arg Leu Ala Glu Glu Leu Val Arg Lys Tyr Gly Lys
                260                 265                 270

Thr Leu Pro Asn Ile Thr Thr Glu Phe Gly Gly Glu Asp Trp Lys Gly
                275                 280                 285

Leu Lys Leu Ala Ile Glu Lys Ser Asp Ile Ala Asp Arg Asp Arg Val
                290                 295                 300

Leu Glu Ile Ile Asn Ser Asp Lys Tyr Ala Asp Asp Ala Arg Glu
305                 310                 315                 320

Gln Ala Leu Lys Gln Leu Ser Ser Tyr Arg Tyr Ile Leu Asp Gln Ile
                325                 330                 335

Tyr Pro Asn Leu Arg Arg Asn Thr Ile Thr Met Gly Tyr Ile Val Arg
                340                 345                 350

Asp Tyr Thr Leu Glu Glu Ala Arg Glu Ile Ile Lys Thr Ala Pro Lys
                355                 360                 365

Glu Leu Ser Glu Ala Glu Met Tyr Arg Val Ala Met Ser Tyr Pro Glu
                370                 375                 380

Gly His Gln Glu Arg Leu Phe Ala Leu Asn Thr Thr Leu Lys Tyr Phe
385                 390                 395                 400

Pro Glu Ser Val Thr Gly Arg Ile Asn Leu Ala Val Ala Ala Phe Asn
                405                 410                 415

Gly Gly Asp Val Gln Gln Ala Ile Ala Leu Leu Ser Pro Ile Gln Thr
                420                 425                 430

Glu Lys Gly Val Ser Asn Ile Leu Gly Ala Ala Tyr Ala Arg Thr Gly
                435                 440                 445

Asp Phe Ala Arg Ala Glu Thr Phe Phe Arg Lys Ala Val Ala Glu Gly
                450                 455                 460

Asp Ala Asn Ala Gln Arg Asn Leu Asp Met Leu Leu Gly Lys Lys
465                 470                 475

<210> SEQ ID NO 92
<211> LENGTH: 189
<212> TYPE: PRT
<213> ORGANISM: Porphyromonas gingivalis

<400> SEQUENCE: 92

Met Leu Phe Leu Ser Gly Leu Leu Gly Val Ser Ala Gln Arg Val Ala
1               5                   10                  15

Leu Lys Asn Asn Leu Leu Tyr Asp Ala Thr Leu Thr Pro Asn Leu Ala
                20                  25                  30

Leu Glu Ile Gly Val Gly Pro Lys Met Thr Val Asp Leu Leu Gly Gly
                35                  40                  45

Val Asn Pro Phe Lys Ile Ser Asp Asp His Tyr Trp Lys His Trp Leu

```
            50                  55                  60
Ala Gln Pro Glu Leu Arg Tyr Trp Phe Cys Glu Lys Phe Asn Gly Val
 65                  70                  75                  80

Cys Ile Gly Leu His Gly His Val Gly Gln Met Asn Ile Ala Gly Ile
             85                  90                  95

Ser Val Pro Pro Val Gly Ser Ile His Pro Lys Ser Asp Phe Asp Asp
            100                 105                 110

Ala Arg Tyr His Arg Tyr Gln Gly Trp Phe Tyr Gly Gly Gly Ile Ser
            115                 120                 125

Ile Gly Arg Gln Trp Ile Leu Gly Asn His Trp Asn Leu Glu Ala Ser
            130                 135                 140

Ile Gly Gly Gly Tyr Ile His Phe Asp Tyr Asp Lys Tyr Gln Cys Val
145                 150                 155                 160

Glu Cys Gly Lys Lys Val Gly Val Asp Lys Lys Ala Asp Tyr Phe Gly
            165                 170                 175

Leu Thr Arg Ala Thr Leu Ser Leu Ile Tyr Leu Phe Lys
            180                 185
```

IMMUNOLOGY TREATMENT FOR BIOFILMS

RELATED APPLICATIONS

This is a division of Ser. No. 12/668,407, filed May 17, 2010, now abandoned Ser. No. 12/668,407 is a national stage entry of PCT/AU08/01018, International Filing Date: Jul. 11, 2008 claims foreign priority to 2007903787, filed Jul. 12, 2007

SEQUENCE LISTING

The instant application contains a Sequence Listing which has been submitted electronically in ASCII format via and is hereby incorporated by reference in its entirety. Said ASCII copy, created on Dec. 13, 2013, is named 097589-0193_SL.txt and is 136,279 bytes in size.

FIELD OF THE INVENTION

The present invention relates to compositions and methods for preventing or altering bacterial biofilm formation and/or development such as those containing *Porphyromonas gingivalis*. In particular the present invention relates to the use and inhibition of polypeptides which are regulated during growth as a biofilm or under haem-limitation, to modulate biofilm formation and/or development. The present invention relates to the identification of polypeptides which may be used as the basis for an antibacterial vaccine or an immunotherapeutic/immunoprophylactic.

BACKGROUND OF THE INVENTION

Many bacterial treatments are directed to bacteria in a planktonic state. However, bacterial pathologies include bacteria in a biofilm state. For example, *Porphyromonas gingivalis* is considered to be the major causative agent of chronic periodontal disease. Tissue damage associated with the disease is caused by a dysregulated host immune response to *P. gingivalis* growing as a part of a polymicrobial bacterial biofilm on the surface of the tooth. Bacterial biofilms are ubiquitous in nature and are defined as matrix-enclosed bacterial populations adherent to each other and/or to surfaces or interfaces (1). These sessile bacterial cells adhering to and growing on a surface as a mature biofilm are able to survive in hostile environments which can include the presence of antimicrobial agents, shear forces and nutrient deprivation.

The Centers for Disease Control and Prevention estimate that 65% of human bacterial infections involve biofilms. Biofilms often complicate treatment of chronic infections by protecting bacteria from the immune system, decreasing antibiotic efficacy and dispersing planktonic cells to distant sites that can aid reinfection (2,3). Dental plaque is a classic example of a bacterial biofilm where a high diversity of species form a heterogeneous polymicrobial biofilm growing on the surface of the tooth. The surface of the tooth is a unique microbial habitat as it is the only hard, permanent, non-shedding surface in the human body. This allows the accretion of a substantial bacterial biofilm over a lengthy time period as opposed to mucosal surfaces where epithelial cell shedding limits development of the biofilm. Therefore, the changes to the *P. gingivalis* proteome that occur between the planktonic and biofilm states are important to our understanding of the progression of chronic periodontal disease.

*P. gingivalis* has been classified into two broad strain groups with strains including W50 and W83 being described as invasive in animal models whilst strains including 381 and ATCC 33277 are described as non-invasive (4,5). Griffen et al. (6) found that W83/W50-like strains were more associated with human periodontal disease than other *P. gingivalis* strains, including 381-like strains, whilst Cutler et al. (7) demonstrated that invasive strains of *P. gingivalis* were more resistant to phagocytosis than non-invasive strains. Comparison of the sequenced *P. gingivalis* W83 strain to the type strain ATCC 33277 indicated that 7% of genes were absent or highly divergent in strain 33277 indicating that there are considerable differences between the strains (8). Interestingly *P. gingivalis* strain W50 forms biofilms only poorly under most circumstances compared to strain 33277 which readily forms biofilms (9). As a consequence of this relatively few studies have been conducted on biofilm formation by *P. gingivalis* W50.

Quantitative proteomic studies have been employed to determine proteome changes of human bacterial pathogens such as *Pseudomonas aeruginosa, Escherichia coli* and *Streptococcus mutans* from the planktonic to biofilm state using 2D gel electrophoresis approaches, where protein ratios are calculated on the basis of gel staining intensity (10-12). An alternative is to use stable isotope labelling techniques such as ICAT, iTRAQ or heavy water ($H_2^{18}O$) with MS quantification (13). The basis for $H_2^{18}O$ labelling is that during protein hydrolysis endopeptidases such as trypsin have been demonstrated to incorporate two $^{18}O$ atoms into the C-termini of the resulting peptides (14,15). In addition to use in the determination of relative protein abundances (16-19), $^{18}O$ labelling in proteomics has also been used for the identification of the protein C-terminus, identification of N-linked glycosylation after enzymatic removal of the glycan, simplification of MS/MS data interpretation and more recently for validation of phosphorylation sites (20-23). The $^{16}O/^{18}O$ proteolytic labelling method for measuring relative protein abundance involves digesting one sample in $H_2^{16}O$ and the other sample in $H_2^{18}O$. The digests are then combined prior to analysis by LC MS/MS. Peptides eluting from the LC column can be quantified by measuring the relative signal intensities of the peptide ion pairs in the MS mode. The incorporation of two $^{18}O$ atoms into the C-terminus of digested peptides by trypsin results in a mass shift of +4 m/z allowing the identification of the isotope pairs.

Due to the complexity of the proteome, prefractionation steps are advantageous for increasing the number of peptide and protein identifications. Most prefractionation steps involve a 2D LC approach at the peptide level after in-solution digestion (24,25). However due to potential sample loss during the initial dehydration steps of the protein solution, SDS PAGE prefractionation at the protein level followed by $^{16}O/^{18}O$ labelling during in gel digestion has also been carried out successfully, (26-29). The $^{16}O/^{18}O$ proteolytic labelling is a highly specific and versatile methodology but few validation studies on a large scale have been performed (30). An excellent validation study was carried out by Qian et al (18) who labelled two similar aliquots of serum proteins in a 1:1 ratio and obtained an average ratio of 1.02±0.23 from 891 peptides. A more recent study by Lane et al (26) further demonstrated the feasibility of the $^{16}O/^{18}O$ method using a reverse labelling strategy to determine the relative abundance of 17 cytochrome P450 proteins between control and cytochrome P450 inducers treated mice that are grafted with human tumours.

SUMMARY OF THE INVENTION

This invention is illustrated by reference to a sample system whereby *P. gingivalis* W50 is grown in continuous culture and a mature biofilm developed on the vertical surfaces in the chemostat vessel over an extended period of time. The final biofilm is similar to that which would be seen under conditions of disease progression, thus allowing a direct comparison between biofilm and planktonic cells. $^{16}O/^{18}O$ proteolytic labelling using a reverse labelling strategy was carried out after SDS-PAGE prefractionation of the P. gingivalis cell envelope fraction followed by coupling to off-line LC MALDI TOF-MS/MS for identification and quantification. Of the 116 proteins identified, 81 were consistently found in two independent continuous culture studies. 47 proteins with a variety of functions were found to consistently increase or decrease in abundance in the biofilm cells providing potential targets for biofilm control strategies. Of these 47 proteins the present inventors have selected 24 proteins which they believe are particular useful as targets in treatment and/or prevention of P. gingivalis infection.

Accordingly, the present invention is directed in a first aspect towards a polypeptide which modulates biofilm formation. In one form, the microorganisms in the biofilm are bacteria. In one form, the bacteriais from the genus Porphyromonas. In one embodiment, the bacteria is P. gingivalis and the polypeptide has an amino acid sequence selected from the group consisting of the sequences corresponding to the accession numbers listed in Table 4. The invention extends to sequences at least 80% identical thereto, preferably 85%, 90%, 95%, 96%, 97%, 98%, or 99% identical thereto.

The invention also includes a polypeptide corresponding to accession number AAQ65742 (version 0.1) (SEQ ID NO. 74) and a polypeptide at least 80%, 85%, 90%, 95%, 96%, 97%, 98% or 99% identical hereto.

Preferably, the polypeptide is at least 96%, 97%, 98%, 99% or 100% identical to the amino acid sequence of any one of the sequences corresponding to the accession numbers listed in Table 4.

One aspect of the invention is a composition for use in raising an immune response directed against P. gingivalis in a subject, the composition comprising an effective amount of at least one polypeptide of the first aspect of the invention or an antigenic or immunogenic portion thereof. The composition may optionally include an adjuvant and a pharmaceutically acceptable carrier. Thus, the composition may contain an antigenic portion of such a polypeptide instead of the full length polypeptide. Typically, the portion will be substantially identical to at least 10, more usually 20 or 50 amino acids of a polypeptide corresponding to the sequences listed in Table 4 and generate an immunological response. In a preferred form, the composition is a vaccine.

The invention also provides a composition that raises an immune response to P. gingivalis in a subject, the composition comprising an amount effective to raise an immune response of at least one antigenic or immunogenic portion of a polypeptide corresponding to accession numbers selected from the group consisting of AAQ65462 (SEQ ID NO. 73), AAQ65742 (SEQ ID NO. AAQ66991 (SEQ ID NO. 75), AAQ65561 (SEQ ID NO. 76), AAQ66831 (SEQ ID NO. AAQ66797 (SEQ ID NO. 78), AAQ66469 (SEQ ID NO. 79), AAQ66587 (SEQ ID NO. 80), AAQ66654 (SEQ ID NO: 72), AAQ66977 (SEQ ID NO. 81), AAQ65797 (SEQ ID NO. AAQ65867 (SEQ ID NO. 83), AAQ65868 (SEQ ID NO. 84), AAQ65416 (SEQ ID NO. AAQ65449 (SEQ ID NO. 86), AAQ66051 (SEQ ID NO. 87), AAQ66377 (SEQ ID NO. AAQ66444 (SEQ ID NO. 89), AAQ66538 (SEQ ID NO. 90), AAQ67117 (SEQ ID NO. 91) and AAQ67118 (SEQ ID NO. 92).

In another embodiment, there is provided a composition for use in raising an immune response directed against P. gingivalis in a subject, the composition comprising an effective amount of at least one polypeptide corresponding to an accession number selected from the group consisting of AAQ65462, AAQ66991 (SEQ ID NO. 75), AAQ65561 (SEQ ID NO. 76) and AAQ66831 (SEQ ID NO. 77).

In another embodiment, there is provided a composition for use in raising an immune response directed against P. gingivalis in a subject, the composition comprising an effective amount of a polypeptide corresponding to accession number AAQ65742 (SEQ ID NO. 74).

In another embodiment, there is provided a composition for use in raising an immune response to P. gingivalis in a subject, the composition comprising amount effective to raise an immune response of at least one polypeptide having an amino acid sequence substantially identical to at least 50 amino acids of a polypeptide expressed by P. gingivalis and that is predicted by the CELLO program to be extracellular.

In another embodiment, there is provided a composition for use in raising an immune response to P. gingivalis in a subject, the composition comprising an amount effective to raise an immune response of at least one polypeptide having an amino acid sequence selected substantially identical to at least 50 amino acids of a polypeptide that causes an immune response in a mouse or a rabbit.

In one embodiment, there is provided an isolated antigenic polypeptide comprising an amino acid sequence comprising at least 50, 60, 70, 80, 90 or 100 amino acids substantially identical to a contiguous amino acid sequence of one of the sequences corresponding to the accession numbers listed in Table 4. The polypeptide may be purified or recombinant.

In another embodiment there is a composition for the treatment of periodontal disease comprising as an active ingredient an effective amount of at least one polypeptide of the first aspect of the invention.

In another embodiment there is a composition for the treatment of P. gingivalis infection comprising as an active ingredient an effective amount of at least one polypeptide of the first aspect of the invention.

Another aspect of the invention is a method of preventing or treating a subject for periodontal disease comprising administering to the subject a composition according to the present invention as described above.

Another aspect of the invention is a method of preventing or treating a subject for P. gingivalis infection comprising administering to the subject a composition according to the present invention as described above.

In another aspect of the invention there is a use of a polypeptide of the invention in the manufacture of a medicament for the treatment of P. gingivalis infection.

In another aspect of the invention there is a use of a polypeptide of the invention in the manufacture of a medicament for the treatment of periodontal disease.

The invention also extends to an antibody raised against a polypeptide of the first aspect of the present invention. Preferably, the antibody is specifically directed against one of the polypeptides corresponding to the accession numbers listed in Table 4. The antibody may be raised using the composition for raising an immune response described above.

In one embodiment, there is provided an antibody raised against a polypeptide wherein the polypeptide corresponds to an accession number selected from the group consisting of AAQ65462 (SEQ ID NO. 73), AAQ66991 (SEQ ID NO. 75), AAQ65561 (SEQ ID NO. 76) and AAQ66831 (SEQ ID NO. 77).

In one embodiment, there is provided an antibody raised against a polypeptide wherein the polypeptide corresponds to accession number AAQ65742 (SEQ ID NO. 74).

Another aspect of the invention is a composition useful in the prevention or treatment of periodontal disease, the composition comprising an antagonist or combination of antagonists of a *P. gingivalis* polypeptide of the first aspect of the present invention and a pharmaceutically acceptable carrier, wherein the antagonist(s) inhibits *P. gingivalis* infection. The antagonist(s) may be an antibody. The invention also includes use of an antagonist or combination of antagonists in the manufacture of a medicament useful for preventing or treating periodontal disease.

In a further aspect of the present invention there is provided an interfering RNA molecule, the molecule comprising a double stranded region of at least 19 base pairs in each strand wherein one of the strands of the double stranded region is substantially complementary to a region of a polynucleotide encoding a polypeptide which modulates biofilm formation as described above. In one embodiment, one of the strands is complementary to a region of polynucleotide encoding a polypeptide transcript of the sequences listed in Table 4.

BRIEF DESCRIPTION OF THE DRAWINGS

FIG. 1A MS spectra of BSA tryptic peptide, RHPEYAVSVLLR (SEQ ID NO: 1), at known $^{16}O:^{18}O$ labelling ratios 1:1 (i), 2:1 (ii), 1:5 (iii) and 10:1 (iv) showing the characteristic doublet isotopic envelope for $^{16}O$ and $^{18}O$ labelled peptide (S0, S2 and S4 are the measured intensities of the isotopic peaks) FIG. 1B SDS PAGE gel of known BSA ratios used for the quantification procedure.

FIG. 3A: Biological replicate 1 FIG. 3B: Biological replicate 2

FIG. 4A: Normalized average fold change for the 81 quantifiable proteins identified in both biological replicates displayed a Gaussian-like distribution. The abundance ratio of each protein was further normalized to zero (R−1) and ratios smaller than 1 were inverted and calculated as (1−(1/R)) (18). All 81 quantifiable proteins from each biological replicate were sorted by increasing ratios (Biofilm/Planktonic) and divided equally into six groups with equal number of proteins (A-F). Groups C and D represents proteins not significantly regulated (<3 SD from 1.0). FIG. 4B: Distribution of proteins based on rankings. Proteins were ranked in descending order with 1 having the highest similarity when both biological replicates fell within the same group and 6 having the least similarity.

DETAILED DESCRIPTION OF THE EMBODIMENTS

Figure 1A:
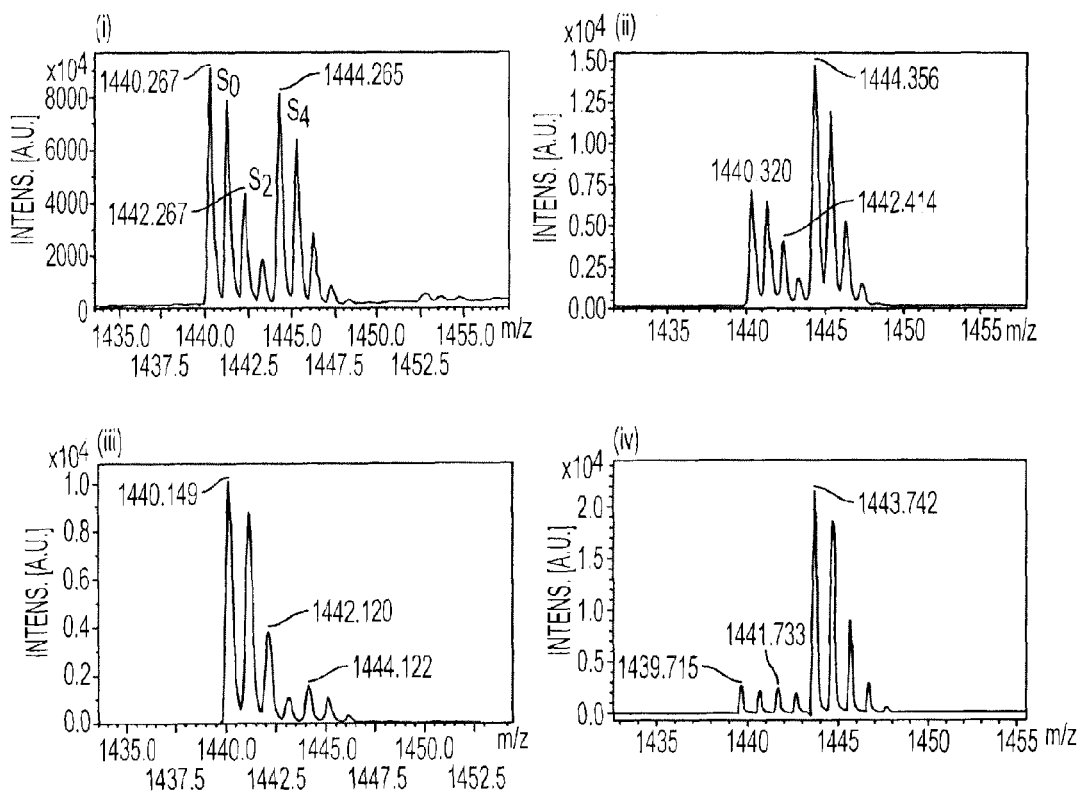
FIGS. 1A and 1B: $^{16}O/^{18}O$ quantification of specific BSA ratios. Quantification of known amounts of BSA was carried out in the same manner as for the biofilm and planktonic samples reported in the experimental procedures to validate the methodology. Briefly pre-determined amounts of BSA were loaded in adjacent lanes of a NuPAGE gel followed by excision of bands of equal size, normal or reverse proteolytic labelling, nanoHPLC and MALDI TOF-MS/MS.

The invention provides method for treating a subject including prophylactic treatment for periodontal disease. Periodontal diseases range from simple gum inflammation to serious disease that results in major damage to the soft tissue and bone that support the teeth. Periodontal disease includes gingivitis and periodontitis. An accumulation of oral bacteria at the gingival margin causes inflammation of the gums that is called 'gingivitis.' In gingivitis, the gums become red, swollen and can bleed easily. When gingivitis is not treated, it can advance to 'periodontitis' (which means 'inflammation around the tooth.'). In periodontitis, gums pull away from the teeth and form 'pockets' that are infected. Periodontitis has a specific bacterial aetiology with *P. gingivalis* regarded as the major aetiological agent The body's immune system fights the bacteria as the plaque spreads and grows below the gum line. If not treated, the bones, gums, and connective tissue that support the teeth are destroyed. The teeth may eventually become loose and have to be removed.

Using proteomic a strategy the present inventors identified and quantified the changes in abundance of 116 *P. gingivalis* cell envelope proteins between the biofilm and planktonic states, with the majority of proteins identified by multiple peptide hits. The present inventors demonstrated enhanced expression of a large group of cell-surface located C-Terminal Domain family proteins including RgpA, HagA, CPG70 and PG99. Other proteins that exhibited significant changes in abundance included transport related proteins (HmuY and IhtB), metabolic enzymes (FrdA and FrdB), immunogenic proteins and numerous proteins with as yet unknown functions.

As will be well understood by those skilled in the art alterations may be made to the amino acid sequences of the polypeptides that have been identified as having a change in abundance between biofilm and planktonic states. These alterations may be deletions, insertions, or substitutions of amino acid residues. The altered polypeptides can be either naturally occurring (that is to say, purified or isolated from a natural source) or synthetic (for example, by site-directed mutagenesis on the encoding DNA). It is intended that such altered polypeptides which have at least 85%, preferably at least 90%, 95%, 96%, 97%, 98% or 99% identity with the sequences set out in the Sequence Listing are within the scope of the present invention. Antibodies raised against these altered polypeptides will also bind to the polypeptides having one of the sequences to which the accession numbers listed in Table 4 relate.

Whilst the concept of conservative substitution is well understood by the person skilled in the art, for the sake of clarity conservative substitutions are those set out below.

Gly, Ala, Val, Ile, Leu, Met;
Asp, Glu, Ser;

Asn, Gln;
Ser, Thr;
Lys, Arg, His;
Phe, Tyr, Trp, His; and
Pro, Nα-alkalamino acids.

The practice of the invention will employ, unless otherwise indicated, conventional techniques of chemistry, molecular biology, microbiology, recombinant DNA, and immunology well known to those skilled in the art. Such techniques are described and explained throughout the literature in sources such as, J. Perbal, A Practical Guide to Molecular Cloning, John Wiley and Sons (1984), J. Sambrook et Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (Editors), Current Protocols in Molecular Biology, Greene Pub. Associates and Wiley-Interscience (1988, including all updates until present). The disclosure of these texts are incorporated herein by reference.

An 'isolated polypeptide' as used herein refers to a polypeptide that has been separated from other proteins, lipids, and nucleic acids with which it naturally occurs or the polypeptide or peptide may be synthetically synthesised. Preferably, the polypeptide is also separated from substances, for example, antibodies or gel matrix, for example, polyacrylamide, which are used to purify it. Preferably, the polypeptide constitutes at least 10%, 20%, 50%, 70%, and 80% of dry weight of the purified preparation. Preferably, the preparation contains a sufficient amount of polypeptide to allow for protein sequencing (ie at least 1,10, or 100 mg).

The isolated polypeptides described herein may be purified by standard techniques, such as column chromatography (using various matrices which interact with the protein products, such as ion exchange matrices, hydrophobic matrices and the like), affinity chromatography utilizing antibodies specific for the protein or other ligands which bind to the protein.

The terms 'peptides, proteins, and polypeptides' are used interchangeably herein. The polypeptides of the present invention can include recombinant polypeptides including fusion polypeptides. Methods for the production of a fusion polypeptide are known to those skilled in the art.

An 'antigenic polypeptide' used herein is a moiety, such as a polypeptide, analog or fragment thereof, that is capable of binding to a specific antibody with sufficiently high affinity to form a detectable antigen-antibody complex. Preferably, the antigenic polypeptide comprises an immunogenic component that is capable of eliciting a humoral and/or cellular immune response in a host animal.

In comparing polypeptide sequences, 'substantially identical' means 95% or more identical over its length or identical over any 10 contiguous amino acids.

A 'contiguous amino acid sequence' as used herein refers to a continuous stretch of amino acids.

A 'recombinant polypeptide' is a polypeptide produced by a process that involves the use of recombinant DNA technology.

A reference to 'preventing' periodontal disease means inhibiting development of the disease condition, but not necessarily permanent and complete prevention of the disease.

In determining whether or not two amino acid sequences fall within a specified percentage limit, those skilled in the art will be aware that it is necessary to conduct a side-by-side comparison or multiple alignments of sequences. In such comparisons or alignments, differences will arise in the positioning of non-identical residues, depending upon the algorithm used to perform the alignment. In the present context, reference to a percentage identity or similarity between two or more amino acid sequences shall be taken to refer to the number of identical and similar residues respectively, between said sequences as determined using any standard algorithm known to those skilled in the art. For example, amino acid sequence identities or similarities may be calculated using the GAP programme and/or aligned using the PILEUP programme of the Computer Genetics Group, Inc., University Research Park, Madison, Wis., United States of America (Devereaux et al et al., 1984). The GAP programme utilizes the algorithm of Needleman and Wunsch (1970) to maximise the number of identical/similar residues and to minimise the number and length of sequence gaps in the alignment. Alternatively or in addition, wherein more than two amino acid sequences are being compared, the Clustal W programme of Thompson et al, (1994) is used.

The present invention also provides a vaccine composition for use in raising an immune response directed against *P. gingivalis* in a subject, the composition comprising an immunogenically effective amount of at least one polypeptide of the first aspect of the invention and a pharmaceutically acceptable carrier.

The vaccine composition of the present invention preferably comprises an antigenic polypeptide that comprises at least one antigen that can be used to confer a protective response against *P. gingivalis*. The subject treated by the method of the invention may be selected from, but is not limited to, the group consisting of humans, sheep, cattle, horses, bovine, pigs, poultry, dogs and cats. Preferably, the subject is a human. An immune response directed against *P. gingivalis* is achieved in a subject, when there is development in the host of a cellular and/or antibody-mediated response against the specific antigenic polypeptides, whether or not that response is fully protective.

The vaccine composition is preferably administered to a subject to induce immunity to *P. gingivalis* and thereby prevent, inhibit or reduce the severity of periodontal disease. The vaccine composition may also be administered to a subject to treat periodontal disease wherein the periodontal disease is caused, at least in part, by *P. gingivalis*. The term 'effective amount' as used herein means a dose sufficient to elicit an immune response against *P. gingivalis*. This will vary depending on the subject and the level of *P. gingivalis* infection and ultimately will be decided by the attending scientist, physician or veterinarian.

The composition of the present invention comprises a suitable pharmaceutically-acceptable carrier, such as a diluent and/or adjuvant suitable for administration to a human or animal subject. Compositions to raise immune responses preferably comprise a suitable adjuvant for delivery orally by nasal spray, or by injection to produce a specific immune response against *P. gingivalis*. A composition of the present invention can also be based upon a recombinant nucleic acid sequence encoding an antigenic polypeptide of the present invention, wherein the nucleic acid sequence is incorporated into an appropriate vector and expressed in a suitable transformed host (eg. *E. coli, Bacillus subtilis, Saccharomyces cerevisiae*, COS cells, CHO cells and HeLa cells) containing the vector. The composition can be produced using recombinant DNA methods as illustrated herein, or can be synthesized chemically from the amino acid sequence described in the present invention. Additionally, according to the present invention, the antigenic polypeptides may be used to generate *P. gingivalis* antisera useful for passive immunization against periodontal disease and infections caused by *P. gingivalis*.

Various adjuvants known to those skilled in the art are commonly used in conjunction with vaccine formulations and formulations for raising an immune response. The adjuvants aid by modulating the immune response and in attaining a more durable and higher level of immunity using smaller amounts of vaccine antigen or fewer doses than if the vaccine antigen were administered alone. Examples of adjuvants include incomplete Freunds adjuvant (IFA), Adjuvant 65 (containing peanut oil, mannide monooleate and aluminium monostrearate), oil emulsions, Ribi adjuvant, the pluronic polyols, polyamines, Avridine, Quil A, saponin, MPL, QS-21, and mineral gels such as aluminium salts. Other examples include oil in water emulsions such as SAF-1, SAF-0, MF59, Seppic ISA720, and other particulate adjuvants such as ISCOMs and ISCOM matrix. An extensive but exhaustive list of other examples of adjuvants are listed in Cox and Coulter 1992 [In: Wong WK (ed.) Animals parasite control utilising technology. Bocca Raton; CRC press et al., 1992; 49-112]. In addition to the adjuvant the vaccine may include conventional pharmaceutically acceptable carriers, excipients, fillers, buffers or diluents as appropriate. One or more doses of a composition containing adjuvant may be administered prophylactically to prevent periodontal disease or therapeutically to treat already present periodontal disease.

In another preferred composition the preparation is combined with a mucosal adjuvant and administered via the oral or nasal route. Examples of mucosal adjuvants are cholera toxin and heat labile E. coli toxin, the non-toxic B sub-units of these toxins, genetic mutants of these toxins which have reduced toxicity. Other methods which may be utilised to deliver the antigenic polypeptides orally or nasally include incorporation of the polypeptides into particles of biodegradable polymers (such as acrylates or polyesters) by microencapsulation to aid uptake of the microspheres from the gastrointestinal tract or nasal cavity and to protect degradation of the proteins. Liposomes, ISCOMs, hydrogels are examples of other potential methods which may be further enhanced by the incorporation of targeting molecules such as LTB, CTB or lectins (mannan, chitin, and chitosan) for delivery of the antigenic polypeptides to the mucosal immune system. In addition to the composition and the mucosal adjuvant or delivery system the composition may include conventional pharmaceutically acceptable carriers, excipients, fillers, coatings, dispersion media, antibacterial and antifungal agents, buffers or diluents as appropriate.

Another mode of this embodiment provides for either a live recombinant viral vaccine, recombinant bacterial vaccine, recombinant attenuated bacterial vaccine, or an inactivated recombinant viral vaccine which is used to protect against infections caused by P. gingivalis. Vaccinia virus is the best known example, in the art, of an infectious virus that is engineered to express vaccine antigens derived from other organisms. The recombinant live vaccinia virus, which is attenuated or otherwise treated so that it does not caused disease by itself, is used to immunise the host. Subsequent replication of the recombinant virus within the host provides a continual stimulation of the immune system with the vaccine antigens such as the antigenic polypeptides, thereby providing long lasting immunity. In this context and below, 'vaccine' is not limited to compositions that raise a protective response but includes compositions raising any immune response.

Other live vaccine vectors include: adenovirus, cytomegalovirus, and preferably the poxviruses such as vaccinia (Paoletti and Panicali, U.S. Pat. No. 4,603,112) and attenuated salmonella strains (Stocker et al., U.S. Pat. Nos. 5,210,035; 4,837,151; and 4,735,801; and Curtis et al. et al., 1988, Vaccine 6: 155-160). Live vaccines are particularly advantageous because they continually stimulate the immune system which can confer substantially long-lasting immunity. When the immune response is protective against subsequent P. gingivalis infection, the live vaccine itself may be used in a protective vaccine against P. gingivalis. In particular, the live vaccine can be based on a bacterium that is a commensal inhabitant of the oral cavity. This bacterium can be transformed with a vector carrying a recombinant inactivated polypeptide and then used to colonise the oral cavity, in particular the oral mucosa. Once colonised the oral mucosa, the expression of the recombinant protein will stimulate the mucosal associated lymphoid tissue to produce neutralising antibodies. For example, using molecular biological techniques the genes encoding the polypeptides may be inserted into the vaccinia virus genomic DNA at a site which allows for expression of epitopes but does not negatively affect the growth or replication of the vaccinia virus vector. The resultant recombinant virus can be used as the immunogen in a vaccine formulation. The same methods can be used to construct an inactivated recombinant viral vaccine formulation except the recombinant virus is inactivated, such as by chemical means known in the art, prior to use as an immunogen and without substantially affecting the immunogenicity of the expressed immunogen.

As an alternative to active immunisation, immunisation may be passive, i.e. immunisation comprising administration of purified immunoglobulin containing an antibody against a polypeptide of the present invention.

The antigenic polypeptides used in the methods and compositions of the present invention may be combined with suitable excipients, such as emulsifiers, surfactants, stabilisers, dyes, penetration enhancers, anti-oxidants, water, salt solutions, alcohols, polyethylene glycols, gelatine, lactose, magnesium sterate and silicic acid. The antigenic polypeptides are preferably formulated as a sterile aqueous solution. The vaccine compositions of the present invention may be used to complement existing treatments for periodontal disease.

The invention also provides a method of preventing or treating a subject for periodontal disease comprising administering to the subject a vaccine composition according to the present invention. Also provided is an antibody raised against a polypeptide of the first aspect of the present invention. Preferably, the antibody is specifically directed against the polypeptides of the present invention.

In the present specification the term 'antibody' is used in the broadest sense and specifically covers monoclonal antibodies, polyclonal antibodies, multispecific antibodies (e.g., bispecific antibodies), chimeric antibodies, diabodies, triabodies and antibody fragments. The antibodies of the present invention are preferably able to specifically bind to an antigenic polypeptide as hereinbefore described without cross-reacting with antigens of other polypeptides.

The term 'binds specifically to' as used herein, is intended to refer to the binding of an antigen by an immunoglobulin variable region of an antibody with a dissociation constant (Kd) of 1 $\mu$M or lower as measured by surface plasmon resonance analysis using, for example a BIAcore™ surface plasmon resonance system and BIAcore™ kinetic evaluation software (eg. version 2.1). The affinity or dissociation constant (Kd) for a specific binding interaction is preferably about 500 nM to about 50 $\mu$M, more preferably about 500 nM or lower, more preferably about 300 nM or lower and preferably at least about 300 nM to about 50 pM, about 200 nM to about 50 pM, and more preferably at least about 100 nM to about 50 pM, about 75 nM to about 50 pM, about 10 nM to about 50 pM.

It has been shown that the antigen-binding function of an antibody can be performed by fragments of a full length antibody. Examples of binding fragments of an antibody include (I) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment which consists of a VH domain, or a VL domain; and (vi) an isolated complementarity determining region (CDR). Furthermore, although the two domains of the Fv fragment, VL and VH, are coded by separate genes, they can be joined, using recombinant methods, by a synthetic linker that enables them to be made as a single protein chain in which the VL and VH regions pair to form monovalent molecules (known as single chain Fv (scFv). Other forms of single chain antibodies, such as diabodies or triabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites.

Various procedures known in the art may also be used for the production of the monoclonal and polyclonal antibodies as well as various recombinant and synthetic antibodies which can bind to the antigenic polypeptides of the present invention. In addition, those skilled in the art would be familiar with various adjuvants that can be used to increase the immunological response, depending on the host species, and include, but are not limited to, Freud's (complete and incomplete), mineral gels such as aluminium hydroxide, surface active substances such as lysolecithin, pluronic polyols, polyanions, peptides, oil emulsions, dinitrophenol, and potentially useful human adjuvants such as *Bacillus* Calmette-Guerin (BCG) and *Corynebacterium parvum*. Antibodies and antibody fragments may be produced in large amounts by standard techniques (eg in either tissue culture or serum free using a fermenter) and purified using affinity columns such as protein A (eg for murine Mabs), Protein G (eg for rat Mabs) or MEP HYPERCEL (eg for IgM and IgG Mabs).

Recombinant human or humanized versions of monoclonal antibodies are a preferred embodiment for human therapeutic applications. Humanized antibodies may be prepared according to procedures in the literature (e.g. Jones et al. 1986, Nature 321: 522-25; Reichman et al. 1988 Nature 332: 323-27; et al. 1988, Science 1534-36). The recently described 'gene conversion metagenesis' strategy for the production of humanized monoclonal antibody may also be employed in the production of humanized antibodies (Carter et al. 1992 Proc. Natl. Acad. Sci. U.S.A. 89: 4285-89). Alternatively, techniques for generating the recombinant phase library of random combinations of heavy and light regions may be used to prepare recombinant antibodies (e.g. Huse et al. 1989 Science 246: 1275-81).

As used herein, the term 'antagonist' refers to a nucleic acid, peptide, antibody, ligands or other chemical entity which inhibits the biological activity of the polypeptide of interest. A person skilled in the art would be familiar with techniques of testing and selecting suitable antagonists of a specific protein, such techniques would including binding assays.

The antibodies and antagonists of the present invention have a number of applications, for example, they can be used as antimicrobial preservatives, in oral care products (toothpastes and mouth rinses) for the control of dental plaque and suppression of pathogens associated with dental caries and periodontal diseases. The antibodies and antagonists of the present invention may also be used in pharmaceutical preparations (eg, topical and systemic anti-infective medicines).

The present invention also provides interfering RNA molecules which are targeted against the mRNA molecules encoding the polypeptides of the first aspect of the present invention. Accordingly, in a seventh aspect of the present invention there is provided an interfering RNA molecule, the molecule comprising a double stranded region of at least 19 base pairs in each strand wherein one of the strands of the double stranded region is complementary to a region of an mRNA molecule encoding a polypeptide of the first aspect of the present invention.

So called RNA interference or RNAi is known and further information regarding RNAi is provided in Hannon (2002) *Nature* 418: 244-251, and McManus & Sharp (2002) *Nature Reviews: Genetics* 3(10): 737-747, the disclosures of which are incorporated herein by reference.

The present invention also contemplates chemical modification(s) of siRNAs that enhance siRNA stability and support their use in vivo (see for example, Shen et al. (2006) *Gene Therapy* 13: 225-234). These modifications might include inverted abasic moieties at the 5' and 3' end of the sense strand oligonucleotide, and a single phosphorthioate linkage between the last two nucleotides at the 3' end of the antisense strand.

It is preferred that the double stranded region of the interfering RNA comprises at least 20, preferably at least 25, and most preferably at least 30 base pairs in each strand of the double stranded region. The present invention also provides a method of treating a subject for periodontal disease comprising administering to the subject at least one of the interfering RNA molecules of the invention.

The compositions of this invention can also be incorporated in lozenges, or in chewing gum or other products, e.g. by stirring into a warm gum base or coating the outer surface of a gum base, illustrative of which are jelutong, rubber latex, vinylite resins, etc., desirably with conventional plasticizers or softeners, sugar or other sweeteners or such as glucose, sorbitol and the like.

In a further aspect, the present invention provides a kit of parts including (a) a composition of polypeptide inhibitory agent and (b) a pharmaceutically acceptable carrier. Desirably, the kit further includes instructions for their use for inhibiting biofilm formation in a patent in need of such treatment.

Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Throughout this specification the word 'comprise', or variations such as 'comprises' or 'comprising', will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. The invention specifically includes all combinations of features described in this specification.

In order that the nature of the present invention may be more clearly understood preferred forms thereof will now be described with reference to the following Examples.

Growth and Harvesting of P. gingivalis for Biofilm v Planktonic Studies

Porphyromonas gingivalis W50 (ATCC 53978) was grown in continuous culture using a model C-30 BioFlo chemostat (New Brunswick Scientific) with a working volume of 400 mL. Both the culture vessel and medium reservoir were continuously gassed with 10% $CO_2$ and 90% $N_2$. The growth temperature was 37° C. and the brain heart infusion growth medium (Oxoid) was maintained at pH 7.5. Throughout the entire growth, redox potential maintained at −300 mV. The dilution rate was 0.1 $h^{-1}$, giving a mean generation time (MGT) of 6.9 h. Sterile cysteine-HCl (0.5 g/L) and haemin (5 mg/L) were added. The culture reached steady state approximately 10 days after inoculation and was maintained for a further 30 days until a thick layer of biofilm had developed on the vertical surfaces of the vessel.

All bacterial cell manipulations were carried out on ice or at 4° C. During harvesting, the planktonic cells were decanted into a clean container and the biofilm washed twice gently with PGA buffer (10.0 mM $NaH_2PO_4$, 10.0 mM KCl, 2.0 mM, citric acid, 1.25 mM $MgCl_2$, 20.0 mM $CaCl_2$, 25.0 mM $ZnCl_2$, 50.0 mM $MnCl_2$, 5.0 mM $CuCl_2$, 10.0 mM $CoCl_2$, 5.0 mM$H_3BO_3$, 0.1 mM$Na_2MoO_4$, 10 mM cysteine-HCl with the pH adjusted to 7.5 with 5 M NaOH at 37° C.) followed by harvesting of the biofilm into a 50 mL centrifuge tube.

Planktonic and biofilm cells were then washed 3 times (7000 g) with PGA buffer and both samples resuspended to a final volume of 30 mL with wash buffer (50 mM Tris-HCl, 150 mM NaCl, 5 mM $MgCl_2$, pH 8.0, proteinase inhibitor inhibitor (Sigma)) and lysed by 3 passages through a French Press Pressure Cell (SLM, AMINCO) at 138 MPa. The lysed cells were centrifuged at 2000 g for 30 min to remove any unbroken cells. The supernatant was further centrifuged at 100000 g for 1 h to separate the lysed cells into their soluble and insoluble (cell envelope) fractions. The cell envelope fraction was further washed 3 times with wash buffer at 100000 g, for 20 min each to remove any soluble contaminations. All samples were then frozen and stored at −80° C.

Growth and Harvesting of P. gingivalis for Haem-Limitation and Excess Studies

P. gingivalis W50 was grown in continuous culture using a Bioflo 110 fermenter/bioreactor (New Brunswick Scientific) with a 400 mL working volume. The growth medium was 37 g/L brain heart infusion medium (Oxoid) supplemented with 5 mg/mL filter sterilized cysteine hydrochloride, 5.0 µg/mL haemin (haem-excess) or 0.1 µg/mL haemin (haem-limited). Growth was initiated by inoculating the culture vessel with a 24 h batch culture (100 mL) of P. gingivalis grown in the same medium (haem-excess). After 24 h of batch culture growth, the medium reservoir pump was turned on and the medium flow adjusted to give a dilution rate of 0.1 $h^{-1}$ (mean generation time (MGT) of 6.9 h). The temperature of the vessel was maintained at 37° C. and the pH at 7.4±0.1. The culture was continuously gassed with 5% $CO_2$ in 95% $N_2$. Cells were harvested during steady state growth, washed three times with wash buffer (50 mM Tris-HCl pH 8.0, 150 mM NaCl, 5 mM $MgCl_2$) at 5000 g for 30 min and disrupted with 3 passes through a French Pressure Cell (SLM, AMINCO) at 138 MPa. The lysed cells were then centrifuged at 2000 g for 30 min to remove unbroken cells followed by ultracentrifugation at 100000 g, producing a soluble (supernatant) and membrane fraction. All fractions were carried out on ice.

Preparation and Analysis of $^{18}O$ Proteolytic Labelled Biofilm and Planktonic Cell Envelope Fraction The cell envelope fraction was first resuspended in 1 mL of ice cold wash buffer containing 2% SDS, then sonication and vortexing were carried out to aid resuspension of the pellet. The final step in resuspension involved use of a 29-gauge-insulin needle to help break up particulates. The mixture was then centrifuged at 40000 g to remove insoluble particles and the protein concentration of the supernatant was determined using the BCA reagent (Pierce) according to the manufacturer's instructions.

The resuspended samples were subjected to precipitation using 5 volumes of ice cold acetone overnight at −20° C. which further helped to inactivate any proteolytic activity. After acetone precipitation, both samples were resuspended to a final concentration of 3 mg/mL with 25 mM Tris pH 8.0 and 1% SDS assisted by intermittent sonication, vortexing and the use of a 29-guage-insulin needle. A second BCA protein assay was then carried out to standardize the final protein amount.

Gel electrophoresis on a NuPAGE gel was carried out as per manufacturer's protocol using MOPs running buffer (NuPAGE, Invitrogen) except the samples were boiled at 99° C. for 5 min prior to loading onto a 10-well 10% NuPAGE gel with MOPs as the running buffer. The biofilm and planktonic samples (30 µg each) were loaded in adjacent lanes on the gel. SDS-PAGE was then carried out at 126 V (constant) at 4° C. until the dye front was approximately 1 cm from the bottom of the gel. For the biological replicate, the gel used was a 4-12% NUPAGE gradient gel using MOPs as the running buffer to give a similar but not exact pattern of separation so as to overcome the potential variation of a protein band being separated into two fractions. Staining was carried out overnight in Coomassie brilliant blue G-250 (31) followed by overnight destaining in ultrapure $H_2O$.

The two gel lanes were divided into 10 gel bands of equal sizes using a custom made stencil and each section cut into approximately 1 mm$^3$ cubes. Destaining was carried out 3 times in a solution of 50 mM $NH_4HCO_3$/ACN (1:1). After destaining, the gel cubes were dehydrated with 100% ACN, followed by rehydration/reduction with a solution of 10 mM dithiothreitol in ABC buffer (50 mM $NH_4HCO_3$) at 56° C. for 30 min. The excess solution was removed before adding 55 mM iodoacetamide in ABC buffer for 60 min at room temperature in the dark. After the alkylation reaction, the gel cubes were washed 3 times in ABC buffer, followed by dehydration twice in 100% ACN for 10 min. The gel cubes were further dried under centrifugation using a speedvac for 90 min. Digestion was carried out in 60 µL solution per gel section containing 2 µg of sequence grade modified trypsin (Promega) and ½ strength ABC buffer made up in either $H_2^{16}O$ or $H_2^{18}O$ ($H_2^{18}O$, >97% purity, Marshall Isotopes) for 20 h at 37° C. After digestion, the peptides were twice extracted from the gel using a solution of 50% ACN/0.1% TFA in their respective water ($H_2^{16}O$/$H_2^{18}O$) and 0.1% TFA with the aid of sonication for 5 min each. The pooled extract was boiled at 99° C. for 5 min to inactivate the trypsin followed by freeze drying for 48 h.

The freeze-dried peptides were resuspended in a solution of 5% ACN/0.1% TFA in their respective water ($H_2^{16}O$/$H_2^{18}O$) just before analysis using nanoHPLC and MALDI TOF-MS/MS analysis. The peptide solution (20 µL) was then loaded onto an Ultimate Nano LC system (LC Packings) using a FAMOS autosampler (LC Packings) in advanced µL pickup mode. The samples were first loaded onto a trapping column (300 µm internal diameter×5 mm) at 200 µL/min for 5 min. Separation was achieved using a reverse phase column (LC Packings, C18 PepMap100, 75 µm i.d.×15 cm, 3 µm, 100 Å) with a flow rate of 300 nL/min, and eluted in 0.1% formic acid with an ACN gradient of 0-5 min (0%), 5-10 min (0-16%), 10-90 min (16-80%), 90-100 min (80-0%).

Eluents were spotted straight onto pre-spotted anchorchip plates (Bruker Daltonics) using the Proteineer Fc robot (Bruker Daltonics) at 30 s intervals. Prior to spotting, each spot position was pre-spotted with 0.2 µL of ultrapure $H_2O$ to reduce the concentration of the acetonitrile during the crystallization process with the matrix. The plate was washed with 10 mM ammonium phosphate and 0.1% TFA and air-dried before automated analysis using a MALDI-TOF/TOF (Ultraflex with LIFT II upgrade, Bruker Daltonics). MS analysis of the digest was initially carried out in reflectron mode measuring from 800 to 3500 Da using an accelerating voltage of 25 kV. All MS spectra were produced from 8 sets of 30 laser shots, with each set needing to have a signal to noise, S/N>6, Resolution >3000 to be included. Calibration of the instrument was performed externally with [M+H]$^+$ ions of the prespotted internal standards (Angiotensin II, Angiotensin I, Neurotensin, Renin_substrate and ACTH_Clip) for each group of four samples. LIFT mode for MALDI-TOF/TOF was carried out in a fully automated mode using the Flexcontrol and WarpLC software (Bruker Daltonics). In the TOF1 stage, all ions were accelerated to 8 kV and subsequently lifted to 19 kV in the LIFT cell and all MS/MS spectra were produced from accumulating 550 consecutive laser shots. Selection of parent precursors was carried out using the WarpLC software (ver 1.0) with the LC MALDI SILE (Stable Isotope Labelling Experiment) work flow. Only the most abundant peak of each heavy or light pair separated by 4 Da was selected, providing its S/N was >50. Compounds separated by less than six LC MALDI fractions were considered the same and therefore selected only once.

Peak lists were generated using Flexanalysis 2.4 Build 11 (Bruker Daltonics) with the Apex peak finder algorithm with S/N>6. The MS scan was smoothed once with the Savitzky Golay algorithm using a width of 0.2 m/z and baseline subtraction was achieved using the Median algorithm with flatness of 0.8.

Protein identification was achieved using the MASCOT search engine (MASCOT version 2.1.02, Matrix Science) on MS/MS data queried against the *P. gingivalis* database obtained from The Institute for Genomic Research (TIGR) website (www.tigr.org). MASCOT search parameters were: charge state 1+, trypsin as protease, one missed cleavage allowed and a tolerance of 250 ppm for MS and 0.8 m/z for MS/MS peaks. Fixed modification was set for carbamidomethyl of cysteine and variable modification was C-terminal $^{18}O$ labelled lysine and arginine residues.

A reverse database strategy as described previously (32) was employed to determine the minimum peptide MASCOT score required to omit false positives for single peptide identification. Briefly, the database consists of both the sequence of every predicted *P. gingivalis* protein in its normal orientation and the same proteins with their sequence reversed (3880 sequences). The whole MS/MS dataset was then searched against the combined database to determine the lowest Mascot score to give 0% false positives. A false positive was defined as a positive match to the reversed sequence (bold red and above peptide threshold score). A false positive rate for single hit peptides was determined to be 0.5% with Mascot peptide ion scores of >threshold and <25. When the Mascot peptide ion score was >30, there was no match to the reverse database. In order to increase the confidence of identification for single hits peptide, we used a minimum Mascot peptide ion score of >50 which gives a two order of magnitude lower probability of incorrect identification than if a score of 30 was used, according to the Mascot scoring algorithm.

The matched peptides were evaluated using the following criteria, i) at least 2 unique peptides with a probability based score corresponding to a p-value <0.05 were regarded as positively identified (required bold red matches) where the score is −log×10 log(P) and P is the probability that the observed match is a random event (33), ii) where only one unique peptide was used in the identification of a specific protein (identification of either heavy or light labelled peptide is considered as one) the MASCOT peptide ion score must be above 50 or that peptide is identified in more than one of the four independent experiments (2 biological replicates and 2 technical replicates).

Due to the mixed incorporation of one or two $^{18}O$ atoms into the peptides, the contribution of the natural abundance of the $^{18}O$ isotope and the $H_2^{18}O$ purity (a=0.97), the ratios of the peptides R were mathematically corrected using equation:

$$R = (I_1 + I_2)/I_0 \qquad (1)$$

$I_0$, $I_1$ and $I_2$ were calculated according to the following equations (27), $$I_1 = \frac{aS_2 - [aJ_2 - 2(1-a)J_4]S_0 - 2(1-a)S_4}{a^2 - (2-a-a^2)J_2 + 2(1-a)^2 J_4} \qquad (2)$$

$$I_0 = S_0 - (1-a)I_1 \qquad (3)$$

-continued $$I_2 = \frac{1}{a^2}(S_4 - J_4 I_0 - J_2 I_1) \quad (4)$$

Where $S_0$, $S_2$ and $S_4$ are the measured intensities of the monoisotopic peak for peptide without $^{18}O$ label, the peak with 2 Da higher than the monoisotopic peak, and the peak with 4 Da higher than the monoisotopic peak respectively (FIG. 1A). $J_0$, $J_2$ and $J_4$ are the corresponding theoretical relative intensities of the isotopic envelope of the peptide calculated from MS-Isotope (http://prospector.ucsf.edu). However when the intensity of the second isotopic peaks ($S_1$ and $S_5$) was more intense than the first isotopic peaks ($S_0$ and $S_4$), the ratio was simply calculated as $S_1$ divided by $S_5$. This was true especially for large peptides above 2000 m/z where the contribution of the fifth isotopic peak of the $^{16}O$ labelled peptide to the $S_4$ peak becomes significant. Calculation of mixed 16O18O incorporation was determined by the difference in the experimental $S_2$ and theoretical $S_2$ ($J_2$) as a percentage of experimental $S_4$.

Protein abundance ratios were determined by averaging all identified peptides of the same protein, even when the same protein was identified in more than one gel section. The data from each 'normal' replicate was combined with the inversed ratios from its respective 'reverse' replicate providing an average ratio and standard error for each protein in each biological replicate. Normalization of both the biological replicates was then carried out similarly to that previously reported (34,35). Briefly the averaged ratio for each biological replicate was multiplied by a factor so that the geometric mean of the ratios was equal to one.

Preparation and Analysis of ICAT Labelled Haem-Limited and Excess Cells

Protein labelling and separation were based on the geLC-MS/MS approach (Li et al., 2003) using the cleavable ICAT reagent (Applied Biosystems). Another proteomic approach has been taken in PCT/AU2007/000890 which is herein incorporated by reference. Protein was first precipitated using TCA (16%) and solubilised with 6 M urea, 5 mM EDTA, 0.05% SDS and 50 mM Tris-HCl pH 8.3. Protein concentration was determined using the BCA protein reagent and adjusted to 1 mg/ml. 100 µg of protein from each growth condition was individually reduced using 2 µL of 50 mM Tris(2-carboxy-ethyl)phosphine hydrochloride for 1 h at 37° C. Reduced protein from the haem-limitation growth condition was then alkylated with the $ICAT_{heavy}$ reagent and protein from haem-excess growth condition with the $ICAT_{light}$ reagent. The two samples were then combined and subjected to SDS-PAGE on a precast Novex 10% NUPAGE gel (Invitrogen). The gel was stained for 5 min using SimplyBlue™ SafeStain (Invitrogen) followed by destaining with water. The gel lane was then excised into 20 sections from the top of the gel to the dye front.

The excised sections were further diced into 1 mm³ cubes and in-gel digested overnight and extracted twice according to the above procedure. The pooled supernatant was dried under reduced vacuum to about 50 µL followed by mixing with 500 µL of affinity load buffer before loading onto the affinity column as per manufacturer's instruction (Applied Biosystems). Eluted peptides were dried and the biotin tag cleaved with neat TFA at 37° C. for 2 h followed by drying under reduced vacuum. The dried samples were suspended in 35 µL of 5% acetonitrile in 0.1% TFA.

MS was carried out using an Esquire HCT ion trap mass spectrometer (Bruker Daltonics) coupled to an UltiMate Nano LC system (LC Packings—Dionex). Separation was achieved using a LC Packings reversed phase column (c18 PepMap100, 75 µm i.d.×15 cm, 3 µm, 100 Å), and eluted in 0.1% formic acid with the following acetonitrile gradient: 0-5 min (0%), 5-10 min (0-10%), 10-100 min (10-50%), 100-120 min (50-80%), 120-130 min (80-100%).

The LC output was directly interfaced to the nanospray ion source. MS acquisitions were performed under an ion charge control of 100000 in the m/z range of 300-1500 with maximum accumulation time of 100 ms. When using GPF three additional m/z ranges (300-800, 700-1200 and 1100-1500) were used to select for precursor ions and each m/z range was carried out in duplicate to increase the number of peptides identified. MS/MS acquisition was obtained over a mass range from 100-3000 m/z and was performed on up to 10 precursors for initial complete proteome analysis and 3 for ICAT analysis for the most intense multiply charged ions with an active exclusion time of 2 min.

Peak lists were generated using DataAnalysis 3.2 (Bruker Daltonics) using the Apex peak finder algorithm with a compound detection threshold of 10000 and signal to noise threshold of 5. A global charge limitation of +2 and +3 were set for exported data. Protein identification was achieved using the MASCOT search engine (MASCOT 2.1.02, Matrix Science) on MS/MS data queried against the *P. gingivalis* database obtained from The Institute for Genomic Research (TIGR) website (www.tigr.org). The matched peptides were further evaluated using the following criteria, i) peptides with a probability based Mowse score corresponding to a p-value of at most 0.05 were regarded as positively identified, where the score is $-\log \times 10(\log(P))$ and P is the probability that the observed match is a random event ii) where only one peptide was used in the identification of a specific protein and the MASCOT score was below 30, manual verification of the spectra was performed. To increase confidence in the identification of ICAT-labelled proteins especially for those with single peptide hits, additional filters were applied as follows: i) the heavy and light peptides of an ICAT pair must have exhibited closely eluting peaks as determined from their extracted ion chromatograms ii) for proteins with a single unique peptide, this peptide must have been identified more than once (e.g in different SDS-PAGE fractions or in both the light and heavy ICAT forms iii) if a single peptide did not meet the criteria of (ii), the MASCOT score must have been ≥25, the expectation value≤0.01 and the MS/MS spectrum must have exhibited a contiguous series of 'b' or 'y'-type ions with the intense ions being accounted. Determinations of false positives were as described above.

The ratio of isotopically heavy $^{13}C$ to light $^{12}C$ ICAT labelled peptides was determined using a script from DataAnalysis (Bruker Daltonics) and verified manually based on measurement of the monoisotopic peak intensity (signal intensity and peak area) in a single MS spectrum. The minimum ion count of parent ions used for quantification was 2000 although >96% of both heavy and light precursor ions were >10000. In the case of poorly resolved spectra, the ratio was determined from the area of the reconstructed extracted ion chromatograms (EIC) of the parent ions. Averages were calculated for multiple peptides derived from a single parent protein and outliers were removed using the Grubb's test with $\alpha = 0.05$.

The cellular localization of *P. gingivalis* proteins was predicted using CELLO (http://cello.life.nctu.edu.tw (36)). Extracellular, outer membrane, inner membrane and periplasmic predictions were considered to be from the envelope fraction.

The concentrations of short-chain fatty acids (SCFA) in cell-free culture supernatants (uninoculated, haem-excess and haem-limited) were determined by capillary gas chromatography based on the derivatization method of Richardson et al. (37).

The correlation coefficient (r) between both biological replicates was evaluated using the Pearson correlation coefficient function from Microsoft Excel. The coefficient of variance (CV) was calculated by the standard deviation of the peptide abundance ratios divided by the mean, expressed as a percentage.

Extraction of Nucleic Acids for Transcriptomic Analysis

RNA was extracted from 5 mL samples of *P. gingivalis* cells harvested directly from the chemostat. To each sample 0.2 volumes of RNA Stabilisation Reagent (5% v/v phenol in absolute ethanol) were added. Cells were pelleted by centrifugation (9000 g, 5 min, 25° C.), immediately frozen in liquid nitrogen and stored at −70° C. for later processing. Frozen cells were suspended in 1 mL of TRIzol reagent (Invitrogen) per $1 \times 10^{10}$ cells and then disrupted using Lysing Matrix B glass beads (MP Biomedicals) and the Precellys 24 homogeniser (Bertin Technologies, France). The glass beads were removed by centrifugation and the RNA fraction purified according to the TRIzol manufacturer's (Invitrogen) protocol, except that ethanol (at a final concentration of 35%) rather than isopropanol was added at the RNA precipitation stage and samples were then transferred to the spin-columns from the Illustra RNAspin Mini RNA Isolation kit (GE Healthcare). RNA was purified according to the manufacturer's instructions from the binding step onwards, including on-column DNAse treatment to remove any residual DNA. RNA integrity was determined using the Experion automated electrophoresis station (Bio-Rad).

Genomic DNA was extracted from *P. gingivalis* cells growing in continuous culture using the DNeasy Blood & Tissue Kit (Qiagen) in accordance with the manufacturer's instructions.

Microarray Design, Hybridization and Analysis

Microarray slides were printed by the Australian Genome Research Facility and consisted of 1977 custom designed 60-mer oligonucleotide probes for the predicted protein coding regions of the *P. gingivalis* W83 genome including additional protein coding regions predicted by the Los Alamos National Laboratory Oralgen project. Microarray Sample Pool (MSP) control probes were included to aid intensity-dependent normalisation. The full complement of probes was printed 3 times per microarray slide onto Corning UltraGAPS coated slides.

Slides were hybridised using either haeme-excess or heme-limited samples labelled with Cy3, combined with a universal genomic DNA reference labelled with Cy5 (GE Lifesciences). cDNA was synthesized from 10 μg of total RNA using the SuperScript plus indirect cDNA labelling system (Invitrogen), with 5 μg of random hexamers (Invitrogen) for priming of the cDNA synthesis reaction. cDNA was labelled with Cy3 using the Amersham CyDye post-labelling reactive dye pack (GE Lifesciences) and purified using the purification module of the Invitrogen labelling system. Cy5-dUTP labelled genomic cDNA was synthesized in a similar manner from 400 ng of DNA, using the BioPrime Plus Array CGH Indirect Genomic Labelling System (Invitrogen).

Prior to hybridisation, microarray slides were immersed for 1 h in blocking solution (35% formamide, 1% BSA, 0.1% SDS, 5×SSPE [1×SSPE is 150 mM NaCl, 10 mM $NaH_2PO_4$, 1 mM EDTA]) at 42° C. After blocking slides were briefly washed in $H_2O$ followed by 99% ethanol and then dried by centrifugation. Labelled cDNAs were resuspended in 55 μL of hybridization buffer (35% formamide, 5×SSPE, 0.1% SDS, 0.1 mg $mL^{-1}$ Salmon Sperm DNA) denatured at 95° C. for 5 min then applied to slides and covered with LifterSlips (Erie Scientific). Hybridisation was performed at 42° C. for 16 h. Following hybridisation slides were successively washed in 0.1% SDS plus 2×SSC [1×SSC is 150 mM NaCl 15 mM sodium citrate] (5 min at 42° C., all further washes performed at room temperature), 0.1% SDS plus 0.1×SSC (10 min), 0.1×SSC (4 washes, 1 min each), and then quickly immersing in 0.01×SSC, then 99% ethanol and using centrifugation to dry the slides.

Slides were scanned using a GenePix 4000B microarray scanner and images analysed using GenePix Pro 6.0 software (Molecular Devices). Three slides were used for each treatment (haeme-limitation or haeme-excess) representing three biological replicates.

Image analysis was performed using the GenePix Pro 6.0 software (Molecular Devices), and "morph" background values were used as the background estimates in further analysis. To identify differentially expressed genes the LIMMA software package was used with a cut off of $P<0.005$. Within array normalisation was performed by fitting a global loess curve through the MSP control spots and applying the curve to all other spots. The Benjamini Hochberg method was used to control the false discovery rate to correct for multiple testing.

Gene predictions were based on the *P. gingvalis* W83 genome annotation from the The Institute for Genomic Research (TIGR, www.tigr.org). Operon prediction was carried out from the Microbesonline website (http://microbesonline.org)

Response of *P. Gingivalis* to Haeme-Limitation as Determined Using DNA Microarray Analysis A DNA microarray analysis of the effect of haeme-limited growth on *P. gingivalis* global gene expression was carried out under identical growth conditions employed for the proteomic analysis. Analysis of data from three biological replicates identified a total of 160 genes that showed statistically significant differential regulation between haeme-excess and haeme-limitation, with the majority of these genes showing increased levels of expression under conditions of heme-limitation and only 8 genes being down-regulated. Many of the up-regulated genes were predicted to be in operons and the majority of these showed similar changes in transcript levels (Table 3 and 5). There was broad agreement between the transcriptomic and proteomic data with a significant correlation between the two data sets where differential regulation upon haeme-limitation was observed [Spearman's correlation 0.6364, $p<0.05$]. However for some of the proteins showing differences in abundance from the proteomic analysis, the transcriptomic analysis of the corresponding genes did not detect any statistically significant differences in the abundance of the mRNA. The microarray analyses tended to identify only those genes encoding proteins that had large changes in abundance as determined by the proteomic analysis (Tables 3 and 5). Where protein and transcript from the same gene were found to be significantly regulated by haeme-limitation the majority showed the same direction of regulation. The exceptions were two gene products, PG0026 a CTD family putative cell surface proteinase and PG2132 a fimbrillin (FimA). These proteins decreased in abundance in the proteomic analysis under haeme-limitation but were predicted to be up-regulated by the transcriptomic analysis. Both these proteins are cell surface located and it is quite possible that they are either released from the cell surface or post-translationally modified which could preclude them from being identified as up-regulated in the proteomic analysis.

In addition to the gene products discussed in more detail below transcription of several genes of interest were significantly up-regulated including the genes of a putative operon of two genes, PG1874 and PG1875, one of which encodes Haemolysin A; eight concatenated genes PG1634-PG1641 of which PG1638 encodes a putative thioredoxin and PG1043 that encodes FeoB2, a manganese transporter. PG1858 which encodes a flavodoxin was the most highly up-regulated gene at 15.29-fold. Of the 152 significantly up-regulated genes ~55 have no predicted function.

Continuous Culture and Biofilm Formation

*P. gingivalis* W50 was cultured in continuous culture over a 40 day period during which the cell density of the culture remained constant after the first 10 days with an OD650 of 2.69±0.21 and 2.80±0.52 for biological replicates 1 and 2 respectively. This equates to a cell density of ~3 mg cellular dry weight/mL. Over this time period a biofilm of *P. gingivalis* cells developed on the vertical glass wall of the fermenter vessel. This biofilm was ~2 mm thick at the time of harvest.

Validation of $^{16}O/^{18}O$ Quantification Method Using BSA

Figure 1B:

To determine the accuracy and reproducibility of the $^{16}O/^{18}O$ quantification method, known amounts of BSA were loaded onto adjacent gel lanes to give ratios of 1:1, 1:2, 1:5 and 10:1 (FIG. 1B). The bands were subjected to in-gel tryptic digestion in the presence of either $H_2^{16}O$ or $H_2^{18}O$, mixed and then analyzed by LC MALDI-MS/MS. A typical set of spectra for a single BSA tryptic peptide across the four ratios shows the preferential incorporation of two $^{18}O$ atoms, which is seen most clearly by the predominance of the +4 Da peak in the 10:1 BSA ratio, and by the almost symmetrical doublet in the 1:1 spectrum, simplifying both quantification and identification (FIG. 1A). The average incorporation of a single $^{18}O$ atom was estimated to be <7% based on the 1:1 labelling (Supplementary Table). The calculated average ratios for all identified BSA peptides were 0.98±0.12, 2.22±0.26, 4.90±0.75 and 10.74±2.04 for ratios of 1:1 (triplicate), 2:1 (and 1:2), 1:5 and 10:1, respectively indicating a good dynamic range, high accuracy of ±2-11% and a low CV ranging from 11.75% to 18.95% (Table 1). The reproducible accuracy of the 1:1 mixture (performed in triplicate) implies that labelling bias was very low. This was further confirmed by comparing normal and reverse labelled BSA at a 2:1 ratio, using only peptides that were identified in both experiments. The normal ratio was determined to be 2.11±0.33 while the reverse was 2.30±0.20 (Table 1).

Experimental Design for Quantitative Analysis of Biofilm and Planktonic Samples

The design of this study involved the use of two biological replicates, that is two independent continuous cultures, each one split into a biofilm sample obtained from the walls of the vessel, and a planktonic sample obtained from the fluid contents of the vessel. Two technical replicates for each biological replicate were performed, and although we had established that there was no significant labelling bias with BSA, we chose to utilize the reverse labelling strategy as there is a lack of $^{16}O/^{18}O$ labelling validation studies that have been conducted on complex biological samples (30). Therefore in total there were four experiments, each consisting of 10 LC-MALDI MS/MS runs stemming from 2×10 gel segments.

Figure 2A:
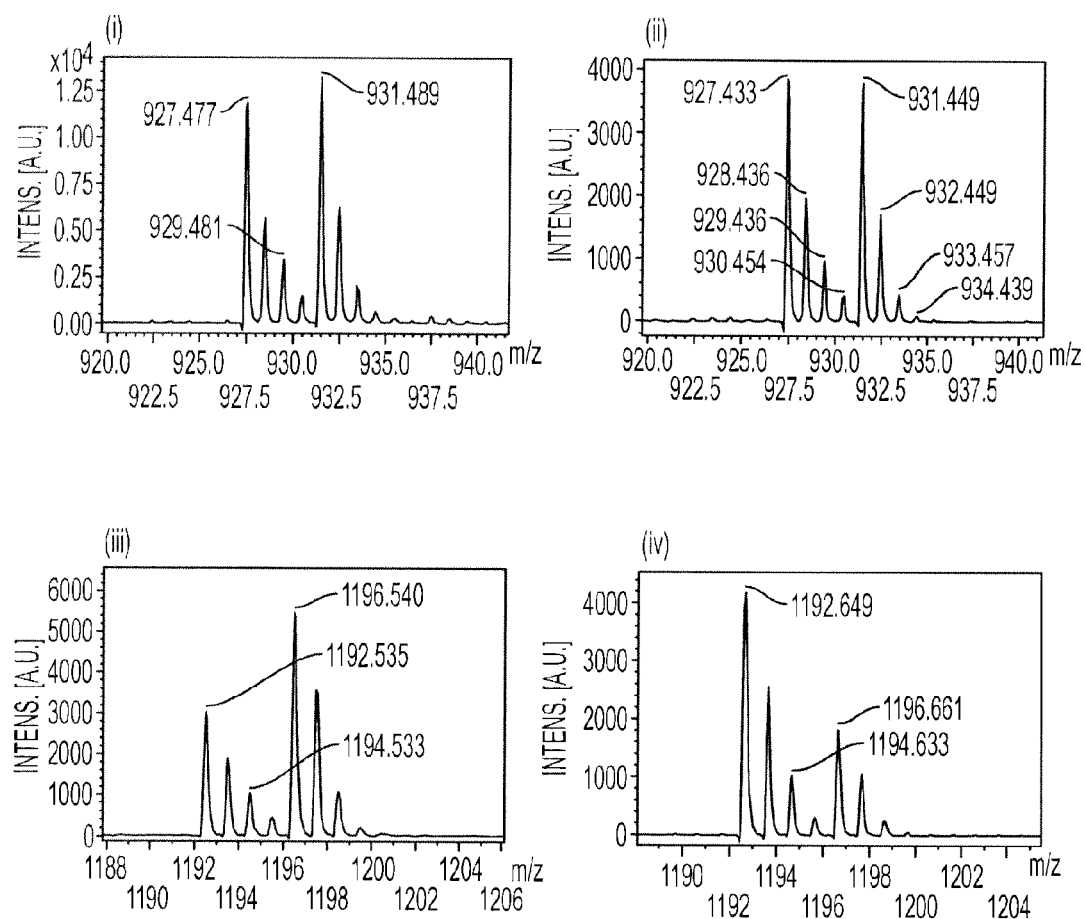
FIGS. 2A and 2B: Typical forward and reverse MS and MS/MS spectra from *P. gingivalis* sample. (i,ii) Zoomed portion of mass spectra showing the [M+H]+ parent precursor ion of the normal and reverse labelled peptide GNLQALVGR (SEQ ID NO: 2) belonging to PG2082 and showing the typical 4 Da mass difference in a 1:1 ratio (iii,iv) mass spectrum showing the [M+H]+ parent precursor ion of the normal and reverse labelled peptide YNANNVDLNR (SEQ ID NO: 3) belonging to PG0232 and showing the typical 4 Da mass difference in a 2:1 ratio (v, vi) MS/MS spectrum of heavy labelled (+2 18O) YNANNVDLNR (SEQ ID NO: 3) and unlabelled YNANNVDLNR (SEQ ID NO: 3) peptide characterized by the 4 Da shift of all Y ions.
Figure 2B:
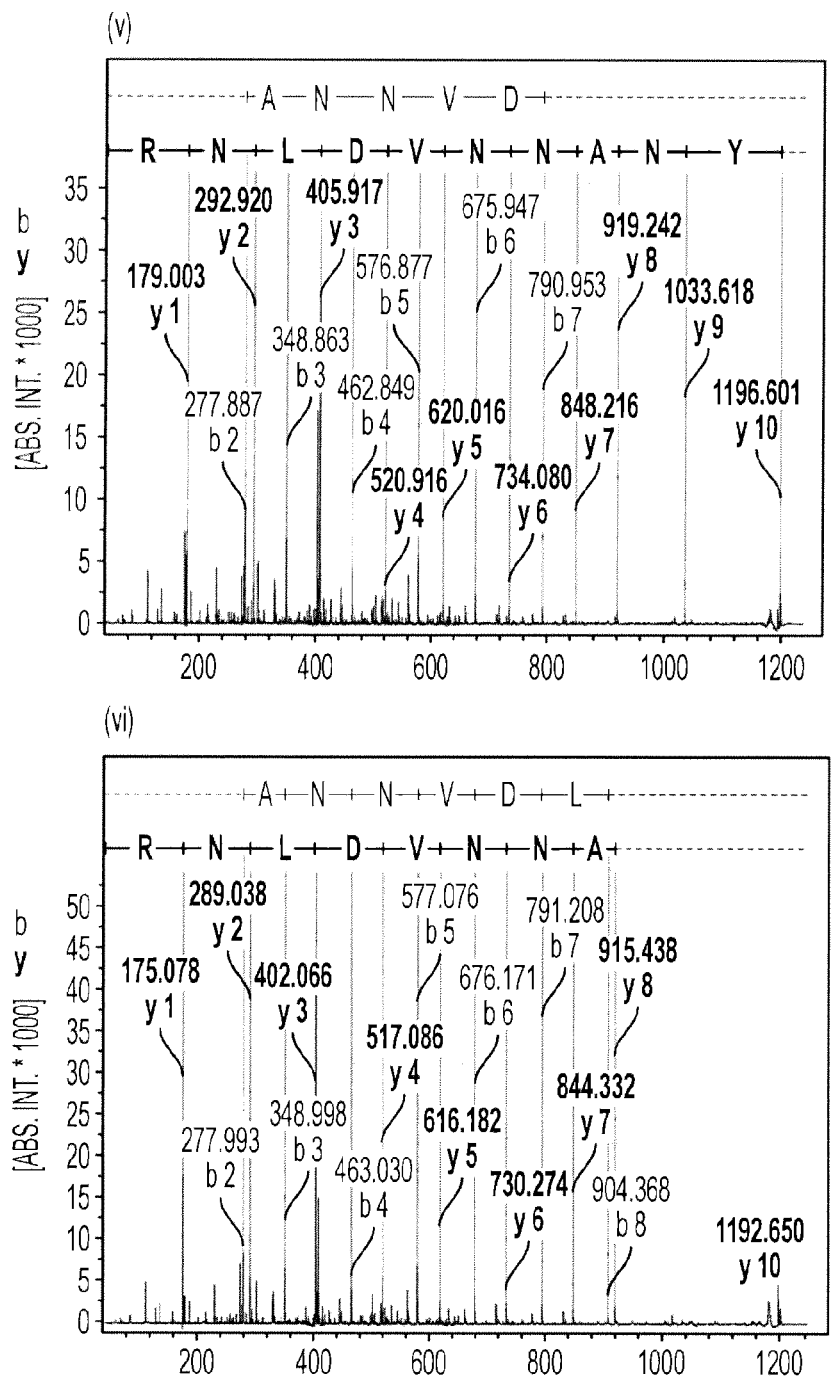

FIG. 2 shows typical MS and MS/MS spectra of two normal and reverse labelled peptides from the biofilm/planktonic samples illustrating the typical reverse labelling pattern. As with the BSA data, it could be seen that there was a high level of double $^{18}O$ incorporation with the average mixed incorporation calculated to be <15% for all peptides, confirming that the $^{16}O/^{18}O$ proteolytic labelling method was also effective with complex samples (data not shown). The predominance of doubly labelled peptides was further confirmed by the relatively few Mascot hits to the +2 Da species. MS/MS spectra of the heavy labelled peptides further revealed the expected +4 Da shifts in the Y ions (FIG. 2).

Figure 5:
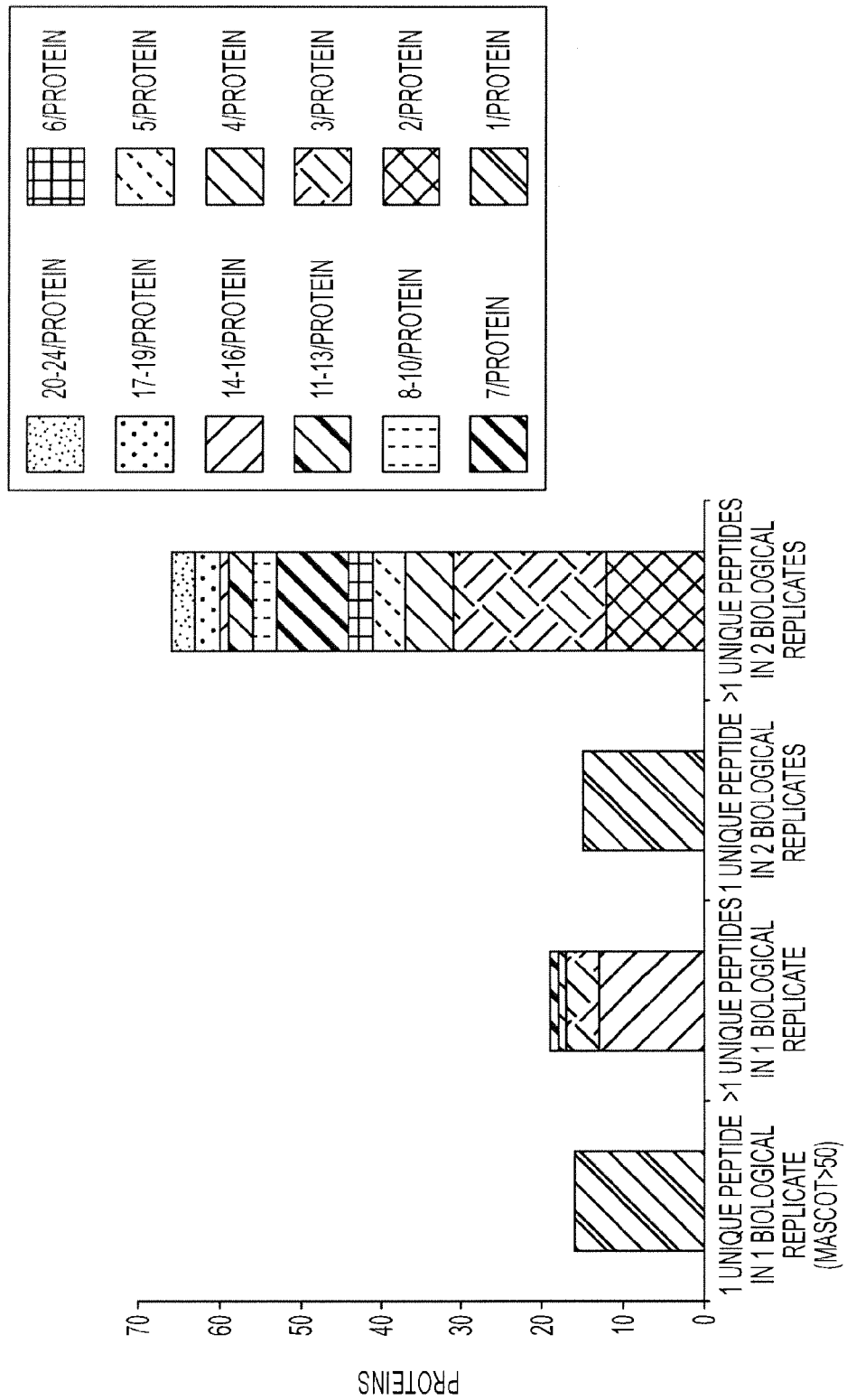
FIG. 5: Breakdown of the 116 proteins identified in this study based on identification in one or both biological replicates and number of unique peptides identified. The proteins identified from both biological replicates (81) are presented in table 2. Legend shows number of unique peptides identified per protein.

The Cell Envelope Proteome of Planktonic and Mature Biofilm *P. Gingivalis* Cells We have identified and determined the relative abundance of 116 proteins from 1582 peptides based on the selection criteria described in the experimental procedures section. Of the proteins identified, 73.3% were identified by more than 2 unique peptides, 12.9% were from 1 unique peptide but identified in both biological replicates and 13.8% were identified only by 1 unique peptide with Mascot peptide ion score of >50 (FIG. 5). CELLO (36) predicted 77.6% of these proteins to be from the cell envelope thereby showing the effectiveness of this cell envelope enrichment method. Bioinformatics classification by TIGR (www.tigr.org) and ORALGEN oral pathogen sequence databases (www.oralgen.lanl.gov) predicted a large percentage of the identified proteins to be involved in transport, have proteolytic activities, or cell metabolism functions. Interestingly 55% of all identified proteins were of unknown functions.

Figure 3A:
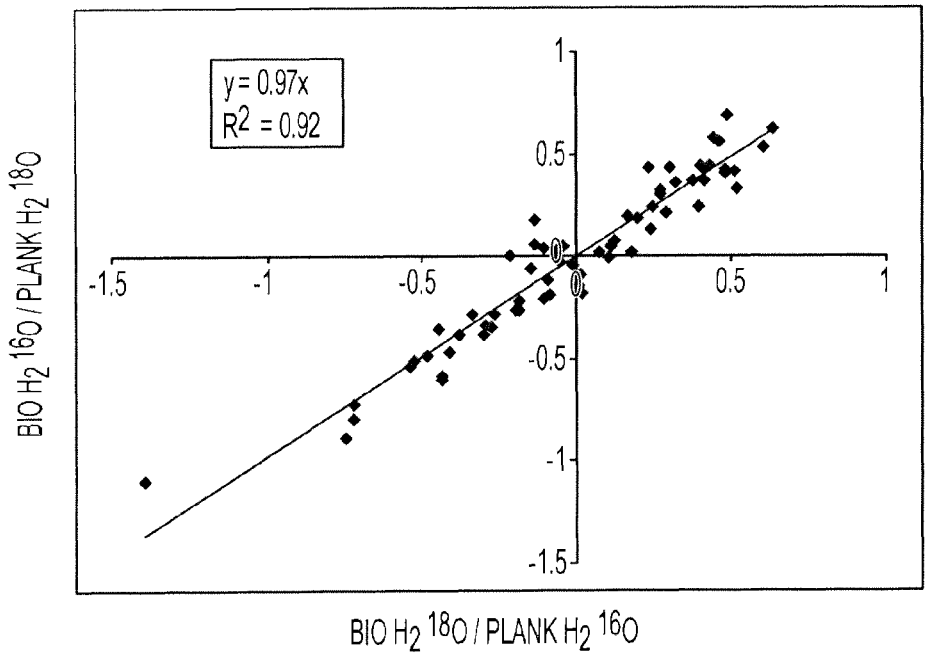
FIGS. 3A and 3B: Correlation of normal/reverse labelled technical replicates. Log 10 transformed scatter plot comparison of peptide abundance ratio of the normal (Bio18, Plank16) and reverse (Plank18, Bio16) labelling for both biological replicates. The abundance ratios of the reverse labelled peptides have been inversed for a direct comparison.
Figure 3B:
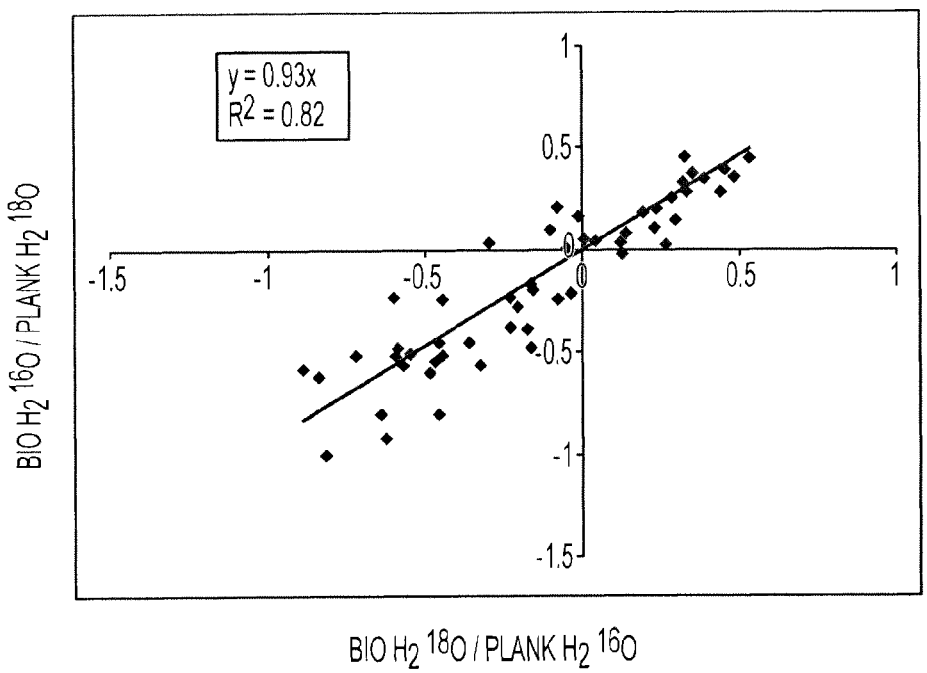

To compare technical replicates of the biological data, the $Log_{10}$ transformed protein abundance ratios of each pair of normal and reverse labelled experiments were plotted against each other (FIG. 3). Linear regression of these plots indicated that each pair is highly correlated with $R^2$ values of 0.92 and 0.82 for biological replicate 1 and 2, respectively. The slope of each linear fit was also similar to the expected value of 1.0 at 0.97 and 0.93 for biological replicate 1 and 2, respectively indicating no labelling bias between the technical replicates (FIG. 3). The protein abundance ratios from the technical replicates were averaged to give a single ratio for each biological replicate.

Figure 4A:
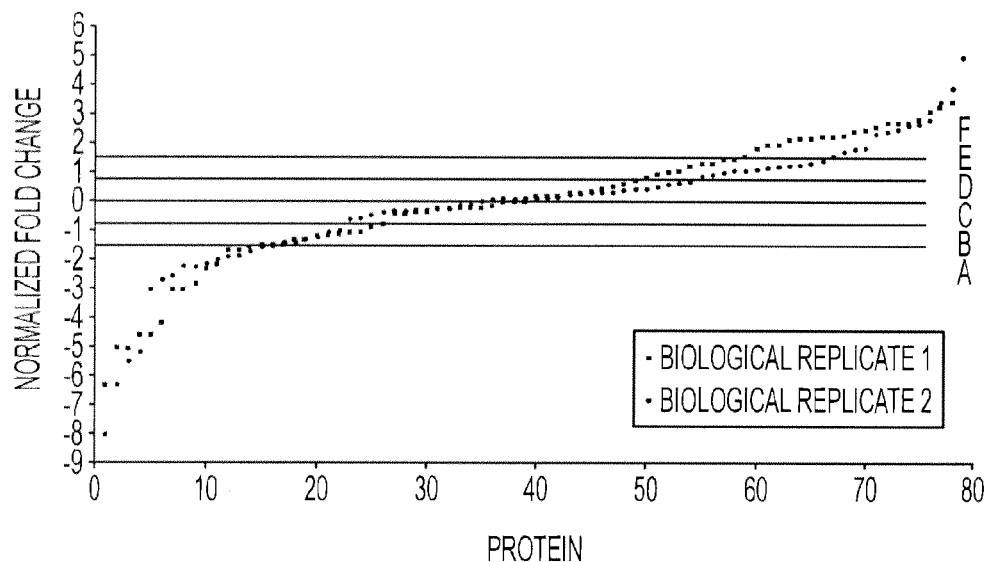
FIGS. 4A and 4B: Distribution and correlation of protein abundances of biological replicates.
Figure 4B:
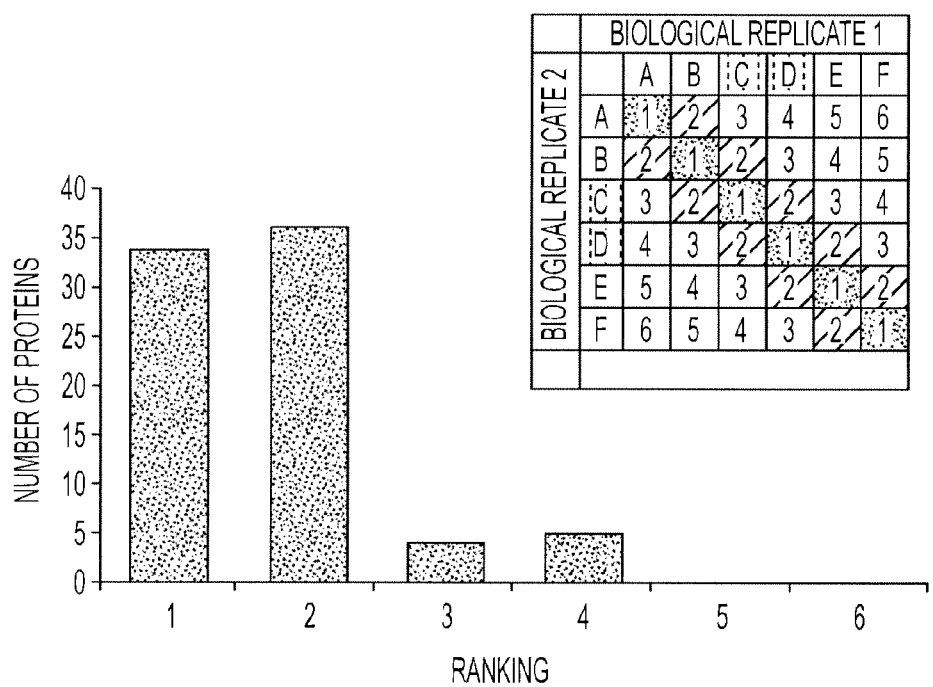

Before comparing the average data for the two biological replicates, the protein abundance ratios of each biological replicate were normalized to give an average mean ratio of 1.0. A plot of the normalized protein abundance ratios from both the biological replicates exhibits a Gaussian-like distribution closely centered at zero (FIG. 4A) similar to that described by others (40,41). There was a significant positive correlation between the two biological replicates (Pearson's correlation coefficient r=0.701, p<0.0001) indicating that the growth of the biofilm/planktonic cultures and all downstream processing of the samples could be reproduced to a satisfactory level. To determine which proteins were consistently regulated in the two biological replicates, a simple ranking chart was constructed where proteins were divided into 6 groups (A-F) according to their abundance ratio and then ranked 1-6 according to group-based correlation, with those ranked 1 having the highest similarity when a protein from both biological replicates fell within the same group (FIG. 4B). Using the ranking chart, we were able to determine that 34 out of 81 (42%) of the proteins identified from both replicates were ranked number one, considerably higher than the value expected for a random correlation which would be 17% (or ⅙). The majority of the remaining proteins were ranked number two, and therefore in total, 70 proteins (86.4%) were considered to be similarly regulated between the two experiments (ranked 1 or 2; Table 2).

Based on the measured standard deviation (±0.26) of the 2:1 BSA labelling experiment (Table 1), protein abundance changes were deemed to be biologically significant when they differed from 1.0 by >3 standard deviations (either >1.78 or <0.56) (18,42). Using this criteria, the abundance of 47 out of the 81 proteins identified in both replicates were significantly changed (based on the average ratios), and of these, 42 were ranked either 1 or 2 (Table 2). Of the 42 proteins ranked 1 and 2, 24 had significantly increased in abundance and 18 had decreased in abundance.

Enzymes of Metabolic Pathways Showing Co-Ordinated Regulation

Twenty proteins involved in the glutamate/aspartate catabolism were identified in the haem-limited vs haem-excess study using ICAT labelling strategies (Table 3). Of those, enzymes catalyzing six of the eight steps directly involved in the catabolism of glutamate to butyrate were identified and found to have increased 1.8 to 4 fold under haem-limitation (Table 3). Although the other two catalytic enzymes (PG0690, 4-hydroxybutyrate CoA-transferase and PG1066, butyrate-acetoacetate CoA-transferase) were not detected using ICAT, they were found to be present in a separate qualitative study at comparable high ion intensities to those proteins reported in Table 3 (not shown) and belong to operons shown to be upregulated. On the other hand, the effect of haem-limitation on the abundances of the enzymes of the aspartate catabolic pathway was mixed, with the enzymes catalyzing the breakdown of aspartate to oxaloacetate in the oxidative degradation pathway being unchanged and the enzymes involved in the conversion of pyruvate to acetate showing an increase of 2 to 4.4 fold.

The abundance of two iron containing fumarate reductase enzymes, FrdA (PG1615) and FrdB (PG1614) that together catalyse the conversion of fumarate to succinate via the reductive pathway from aspartate, was significantly reduced in cells cultured in haem-limitation (Table 3). These two proteins, that are encoded in an operon (Baughn et al., 2003), show similar changes in abundance in response to haem-limitation (FrdA L/E=0.35; FrdB L/E=0.25).

Analysis of Organic Acid End Products

The amounts of acetate, butyrate and propionate in the spent culture medium of *P. gingivalis* grown under haem limitation were 13.09±1.82, 7.77±0.40 and 0.71±0.05 mmole/g cellular dry weight, respectively. Levels of acetate, butyrate and propionate in the spent culture medium of *P. gingivalis* grown in haem excess were 6.00±0.36, 6.51±0.04 and 0.66±0.07 mmole/g cellular dry weight, respectively.

The above results illustrate the changes in protein abundance that occur when planktonic *P. gingivalis* cells adhere to a solid surface and grow as part of a mature monospecies biofilm. It is the first comparative study of bacterial biofilm versus planktonic growth to utilize either the geLC MS approach of Gygi's group (46) or the $^{16}O/^{18}O$ proteolytic labelling method to determine changes in protein abundances as all other such studies published to date have utilized 2D gel electrophoresis based methods (10-12). A two technical replicate and two biological replicate $^{16}O/^{18}O$ reverse labelling approach was successfully employed to quantitate and validate the changes in protein abundance.

Continuous Culture of *P. Gingivalis*

In this study *P. gingivalis* W50 was cultured in continuous culture as opposed to the more traditional methodology of batch culture. Batch culture introduces a large range and degree of variation into bacterial analyses due to interbatch variables such as: size and viability of the inoculum, exact growth stage of the bacterium when harvested, levels of available nutrients in the medium and redox potential of the medium, amongst other factors. In continuous culture the bacterium is grown for many generations under strictly controlled conditions that include growth rate, cell density, nutrient concentrations, temperature, pH and redox potential. (44, 47,48). A previous study has demonstrated a high level of reproducibility of *Saccharomyces cerevisiae* transcriptomic analyses continuously cultured in chemostats in different laboratories (49). Furthermore in our study the growth of both biofilm and planktonic cells was carried out in a single fermentation vessel, reducing variability as compared to separate cultivations. The consistent changes in *P. gingivalis* cell envelope protein abundances between biological replicates of 86.4% of the identified proteins (ranked 1 and 2) seen in this study illustrate the applicability of the continuous culture system and the $^{16}O/^{18}O$ proteolytic labelling strategy to the analysis of the effect of biofilm growth on the *P. gingivalis* proteome.

Efficiency of $^{18}O$ Labelling

The basic proteomic method employed in this study was the geLC MS method (46,50) due to the high resolution and solubility of membrane proteins that the SDS-PAGE method affords. This method was combined with a single $^{18}O$ labelling reaction during the in-gel digestion procedure similar to that described by others (26-29). Efficient labelling should result in the incorporation of two $^{18}O$ atoms into the C-terminus of each peptide and should be resistant to back-exchange with $^{16}O$. This was found to be the case in our study with BSA where the level of single $^{18}O$ atom incorporation was estimated to be <7% and the mean ratios obtained for various BSA experiments were found not to significantly favour $^{16}O$ (Table 1) suggesting that back exchange with normal water was not a problem. Similar results were also obtained for the biological samples. A crucial step for efficient $^{18}O$ labelling was the need for the complete removal of the natural $H_2^{16}O$ followed by resolubilization of the protein in $H_2^{18}O$ before tryptic digestion employing a 'single-digestion' method. Although a number of studies have used a 'double digestion' method (51,52), the single digestion method has the advantage of giving a higher efficiency of $^{18}O$ labelling as in the double digestion method some tryptic peptides were unable to exchange either of their C-terminal $^{16}O$ atoms for an $^{18}O$ atom after the initial digestion (53). We further utilized an in-gel digestion method where the protein is retained in the gel matrix during the initial dehydration step using organic solvents as in any standard in-gel digestion protocol. Complete removal of any trace natural $H_2^{16}O$ was achieved through lyophilization by centrifugation under vacuum while the protein was still within the gel matrix to prevent further adsorptive losses during the initial lyophylization step. Rehydration and in-gel digestion was carried out in $H_2^{18}O$ containing a large excess of trypsin which was also reconstituted in $H_2^{18}O$. During the digestion procedure, tryptic peptides liberated from the gel after the incorporation of the first $^{18}O$ atom can undergo the second carbonyl oxygen exchange process mediated by the excess trypsin. This should promote the replacement of the second carbonyl oxygen since peptides liberated would have higher solubility than proteins thereby resulting in a higher level of doubly $^{18}O$ labelled tryptic peptides (FIGS. 1 and 2; (54)). In order to prevent back exchange with normal water, trypsin was deactivated by boiling which has been previously shown to be effective (51,54). In addition, the dried, deactivated mix was only resuspended and mixed immediately prior to injection onto a nanoLC to minimize spontaneous exchange, although this spontaneous exchange has been shown to be low (15,40).

Reverse Labelling

In the case of stable isotope labelling and quantification using MS, errors are potentially introduced during the labelling and ionization process. These errors include the potential different affinity of the label and the possible suppression effect of the heavy or light labelled peptides during the MALDI process (13,55). Traditional technical replicates which involve repeating the same labelling could result in an uncorrected bias towards a particular label or increased random error of specific peptides due to contaminating peaks. Our normal and reverse labelled technical replicates demonstrated a high degree of correlation with scatter plot gradients of 0.97 ($R^2$=0.92) and 0.93 ($R^2$=0.82) for biological replicates 1 and 2, respectively (FIG. 3) which is close to the expected ratio of 1.0 for no labelling bias. These gradients also indicate that the method was reproducible with respect to protein estimation, gel loading, gel excision and in-gel digestion. The lack of bias suggests normalization routines like dye swap or LOWESS data normalization routinely used in microarray experiments (35) might be unnecessary. However samples that are considerably more complex than the bacterial cell envelopes used in this study may still require reverse labelling validation as when one considers the influence of minor contaminating peptides on the calculation of the $^{18}O/^{16}O$ ratios and the need to verify peptides with extreme changes. The reverse-label design in addition to providing an estimate and means for correcting systematic errors had the further benefit of allowing both the heavy and light labelled peptides to be readily identified since the MS/MS acquisition method selected only the most intense peptide in each heavy/light pair to fragment. In this way the possibility of incorrect assignment is reduced. To our knowledge, this is the first report of reverse $^{16}O/^{18}O$ labelling in a complex biological sample other than the recent quantitation of seventeen cytochrome P450 proteins (26,30).

Biofilm vs Planktonic Culture

We have demonstrated a strong positive correlation between the biological replicates (r=0.701, p<0.0001) indicating that there was reproducibility in biofilm formation and development. This was also seen by the finding that 70 out of 81 quantifiable proteins were observed to exhibit similar ratios in both biological replicates (Table 2, ranked 1 or 2). More than three quarters of the *P. gingivalis* proteins identified in this study were identified by >2 unique peptides, further increasing the confidence of identification and quantification of this labelling procedure. Of the 81 proteins consistently identified from both biological replicates, 47 significantly changed in abundance from the planktonic to biofilm state. The change in abundance of a percentage of the detected proteome, especially in the cell envelope, is consistent with other studies on biofilm forming bacteria such as *Pseudomonas aeruginosa*, where over 50% of the detected proteome was shown to exhibit significant changes in abundance between planktonic and mature biofilm growth phases. (12). We further observed a wide range of responses in the cell envelope proteome of *P. gingivalis* to growth as a biofilm. A number of proteins previously demonstrated to be altered in abundance in response to biofilm culture were also found to have changed in abundance in our study. Remarkably some proteins were observed to have changed in abundance by up to fivefold (Table 2) suggesting some major shifts in the proteome in response to biofilm culture.

C-Terminal Domain family

*P. gingivalis* has recently been shown to possess a novel family of up to 34 cell surface-located outer membrane proteins that have no significant sequence similarities apart from a conserved C-Terminal Domain (CTD) of approximately 80 residues (31,56). The *P. gingivalis* CTD family of proteins includes the gingipains (RgpA [PG2024], RgpB [PG0506], Kgp [PG1844]); Lys- and Arg-specific proteinases and adhesins, that are secreted and processed to form non-covalent complexes on the cell surface and are considered to be the major virulence factors of this bacterium (57-61). Gingipains have been linked directly to disease pathogenesis due to their ability to degrade host structural and defense proteins and the inability of mutants lacking functional Kgp or RgpB to cause alveolar bone loss in murine periodontal models (62). Although these CTD family proteins have a variety of functions the known and putative functions of the CTD family proteins are strongly focused towards adhesive and proteolytic activities and also include the CPG70 carboxypeptidase (63), PrtT thiol proteinase, HagA haemagglutinin, *S. gordonii* binding protein (PG0350, (64)) a putative haemagglutinin, putative thiol reductase, putative fibronectin binding protein, putative Lys-specific proteinase (PG0553) and a putative von Willebrand factor domain protein amongst others. The majority of these proteins are likely to play important roles in the virulence of the bacterium as they are involved in extracellular proteolytic activity, aggregation, haem/iron capture and storage, biofilm formation and maintenance, virulence and resistance to oxidative stress. The CTD has been proposed to play roles in the secretion of the proteins across the outer membrane and their attachment to the surface of the cell, probably via glycosylation (56,65,66). In this work we were able to quantify nine CTD family proteins consistently regulated in both replicates (Table 2) and all except PG2216 and PG1844 (Kgp) had increased in abundance during the biofilm state. The significant increase in the abundance of many of this group of proteins therefore suggests they play important functional roles during the biofilm state.

The major cell surface proteases of *P. gingivalis* RgpA, Kgp are known to be actively involved in peptide and haem acquisition, especially from haemoglobin and the release of haem at the cell surface (67,68). During the biofilm state, there was an average 2.7 fold increase in the abundance of RgpA. HagA which contains the adhesin domains that are also found in RgpA and Kgp that are responsible for haemagglutination and hemoglobin binding of *P. gingivalis* (69) was also higher in abundance in the biofilm state.

Kgp in contrast was observed to be significantly lower in abundance in biofilm cells of *P. gingivalis*. This could be due to a decrease in Kgp abundance or may be due to the release of Kgp from the *P. gingivalis* cell surface during biofilm culture. Kgp is essential for *P. gingivalis* to hydrolyze haemoglobin at surface-exposed Lys residues which leads to the release and uptake of peptides and haem (67,70). The adhesion domains of Kgp are involved in haemoglobin binding and Genco et al (70) have proposed that Kgp acts as a haemophore, that like siderophores, is released from the cell surface to scavenge haem from the environment. Kgp with bound haem is then proposed to bind to HmuR, an outer membrane TonB-linked receptor, reported to be required for both haemoglobin and haem utilization and deliver haem to the cell (71). Interestingly, HmuY a protein that is encoded in an operon with HmuR, was also more abundant in biofilm cultured cells.

The hmu locus contains 6 genes (hmuYRSTUV) and has been suggested to belong to the multigenic cluster encoding proteins involved in the haem-acquisition pathways similar to the Iht and Htr systems (72). HmuY was shown to be required for both haemoglobin and haem utilization and is regulated by iron availability (72,73). Although HmuR was not identified in our study, the operonic nature of hmuR and hmuY and other evidence suggests that their expression is similarly regulated and they act in concert for haem utilization (71,74). The decrease in abundance of Kgp and the increase in abundance of HmuY is therefore consistent with its proposed role as a hemophore and haem limitation in biofilm growth (see below).

CPG70 (PG0232) a CTD family protease that has been demonstrated to be involved in gingipain processing was also consistently higher in abundance in biofilm culture possibly indicating a role in the remodeling of cell surface proteins during biofilm growth (63,75). A CTD family putative thioredoxin (PG0616) was also significantly higher in abundance in the biofilm state. PG0616 has been characterized as HBP35, a haem binding protein having coaggregation properties (76). Of particular note was the increased abundance of the immunoreactive 46 kDa antigen, PG99 by an average factor of 5.0 in biofilm cells (Table 2). This was the highest observed increase in protein abundance in this study, and since PG99 is both immunogenic and a CTD family member and therefore most probably located on the cell surface, this protein represents a good potential target for biofilm disruptive agents.

Transport Proteins

Two putative TonB dependent receptor family proteins (PG1414 and PG2008) and a putative haem receptor protein (PG1626) also show significant increase in abundance. The exact functions of these proteins are unknown, however a COG search on the NCBI COG database resulted in hits to the P functional class of outer membrane receptor proteins involving mostly Fe transport (77). Interestingly we also observed an increased abundance of the intracellular iron storage protein ferritin (PG1286). The consistent increases in abundance of these iron/haem transporting and storage proteins could be an indication of haem/iron limitation, especially within the deeper layers of the biofilm since ferritin is important for *P. gingivalis* to survive under iron-depleted conditions (78).

It is likely that both haemoglobin and haem would not diffuse far into the biofilm due to the high proteolytic activity, high haemoglobin and haem binding and storage capacities of *P. gingivalis*. It is also possible that ferrous iron transport via FeoB1 plays a more important role in the iron metabolism of this species in the deeper layers of the biofilm which may also explain the increase in ferritin as there would be little chance of cell surface storage of iron as haem (45,79). *P. gingivalis* grown under conditions of haem limitation exhibits an increase in intracellular iron, indicating that PPIX is the growth limiting factor and that ferrous iron is accumulated via the FeoB1 transporter (45).

IhtB (PG0669) and a putative TonB dependent receptor (PG0707) both showed a decrease in abundance in the biofilm state (Table 2). IhtB is a haem binding lipoprotein that also has been proposed to function as a peripheral outer membrane chelatase that removes iron from haem prior to uptake by *P. gingivalis* (80). A similar decrease in abundance of two proteins potentially involved in haem/Fe uptake during the biofilm state that coincided with an increase in abundance of many others indicates a shift in either the types of receptors being used for uptake or more likely a change in the substrate being used. Taken together from the above observations, it appears that *P. gingivalis* growing in a biofilm is likely to be haem starved. The higher abundance of some transport and binding proteins therefore suggests them being more crucial during the biofilm state and thus possible antimicrobial drug targets.

There is a higher abundance of the glycolytic enzyme glyceraldehyde 3-phosphate dehydrogenase (GAPDH) during the biofilm state compared to the planktonic which is consistent with previous results obtained for *Listeria monocytogenes* and *Pseudomonas aeruginosa* (12,106). Although GAPDH is classified as a tetrameric NAD-binding enzyme involved in glycolysis and gluconeogenesis, there have been numerous reports of this protein being multifunctional and when expressed at the cell surface of Gram-positive bacteria, it appeared to be involved in binding of plasmin, plasminogen and transferrin (107,108). Interestingly coaggregation between *Streptococcus oralis* and *P. gingivalis* 33277 has been shown to be mediated by the interaction of *P. gingivalis* fimbriae and *S. oralis* GAPDH (109). The exact role, if any, of GAPDH in substrate binding in *P. gingivalis* however remains to be answered.

Biofilm Formation

There was a significantly higher abundance of the universal stress protein (UspA) in the planktonic cells as compared to the biofilm cells. The production of Usp in various bacteria was found to be stimulated by a large variety of conditions, such as entry into stationary phase, starvation of certain nutrients, oxidants and other stimulants (110,111). The increased abundance in planktonic phase cells is consistent with the fact that *P. gingivalis* has evolved to grow as part of a biofilm and that planktonic phases are likely to be more stressful. Expression of UspA in *P. gingivalis* is thought to be related to biofilm formation as inactivation of uspA resulted in the attenuation of early biofilm formation by planktonic cells (112). In this study the biofilm has been established and reached maturation, it therefore appears to have lesser need for UspA as compared to free floating planktonic cells.

A homologue of the internalin family protein InlJ (PG0350) was observed to be higher in abundance during the biofilm state. PG0350 has been shown to be important for biofilm formation in *P. gingivalis* 33277 as gene inactivation resulted in reduced biofilm formation (39). Higher levels of PG0350 in the biofilm could suggest that this protein might be required not just for initial biofilm formation but acts an adhesin that binds *P. gingivalis* to each other or extracellular substrates within the biofilm.

Proteins with Unknown Functions

The largest group of proteins identified in this study was 41 proteins with unknown functions including four proteins that were identified for the first time in this study (Table 2). Of the 41 proteins identified, 37 were predicted to be from the cell envelope and within this group 17 proteins show significant changes between the biofilm and planktonic cells. The majority of these proteins have homology to GenBank proteins with defined names but not well-defined functions. Of particular interest are several proteins that were consistently found to substantially increase in abundance in the biofilm state, namely PG0181, PG0613, PG1304, PG2167 and PG2168.

The above results represent a large scale validation of the $^{16}O/^{18}O$ proteolytic labelling method as applied to a complex mixture, and are the first to use this approach for the comparison of bacterial biofilm and planktonic growth states. A substantial number of proteins with a variety of functions were found to consistently increase or decrease in abundance in the biofilm cells, indicating how the cells adapt to biofilm conditions and also providing potential targets for biofilm control strategies.

TABLE 1

Quantification of predetermined BSA ratios using $^{16}O/^{18}O$ proteolytic labelling

| Expected ratio 1:1a) | Triplicate analysis | | | Mean ratio (±SD) |
|---|---|---|---|---|
| CCTESLVNR (SEQ ID NO: 4) | 0.83 | 0.84 | 0.88 | 0.85 ± 0.03 |
| DLGEEHFK (SEQ ID NO: 5) | 0.95 | 1.06 | 0.85 | 0.95 ± 0.10 |
| EACFKVEGPK (SEQ ID NO: 6) | 1.09 | 1.12 | 1.09 | 1.10 ± 0.02 |
| ECCDKPLLEK (SEQ ID NO: 7) | 1.01 | 0.96 | 0.87 | 0.94 ± 0.07 |
| EYEATLEECCAK (SEQ ID NO: 8) | 1.05 | 1.01 | 1.05 | 1.04 ± 0.02 |
| LVTDLTKVHK (SEQ ID NO: 9) | 0.86 | 0.91 | 1.02 | 0.93 ± 0.08 |
| RHPEYAVSVLLR (SEQ ID NO: 1) | 1.07 | 0.96 | 0.94 | 0.99 ± 0.07 |
| YICDNQDTISSK (SEQ ID NO: 10) | 1.00 | 1.15 | 1.03 | 1.06 ± 0.08 |
| Average | 0.98 ± 0.10 | 1.00 ± 0.10 | 0.97 ± 0.09 | 0.98 ± 0.08 |
| Average of all peptides ID** | | | | 0.98 ± 0.12 |
| CV of all peptides ID | | | | 13.1% |

| | Expected ratio 2:1 b) (18O/16O) | Expected ratio 1:2 b) (18O/16O) | |
|---|---|---|---|
| QTALVELLK (SEQ ID NO: 11) | 1.92 | 0.44 (2.27) | 2.10 |
| LVNELTEFAK (SEQ ID NO: 12) | 2.45 | 0.46 (2.17) | 2.31 |
| RHPEYAVSVLLR (SEQ ID NO: 1) | 1.82 | 0.42 (2.36) | 2.09 |
| LGEYGFQNALIVR (SEQ ID NO: 13) | 2.21 | 0.43 (2.31) | 2.26 |
| MPCTEDYLSLILNR (SEQ ID NO: 14) | 2.59 | 0.40 (2.50) | 2.55 |
| KVPQVSTPTLVEVSR (SEQ ID NO: 15) | 2.35 | 0.39 (2.57) | 2.46 |
| LFTFHADICTLPDTEK (SEQ ID NO: 16) | 1.72 | 0.44 (2.27) | 2.00 |
| RPCFSALTPDETYVPK (SEQ ID NO: 17) | 1.82 | 0.52 (1.92) | 1.87 |
| Average | 2.11 ± 0.33 | 2.30 ± 0.20 | 2.24 ± 9.24 |
| Average of all peptides ID*** | | | 2.22 ± 0.26 |
| CV of all peptides ID | | | 11.75% |

| Expected ratio 1:5 | | Expected ratio 10:1 | |
|---|---|---|---|
| | (18O/16O) | | (18O/16O) |
| AEFVEVTK (SEQ ID NO: 18) | 0.232 (4.32) | AEFVEVTK (SEQ ID NO: 18) | 12.38 |
| CCTESLVNR (SEQ ID NO: 4) | 0.184 (5.42) | QTALVELLK (SEQ ID NO: 11) | 10.40 |
| SHCIAEVEK (SEQ ID NO: 20) | 0.176 (5.67) | LVNELTEFAK (SEQ ID NO: 12) | 14.17 |
| ECCDKPLLEK (SEQ ID NO: 21) | 0.169 (5.91) | FKDLGEEHFK (SEQ ID NO: 29) | 9.41 |
| HPEYAVSVLLR (SEQ ID NO: 22) | 0.218 (4.58) | HPEYAVSVLLR (SEQ ID NO: 22) | 11.76 |
| YICDNQDTISSK (SEQ ID NO: 23) | 0.187 (5.36) | YICDNQDTISSK (SEQ ID NO: 23) | 10.16 |
| LKECCDKPLLEK (SEQ ID NO: 24) | 0.252 (3.97) | RHPEYAVSVLLR (SEQ ID NO: 1) | 10.14 |
| SLHTLFGDELCK (SEQ ID NO: 25) | 0.183 (5.45) | SLHTLFGDELCK (SEQ ID NO: 25) | 7.58 |
| RHPEYAVSVLLR (SEQ ID NO: 1) | 0.201 (4.97) | EYEATLEECCAK (SEQ ID NO: 8) | 14.07 |
| VPQVSTPTLVEVSR (SEQ ID NO: 26) | 0.206 (4.86) | ETYGDMADCCEK (SEQ ID NO: 30) | 12.67 |
| ECCHGDLLECADDR (SEQ ID NO: 27) | 0.298 (3.35) | LGEYGFQNALIVR (SEQ ID NO: 13) | 9.36 |
| LFTFHADICTLPDTEK (SEQ ID NO: 28) | 0.210 (4.76) | VPQVSTPTLVEVSR (SEQ ID NO: 26) | 8.34 |
| | | KVPQVSTPTLVEVSR (SEQ ID NO: 15) | 8.86 |
| | | LFTFHADICTLPDTEK (SEQ ID NO: 16) | 11.08 |
| | | RPCFSALTPDETYVPK (SEQ ID NO: 17) | 10.26 |
| Average | 0.210 ± 0.04 (4.90 ± 0.75) | | 10.74 ± 2.04 |
| CV of all peptides ID | 15.26% | | 18.95% | a) For expected ratio of 1:1, only peptides that were identified in all three separate experiments are included in this table
b) For expected ratio of 2:1 and 1:2, only peptides that were identified in both experiments are included in this table
n = 55   *n = 24

TABLE 2

List of the 81 proteins identified from both biological replicates of the *P. gingivalis* cell envelope fraction. An abundance ratio of >1 indicates a higher abundance of the protein in the biofilm with respect to the planktonic state. If the ratio differs from one with more than 3-fold SD (0.26) from the predetermined BSA ratios (>1.78 or <0.56), the proteins were considered to have significantly changed. Based on their mean ratios, proteins highlighted in grey represent significant changes.

| | | | Biological replicate 1 | | | | Biological replicate 2 | | | | | |
|---|---|---|---|---|---|---|---|---|---|---|---|---|
| Tigr # | Protein | Loca | # peptide for quant | Mascot scoreb | Norm Ratio (B/P)c | SEd | # peptide for quant | Mascot score | Norm Ratio (B/P) | SE | Total unique peptides | Rank (Group)e |
| CTD family proteins | | | | | | | | | | | | |
| | Proteinases | | | | | | | | | | | |
| PG0232 | Zinc carboxypeptidase, CPG70 | OM | 13 | 71/20 | 1.67 | 0.08 | 26 | 74/21 | 2.53 | 0.08 | 15 | 3 (DF) |
| PG0553 | Extracellular protease, lysyl endopeptidase precursor (API) | OM/EX | 1 | 65/23 | 3.33 | | 2 | 62/19 | 3.45 | | 2 | 1 (FF) |
| PG1424 | Peptidylarginine deminase | PP | 9 | 86/22 | 0.49 | 0.05 | 15 | 89/20 | 3.16 | 0.33 | 10 | 4 (BF) |
| PG1837 | Hemagglutinin protein HagA | OM | 3 (15)* | 59/20 | 2.73 | 0.44 | 3 (15)* | 42/21 | 4.21 | 0.36 | 3 | 1 (FF) |
| PG1844 | Lysine-specific cysteine proteinase | OM | 3 (13)* | 78/20 | 0.43 | 0.04 | 9 (24)* | 77/18 | 0.40 | 0.04 | 10 | 1 (BB) |
| PG2024 | Arginine-specific protease ArgI polyprotein (RgpA) | OM | 3 (12)* | 76/22 | 1.63 | 0.10 | 3 (22)* | 72/20 | 3.78 | 0.61 | 4 | 3 (DE) |
| | Haem binding | | | | | | | | | | | |
| PG0616 | Thioredoxin, putative | PP/CY | 14 | 96/20 | 2.23 | 0.20 | 14 | 96/20 | 3.69 | 0.20 | 6 | 2 (EF) |
| | Biofilm related | | | | | | | | | | | |
| PG0350 | Internalin-related protein | OM/EX | 2 | 42/21 | 1.99 | | 2 | 53/21 | 4.27 | | 3 | 2 (EF) |
| | Protein with unknown functions | | | | | | | | | | | |
| PG1798 | Immunoreactive 46 kDa antigen PG99 | PP/EX | 1 | 36/20 | 5.94 | | 1 | 30/21 | 4.07 | | 1 | 1 (FF) |
| PG2216 | Unnamed protein (conserved) | OM/EX | 2 | 36/22 | 0.72 | NA | 4 | 51/21 | 0.68 | 0.06 | 3 | 1 (CC) |
| Transport | | | | | | | | | | | | |
| PG0669 | Haem binding protein IhtB | OM | 16 | 120/21 | 0.25 | 0.03 | 14 | 69/20 | 0.16 | 0.02 | 6 | 1 (AA) |
| PG0707 | TonB-dependent receptor, P92 | OM | 5 | 110/21 | 0.14 | 0.02 | 30 | 117/20 | 0.31 | 0.04 | 17 | 1 (AA) |
| PG0782 | MotA/TolQ/ExbB proton channel family protein | IM | 7 | 80/19 | 0.86 | 0.14 | 4 | 78/19 | 0.92 | 0.12 | 7 | 1 (CC) |
| PG1006 | Putative TonB dependent receptor | OM/EX | 6 | 59/21 | 1.42 | 0.12 | 9 | 90/20 | 1.50 | 0.11 | 7 | 1 (DD) |
| PG1414 | TonB linked outer membrane receptor, PG47 | OM | 11 | 88/21 | 3.81 | 0.43 | 3 | 49/19 | 3.69 | NA! | 7 | 1 (FF) |

TABLE 2-continued

List of the 81 proteins identified from both biological replicates of the *P. gingivalis* cell envelope fraction. An abundance ratio of >1 indicates a higher abundance of the protein in the biofilm with respect to the planktonic state. If the ratio differs from one with more than 3-fold SD (0.26) from the predetermined BSA ratios (>1.78 or <0.56), the proteins were considered to have significantly changed. Based on their mean ratios, proteins highlighted in grey represent significant changes.

| | | | | | | | | | | | |
|---|---|---|---|---|---|---|---|---|---|---|---|
| PG1551 | HmuY protein | UN | 4 | 75/20 | 2.57 | 0.71 | 4 | 74/20 | 2.78 | 0.21 | 1 | 1 (DD) |
| PG1626 | Possible outer membrane-associated protein P58 (putative haem receptor protein) | OM | 41 | 113/21 | 2.37 | 0.22 | 37 | 122/19 | 3.68 | 0.26 | 17 | 2 (EF) |
| PG2008 | TonB-dependent receptor, P90 | OM | 24 | 68/21 | 2.08 | 0.17 | 26 | 112/20 | 3.12 | 0.21 | 20 | 2 (EF) |
| PG0185 | RagA protein | OM | 58 | 89/21 | 0.42 | 0.02 | 109 | 126/20 | 0.79 | 0.04 | 24 | 2 (BC) |
| PG0186 | Lipoprotein RagB | OM | 51 | 142/22 | 0.34 | 0.04 | 56 | 142/19 | 0.26 | 0.02 | 24 | 1 (AA) |
| PG1010 | ABC transporter, ATP- binding protein | IM | 1 | 69/21 | 1.41 | | 2 | 60/19 | 1.26 | | 2 | 1 (DD) |
| PG1762 | Protein-export membrane protein SecD/ protein-export membrane protein SecF | IM | 14 | 91/22 | 0.76 | 0.07 | 4 | 99/20 | 0.48 | 0.09 | 10 | 2 (CB) |
| PG2082 | POT family protein | IM | 13 | 75/23 | 0.80 | 0.06 | 6 | 48/22 | 0.52 | 0.10 | 4 | 1 (CC) |
| Iron/haem storage and oxidative stress response | | | | | | | | | | | | |
| PG0090 | Dps family protein | CY | 3 | 72/19 | 1.37 | 0.15 | 1 | 40/21 | 1.27 | | 2 | 1 (DD) |
| PG1286 | Ferritin | CY | 5 | 73/22 | 1.50 | 0.04 | 7 | 124/19 | 2.42 | 0.14 | 3 | 2 (DE) |
| Biofilm and invasion related | | | | | | | | | | | | |
| PG0159 | Endopeptidase PepO | PP/CY | 8 | 122/20 | 0.35 | 0.08 | 3 | 60/19 | 0.18 | NA! | 3 | 2 (BA) |
| PG0245 | Universal stress protein family | CY | 1 | 67/22 | 0.41 | | 2 | 64/20 | 0.25 | | 1 | 2 (BA) |
| PG2132 | Fimbrilin | EX | 1 | 31/22 | 1.14 | | 2 | 66/20 | 0.85 | | 3 | 2 (DC) |
| Energy Metabolism | | | | | | | | | | | | |
| PG0249 | Oxaloacetate decarboxylase, putative | CY | 1 | 44/22 | 3.50 | | 1 | 37/21 | 2.00 | | 1 | 2 (FE) |
| PG0306 | Electron, transport complex, RnfABCDGE type, G subunit | PP | 2 | 108/22 | 1.08 | | 1 | 61/19 | 0.72 | | 1 | 2 (DC) |
| PG1084 | Thioredoxin family protein | CY | 2 | 87/22 | 1.07 | | 1 | 132/20 | 0.14 | | 1 | 4 (DA) |
| PG1612 | Methylmalonyl-CoA decarboxylase, alpha subunit (mmdA) | CY | 1 | 65/21 | 0.73 | | 2 | 55/21 | 0.42 | | 1 | 2 (CB) |
| PG1614 | Fumarate reductase, iron-sulfur protein (frdB) | UN | 2 | 60/20 | 0.15 | | 2 | 53/21 | 0.19 | | 2 | 1 (AA) |
| PG1615 | Fumarate reductase, flavoprotein subunit (frdA) | UN | 3 | 58/19 | 0.06 | NA! | 1 | 43/20 | NA** | | 3 | NA |
| PG1704 | Thiol:disulfide interchange protein dsbD, putative | IM | 3 | 64/23 | 2.14 | | 3 | 68/20 | 0.46 | 0.08 | 1 | 4 (EB) |
| PG2181 | NADH:ubiquinone oxidoreductase, Na translocating, B subunit (nqrB) | IM | 1 | 91/21 | 1.32 | | 1 | 69/20 | 0.38 | | 1 | 3 (DB) |
| PG2124 | Glyceraldehyde 3-phosphate dehydrogenase | CY | 3 | 105/22 | 3.39 | 0.62 | 2 | 94/19 | 2.45 | | 3 | 2 (FE) |
| PG2157 | Glutamine cyclotransferase-related protein | PP/EX | 2 | 70/21 | 0.11 | | 3 | 53/20 | 0.45 | NA! | 3 | 2 (AB) |
| Ribosomal proteins | | | | | | | | | | | | |

TABLE 2-continued

List of the 81 proteins identified from both biological replicates of the *P. gingivalis* cell envelope fraction. An abundance ratio of >1 indicates a higher abundance of the protein in the biofilm with respect to the planktonic state. If the ratio differs from one with more than 3-fold SD (0.26) from the predetermined BSA ratios (>1.78 or <0.56), the proteins were considered to have significantly changed. Based on their mean ratios, proteins highlighted in grey represent significant changes.

| | | | | | | | | | | | | |
|---|---|---|---|---|---|---|---|---|---|---|---|---|
| PG0167 | Ribosomal protein L25 | CY | 4 | 57/20 | 0.27 | 0.05 | 2 | 50/21 | 0.30 | | 3 | 1 (AA) |
| PG0375 | Ribosomal protein L13 (rpIM) | CY | 2 | 69/21 | 0.28 | | 1 | 116/20 | 0.18 | | 2 | 1 (AA) |
| PG0392 | Ribosomal protein L10 (rpIJ) | CY | 2 | 97/21 | 0.33 | | 5 | 68/22 | 0.37 | 0.02 | 3 | 2 (AB) |
| PG0393 | Ribosomal protein L7/L12 | CY | 6 | 81/20 | 0.68 | 0.03 | 4 | 79/21 | 0.56 | 0.03 | 4 | 2 (CB) |
| Proteins with unkown functions | | | | | | | | | | | | |
| | integral outer membrane proteins | | | | | | | | | | | |
| PG0027 | Probable integral outer membrane protein P40 | OM | 11 | 143/21 | 0.74 | 0.06 | 23 | 111/20 | 0.81 | 0.02 | 11 | 1 (CC) |
| PG0613 | Possible outer membrane associated protein P23 | EX | 3 | 55/19 | 4.41 | 0.56 | 1 | 43/20 | 3.24 | | 2 | (1 FF) |
| PG0694 | Outer membrane protein 40 | OM | 37 | 116/20 | 3.62 | 0.37 | 77 | 86/20 | 3.39 | 0.24 | 13 | 1 (FF) |
| PG0695 | Outer membrane protein 41 | OM | 100 | 110/21 | 2.31 | 0.21 | 53 | 124/19 | 3.18 | 0.20 | 19 | 2 (EF) |
| PG1652 | Probable integral outer membrane protein P64 | OM | 2 | 53/20 | 1.04 | | 14 | 67/20 | 1.70 | 0.27 | 5 | 2 (CD) |
| PG1786 | Probable integral outer membrane protein P30 | EX/OM | 5 | 56/21 | 0.99 | 0.17 | 5 | 56/26 | 1.33 | 0.08 | 3 | 2 (CD) |
| PG1823 | Probable integral outer membrane protein P20 | PP/OM | 26 | 117/21 | 0.39 | 0.03 | 18 | 91/20 | 0.98 | 0.10 | 7 | 2 (BC) |
| PG2106 | Probable integral outer membrane protein P22 | IM/OM | 15 | 73/20 | 0.31 | 0.04 | 13 | 103/17 | 0.45 | 0.04 | 7 | 2 (AB) |
| | Lipoproteins | | | | | | | | | | | |
| PG0188 | Lipoprotein, putative | PP/EX | 7 | 72/23 | 0.92 | 0.09 | 4 | 40/20 | 1.18 | 0.11 | 5 | 2 (CD) |
| PG0241 | Lipoprotein, putative | OM/EX | 4 | 93/20 | 0.45 | 0.08 | 2 | 44/20 | 0.16 | | 3 | 2 (BA) |
| PG0906 | Lipoprotein, putative | PP/CY | 1 | 42/22 | 0.48 | | 5 | 97/20 | 0.40 | 0.05 | 3 | 1 (BB) |
| PG2173 | Outer membrane lipoprotein Omp28 | PP/OM | 8 | 109/22 | 0.77 | 0.1 | 12 | 89/18 | 0.71 | 0.04 | 7 | 1 (CC) |

TABLE 2-continued

List of the 81 proteins identified from both biological replicates of the *P. gingivalis* cell envelope fraction. An abundance ratio of >1 indicates a higher abundance of the protein in the biofilm with respect to the planktonic state. If the ratio differs from one with more than 3-fold SD (0.26) from the predetermined BSA ratios (>1.78 or <0.56), the proteins were considered to have significantly changed. Based on their mean ratios, proteins highlighted in grey represent significant changes.

| | Others proteins | | | | | | | | | | |
|---|---|---|---|---|---|---|---|---|---|---|---|
| PG0179 | Unnamed protein (conserved) | PP/EX | 1 | 64/22 | 1.23 | | 1 | 61/19 | 3.55 | | 1 | 3 (DF) |
| PG0181 | Immunoreactive 32 kDa antigen PG49 | PP/OM | 4 | 46/20 | 2.08 | 0.84 | 1 | 31/21 | 3.14 | | 3 | 2 (EF) |
| PG0217f | Unnamed protein | OM | 4 | 74/21 | 1.58 | 0.34 | 7 | 79/18 | 1.78 | 0.07 | 5 | 2 (DE) |
| PG0218 | Unnamed protein | OM | 4 | 61/20 | 2.10 | 0.55 | 11 | 55/20 | 1.59 | 0.17 | 4 | 2 (ED) |
| PG0287f | Unnamed protein | IM/OM | 3 | 77/21 | 1.32 | 0.06 | 7 | 53/20 | 1.90 | 0.21 | 5 | 2 (DE) |
| PG0409 | Unnamed protein (conserved) | PP | 4 | 82/22 | 2.20 | 0.38 | 2 | 69/19 | 2.28 | | 2 | 1 (EE) |
| PG0423 | Unnamed protein (conserved) | CY | 2 | 90/23 | 3.62 | | 1 | 72/21 | 0.68 | | 1 | 4 (FB) |
| PG0452 | Unnamed protein (conserved) | OM | 1 | 53/20 | 0.39 | | 3 | 81/20 | 0.40 | 0.11 | 2 | 1 (BB) |
| PG0448 | Unnamed protein (conserved) | OM | 11 | 74/22 | 1.05 | 0.11 | 10 | 58/20 | 1.44 | 0.08 | 7 | 1 (DD) |
| PG0449 | TPR domain protein | PP | 2 | 68/23 | 1.28 | | 1 | 64/18 | 1.19 | | 1 | 1 (DD) |
| PG0602 | Unnamed protein (conserved) | OM | 3 | 63/21 | 0.65 | 0.07 | 1 | 37/21 | NA** | | 2 | NA |
| PG0914 | Unnamed protein | OM | 1 | 66/21 | 2.23 | | 1 | 27/22 | 2.91 | | 2 | 2 (EF) |
| PG1028 | TPR domain protein | PP | 2 | 78/21 | 0.37 | | 5 | 70/19 | 0.48 | 0.08 | 4 | 1 (BB) |
| PG1035 | Unnamed protein (conserved) | OM | 1 | 42/21 | 0.31 | | 5 | 62/21 | 1.16 | 0.16 | 3 | 4 (AD) |
| PG1304 | Unnamed protein (conserved) | OM | 3 | 52/20 | 2.80 | 1.00 | 1 | 34/20 | 2.93 | | 1 | 2 (EF) |
| PG1356 | Unnamed protein (conserved) | CY | 2 | 60/21 | 0.31 | | 1 | 43/21 | 0.12 | | 2 | 1 (AA) |
| PG1382 | Unnamed protein (conserved) | OM | 3 | 63/21 | 1.89 | 0.29 | 1 | 51/21 | 4.43 | | 2 | 2 (EF) |
| PG1493 | Unnamed protein (conserved) | OM | 6 | 67/22 | 1.85 | 0.15 | 8 | 79/17 | 2.20 | 0.17 | 13 | 1 (EE) |
| PG1621 | Unnamed protein (conserved) | OM | 2 | 51/21 | 1.10 | | 4 | 60/21 | 0.42 | 0.05 | 2 | 2 (CB) |
| PG1684f | Unnamed protein | EX/IM | 1 | 58/22 | 1.25 | | 1 | 73/20 | 0.79 | | 1 | 2 (CD) |
| PG1715 | Unnamed protein (conserved) | OM | 4 | 51/20 | 1.10 | 0.04 | 13 | 71/20 | 0.97 | 0.14 | 3 | 2 (DC) |
| PG1881 | Unnamed protein (conserved) | OM | 2 | 49/22 | 0.61 | | 4 | 48/19 | 0.82 | 0.16 | 3 | 1 (CC) |
| PG1889f | Unnamed protein | CY | 12 | 99/20 | 0.16 | 0.02 | 8 | 85/20 | 0.25 | 0.03 | 6 | 1 (AA) |
| PG2049 | Unnamed protein | IM/CY | 3 | 48/21 | 0.63 | 0.06 | 1 | 27/21 | 0.82 | | 1 | 1 (CC) |
| PG2167 | Immunoreactive 52 kDa antigen PG123 | OM | 7 | 64/20 | 2.84 | 0.73 | 4 | 45/20 | 2.26 | 0.06 | 3 | 1 (EE) |
| PG2168 | Unnamed protein (conserved) | UN | 3 | 47/21 | 4.90 | 1.97 | 4 | 74/21 | 2.04 | 0.14 | 4 | 2 (FE) |
| PG2174 | Unnamed protein | OM | 5 | 58/21 | 0.78 | 0.06 | 15 | 102/21 | 0.37 | 0.04 | 7 | 2 (CB) | aLocations as determined by the CELLO program; EX: Extracellular, OM: Outer membrane, IM: Inner membrane, PP: Periplasm, CY: Cytoplasm; UN: unknown
bMaximum Mascot peptide ion score/identity threshold
cNormalized ratio; B = Biofilm, P= Planktonic, Normalization process as described in experimental procedures
dSE = Standard error of the mean
eRanking and grouping as described in FIG. 4B
fProteins identified only in this study
!SE measurements not carried out due to unresolved/overlapping of one of the 3 peptides
*Due to presence of identical peptides between these proteins, ratios derived were from peptides that were unique to these proteins only. Values in parenthesis are total number of peptides matched.
**Due to unresolved/overlapping peaks

TABLE 3

Proteomic and transcriptomic analyses of genes products involved in glutamate/aspartate catabolism in *P. gingivalis* during growth in heme-limitation compared to heme-excess. Shading indicates proteins that are predicted to be encoded in operons.

| No | Tigr Acc # | Protein and peptide sequence identified | Score[1] | N[2] | n-ICAT[3] | Proteomics Fold change[4] | SD (±) | Transcriptomics Fold change | Transcriptomics P-value |
|---|---|---|---|---|---|---|---|---|---|
| 1 | PG0329 | Formiminotransferase-cyclodeaminase-related protein<br>IMEC*VPNFSEGR (SEQ ID NO: 31) | 30/14 | 2 | 1 | 2.9 | — | NS[5] | |
| 2 | PG0548 | Pyruvate ferredoxin/flavodoxin oxidoreductase family protein<br>IAGELLPC *VFHVSAR (SEQ ID NO: 32) | 33/15 | 1 | 1 | 2.0 | — | NS | |
| 3 | PG0687 | Succinate-semialdehyde dehydrogenase<br>AFDNGIIC*SGEQSIIYNEADK (SEQ ID NO: 33)<br>C*SAHAVR (SEQ ID NO: 34)<br>EYQATHNQEAVDNIC*R (SEQ ID NO: 35)<br>GVGAEDVIC*K (SEQ ID NO: 36)<br>NHGAYFC*DEAEGDR (SEQ ID NO: 37)<br>TC*NAIIIAPHPR (SEQ ID NO: 38) | 37/18<br>22/16<br>18/13<br>43/13<br>53/14<br>66/13 | 27 | 6 | 4.0 | 1.6 | 1.77 | 0.066 |
| 4 | PG0689 | NAD-dependent 4-hydroxybutyrate dehydrogenase<br>ELIIVPTTC*GTGSEVTNISIAEIK (SEQ ID NO: 39)<br>ILNC*QPEYVYPK (SEQ ID NO: 40)<br>LDELLGC*LLTK (SEQ ID NO: 41) | 35/19<br>41/18<br>35/14 | 12 | 3 | 2.8 | 0.8 | 1.93 | 8.892E-05 |
| 5 | PG0690[6] | 4-hydroxybutyrate-CoA transferase | | | | | | 3.31 | 0.03 |
| 6 | PG0691[6] | NifU-like protein | | | | | | 1.60 | 0.0002 |
| 7 | PG0692 | 4-hydroxybutyryl-CoA dehydratase<br>AGNYMIDLLLANVC*K (SEQ ID NO: 42)<br>TASC*FQR (SEQ ID NO: 43) | 42/15<br>20/15 | 5 | 2 | 2.9 | 0.7 | 1.65 | 0.054 |
| 8 | PG1067 | Hypothetical protein<br>TDISESAADVLVEPIVVC*R (SEQ ID NO: 44) | 64/14 | 2 | 1 | 2.4 | — | NS | |
| 9 | PG1068 | Conserved hypothetical protein<br>MIITAAIC*GAEVLK (SEQ ID NO: 45)<br>AVC*PDVIIQPSTGGAVGMTNDER (SEQ ID NO: 46) | 40/12<br>38/15 | 3 | 2 | 1.7 | 0.1 | NS | |
| 10 | PG1075[6] | Butyrate-acetoacetate CoA transferase | | | | | | 1.4 | 0.05 |
| 11 | PG1076 | Acyl-CoA dehydrogenase, short-chain specific<br>LYC*AETAMDMTTK (SEQ ID NO: 47)<br>SIAQFQNTQFQLADLQC*R (SEQ ID NO: 48) | 26/14<br>23/19 | 3 | 2 | 1.8 | 0.2 | NS | |
| 12 | PG1078 | Electron transfer flavoprotein, alpha subunit<br>VTAILC*GYK (SEQ ID NO: 49)<br>TGLTADC*TSLEIGDER (SEQ ID NO: 50) | 22/15<br>55/15 | 5 | 2 | 2.0 | 0.4 | NS | |
| 13 | PG1079[6] | Enoyl-CoA | | | | | | 1.3 | 0.04 |
| 14 | PG1081 | Acetate kinase<br>VLVLNC*GSSSVK (SEQ ID NO: 51)<br>AC*EILGLDYDK (SEQ ID NO: 52)<br>VEEC*IPLAPLHNPANLK (SEQ ID NO: 53) | 42/14<br>29/15<br>42/14 | 9 | 3 | 3.5 | 0.9 | NS | |
| 15 | PG1082 | Phosphototransacetylase<br>AAELVENPLYLGC*LIVK (SEQ ID NO: 54)<br>GC*SVEDIYR (SEQ ID NO: 55) | 52/15<br>45/15 | 5 | 2 | 4.4 | 1.6 | NS | |

TABLE 3-continued

Proteomic and transcriptomic analyses of genes products involved in glutamate/aspartate catabolism in *P. gingivalis* during growth in heme-limitation compared to heme-excess. Shading indicates proteins that are predicted to be encoded in operons.

| | | | | | | | | | |
|---|---|---|---|---|---|---|---|---|---|
| 16 | PG1232 | Glutamate dehydrogenase, NAD-specific C*MLDLR (SEQ ID NO: 56) LRPESTGFGAVYFVQNMC* K (SEQ ID NO: 57) | 28/14 54/15 | 10 | 2 | 2.3 | 1.2 | NS | |
| 17 | PG1271 | Ornithine aminotransferase AVIIVC*DGNFHGR (SEQ ID NO: 58) YFDFLSAYSAVNQGHC*HPK (SEQ ID NO: 59) | 42/19 3219 | 3 | 2 | 0.09 | — | NS | |
| 18 | PG1417 | Fumarate hydratase class I, anaerobic GQLPFC*QDTGTAIILGK (SEQ ID NO: 60) HGASC*PVGMGVSC*SADR (SEQ ID NO: 61) | 57/15 18/16 | 3 | 2 | 1.0 | 0.2 | NS | |
| 19 | PG1612 | Methylmalonyl-CoA decarboxylase, alpha subunit FNGQSVGIVANQPQVMAGC*LDSNASR (SEQ ID NO: 62) C*TNFGIDK (SEQ ID NO: 63) | 28/14 21/15 | 2 | 2 | 2.4 | — | NS | |
| 20 | PG1614 | Fumarate reductase, flavoprotein subunit (FrdB) MDELGFGNC*TNTR (SEQ ID NO: 64) APVVFDHDC*R (SEQ ID NO: 65) | 45/15 36/13 | 6 | 2 | 0.25 | 0.1 | NS | |
| 21 | PG1615 | Fumarate reductase, flavoprotein subunit (FrdA) LAEVSNAIIDQC*VAQGVPFAR (SEQ ID NO: 66) | 29/14 | 1 | 1 | 0.35 | — | NS | |
| 22 | PG1741 | Aspartate ammonia-lyase C*GLHEFNLPAMQPRSSIMPGK (SEQ ID NO: 67) VNPVIPEVMNQIC*YK (SEQ ID NO: 68) | 24/14 20/15 | 4 | 2 | 1.0 | 0.2 | NS | |
| 23 | PG1810 | 2-oxoglutarate oxidoreductase, beta subunit IADMLALLDGTC*LVTR (SEQ ID NO: 69) | 54/16 | 3 | 1 | 2.5 | 0.5 | NS | |
| 24 | PG1949 | Malate dehydrogenase LTPNLC*LYDPFAVGLEGVAEEIR (SEQ ID NO: 70) | 35/15 | 3 | 1 | 1.0 | 0.2 | NS | |

[1] Highest scoring peptide score/threshold score (P = 0.05)
[2] Total number of independent peptide identification events for each protein
[3] Number of unique ICAT-labelled peptides identified for each protein
[4] Average ratios of all quantified peptides for each protein in fold change (Heme-limitation/excess)
[5] NS no statistically significant change detected
[6] Only identified in microarray analysis
C* Denotes ICAT-modified cysteine

TABLE 4

The 24 *P. gingivalis* polypeptides selected as targets for inhibition of biofilm formation.

| Tigr # | Protein | Predicted location | Ratio (B/P) Biol. Rep 1 | Ratio (B/P) Biol. Rep 2 | Rank (Group) | Accession Number* | Accession Number Version |
|---|---|---|---|---|---|---|---|
| | CTD family proteins | | | | | | |
| PG0232 | Zinc carboxypeptidase, CPG70 | OM | 1.67 | 2.53 | 3 (DF) | AAQ65462 | AAQ65462.1 |
| PG0553 | Extracellular protease, lysyl endopeptidase precursor (API) | OM/EX | 3.33 | 3.45 | 1 (FF) | AAQ65742 | AAQ65742.1 |
| PG2024 | Arginine-specific protease ArgI polyprotein (RgpA) Haem binding | OM | 1.63 | 3.78 | 3 (DE) | AAQ66991 | AAQ66991.1 |
| PG0616 | Thioredoxin, putative Biofilm related | PP/CY | 2.23 | 3.69 | 2 (EF) | AAQ65800 | AAQ65800.1 |
| PG0350 | Internalin-related protein Adhesins | OM/EX | 1.99 | 4.27 | 2 (EF) | AAQ65561 | AAQ65561.1 |
| PG1837 | Hemagglutinin protein HagA Protein with unknown functions | OM | 2.73 | 4.21 | 1 (FF) | AAQ66831 | AAQ66831.1 |
| PG1798 | Immunoreactive 46 kDa antigen PG99 | PP/EX | 5.94 | 4.07 | 1 (FF) | AAQ66797 | AAQ66797.1 |

TABLE 4-continued

The 24 *P. gingivalis* polypeptides selected as targets for inhibition of biofilm formation.

| Tigr # | Protein | Predicted location | Ratio (B/P) Biol. Rep 1 | Ratio (B/P) Biol. Rep 2 | Rank (Group) | Accession Number* | Accession Number Version |
|---|---|---|---|---|---|---|---|
| | Transport | | | | | | |
| PG1414 | TonB linked outer membrane receptor, PG47 | OM | 3.81 | 3.69 | 1 (FF) | AAQ66469 | AAQ66469.1 |
| PG1551 | HmuY protein | OM | 2.57 | 2.78 | 1 (DD) | AAQ66587 | AAQ66587.1 |
| PG1626 | Possible outer membrane-associated protein P58 (putative haem receptor protein) | OM | 2.37 | 3.68 | 2 (EF) | AAQ66654 | AAQ66654.1 |
| PG2008 | TonB-dependent receptor, P90 | OM | 2.08 | 3.12 | 2 (EF) | AAQ66977 | AAQ66977.1 |
| | Proteins with unknown functions | | | | | | |
| | Integral outer membrane proteins | | | | | | |
| PG0613 | Possible outer membrane associated protein P23 | EX | 4.41 | 3.24 | 1 (FF) | AAQ65797 | AAQ65797.1 |
| PG0694 | Outer membrane protein 40 | OM | 3.62 | 3.39 | 1 (FF) | AAQ65867 | AAQ65867.1 |
| PG0695 | Outer membrane protein 41 | OM | 2.31 | 3.18 | 2 (EF) | AAQ65868 | AAQ65868.1 |
| | Others proteins | | | | | | |
| PG0181 | Immunoreactive 32 kDa antigen PG49 | PP/OM | 2.08 | 3.14 | 2 (EF) | AAQ65416 | AAQ65416.1 |
| PG0218 | Unnamed protein | OM | 2.10 | 1.59 | 2 (ED) | AAQ65449 | AAQ65449.1 |
| PG0914 | Unnamed protein | OM | 2.23 | 2.91 | 2 (EF) | AAQ66051 | AAQ66051.1 |
| PG1304 | Unnamed protein (conserved) | OM | 2.80 | 2.93 | 2 (EF) | AAQ66377 | AAQ66377.1 |
| PG1382 | Unnamed protein (conserved) | OM | 1.89 | 4.43 | 2 (EF) | AAQ66444 | AAQ66444.1 |
| PG1493 | Unnamed protein (conserved) | OM | 1.85 | 2.20 | 1 (EE) | AAQ66538 | AAQ66538.1 |
| PG2167 | Immunoreactive 53 kDa antigen PG123 | OM | 2.84 | 2.26 | 1 (EE) | AAQ67117 | AAQ67117.1 |
| PG2168 | Unnamed protein (conserved) | UN | 4.90 | 2.04 | 2 (FE) | AAQ67118 | AAQ67118.1 |
| | Energy Metabolism | | | | | | |
| PG1614 | Fumarate reductase, iron-sulfur protein (frdB) | UN | 0.15 | 0.19 | 1 (AA) | AAQ66642 | AAQ66642.1 |
| PG1615 | Fumarate reductase, flavoprotein subunit (frdA) | UN | 0.06 | — | NA | AAQ66643 | AAQ66643.1 |

*These accession numbers provide a sequence for the *P. gingivalis* proteins referred to in the specification. Sequences corresponding to the accession numbers are incorporated by reference.

TABLE 5

Proteomic and transcriptomic analyses of *P. gingivalis* grown in heme-limitation compared to heme-excess.
Shading indicates proteins that are predicted to be encoded in operons.

| No | Tigr Acc # | Protein and peptide sequence identified | Score[1] | N[2] | n-ICAT[3] | Proteomics Fold change[4] | SD (±) | Transcriptomics Fold change | Transcriptomics P-value |
|---|---|---|---|---|---|---|---|---|---|
| Iron transport and related proteins | | | | | | | | | |
| 13 | PG0644[6] | HtrE (Tla) TonB-linked receptor | | | | | | 2.05 | 1.54E-04 |
| 18 | PG1552 | HmuR MSNDELFEEITYPGYTIC*R (SEQ ID NO: 71) | 25/15 | 1 | 1 | 4.0 | — | 3.13 | 0.003 |
| 21 | PG1019 | Hypothetical protein TYMIDTNDSENDC*IAR (SEQ ID NO: 19) | 70/14 | 2 | 1 | 25.0 | — | 2.57 | 0.003 |
| 22 | PG1020[6] | Conserved hypothetical protein; possible outer membrane receptor protein | | | | | | 3.36 | 3.0E-04 |
| Others | | | | | | | | | |
| 33 | PG1874[6] | Conserved hypothetical protein | | | | | | 1.52 | 0.05 |
| 34 | PG1875[6] | Hemolysin A | | | | | | 1.40 | 0.05 |

[1] Highest scoring peptide score/threshold score (P = 0.05)

[2] Total number of independent peptide identification events for each protein

[3] Number of unique ICAT-labelled peptides identified for each protein

[4] Average ratios of all quantified peptides for each protein in fold change (Heme-limitation/excess)

[5] NS no statistically significant change detected

[6] Only identified in microarray analysis

C* Denotes ICAT-modified cysteine

REFERENCES

1. Costerton, J. W., Lewandowski, Z., Caldwell, D. E., Korber, D. R., and Lappin-Scott, H. M. (1995) *Annu. Rev. Microbiol.* 49, 711-745
2. Cvitkovitch, D. G., Li, Y. H., and Ellen, R. P. (2003) *J. Clin. Invest.* 112(11), 1626-1632
3. Cochrane, D. M., Brown, M. R., Anwar, H., Weller, P. H., Lam, K., and Costerton, J. W. (1988) *J. Med. Microbiol.* 27(4), 255-261
4. van Steenbergen, T. J., Kastelein, P., Touw, J. J., and de Graaff, J. (1982) *J. Periodontal Res.* 17(1), 41-49
5. Neiders, M. E., Chen, P. B., Suido, H., Reynolds, H. S., Zambon, J. J., Shlossman, M., and Genco, R. J. (1989) *J. Periodontal Res.* 24(3), 192-198
6. Griffen, A. L., Becker, M. R., Lyons, S. R., Moeschberger, M. L., and Leys, E. J. (1998) *J. Clin. Microbiol.* 36(11), 3239-3242
7. Cutler, C. W., Arnold, R. R., and Schenkein, H. A. (1993) *J. Immunol.* 151(12), 7016-7029
8. Chen, T., Hosogi, Y., Nishikawa, K., Abbey, K., Fleischmann, R. D., Walling, J., and Duncan, M. J. (2004) *J. Bacteriol.* 186(16), 5473-5479
9. Davey, M. E. (2006) *Periodontol. 2000* 42, 27-35
10. Orme, R., Douglas, C. W., Rimmer, S., and Webb, M. (2006) *Proteomics* 6(15), 4269-4277
11. Rathsam, C., Eaton, R. E., Simpson, C. L., Browne, G. V., Valova, V. A., Harty, D. W., and Jacques, N. A. (2005) *J Proteome Res* 4(6), 2161-2173
12. Sauer, K., Camper, A. K., Ehrlich, G. D., Costerton, J. W., and Davies, D. G. (2002) *J. Bacteriol.* 184(4), 1140-1154
13. Ong, S. E., and Mann, M. (2005) *Nat. Chem. Biol.* 1(5), 252-262
14. Bender, M. L., and Kemp, K. C. (1957) *J. Am. Chem. Soc* 79, 116
15. Schnolzer, M., Jedrzejewski, P., and Lehmann, W. D. (1996) *Electrophoresis* 17(5), 945-953
16. Yao, X., Freas, A., Ramirez, J., Demirev, P. A., and Fenselau, C. (2001) *Anal Chem* 73(13), 2836-2842
17. Blonder, J., Hale, M. L., Chan, K. C., Yu, L. R., Lucas, D. A., Conrads, T. P., Zhou, M., Popoff, M. R., Issaq, H. J., Stiles, B. G., and Veenstra, T. D. (2005) *J. Proteome Res* 4(2), 523-531
18. Qian, W. J., Monroe, M. E., Liu, T., Jacobs, J. M., Anderson, G. A., Shen, Y., Moore, R. J., Anderson, D. J., Zhang, R., Calvano, S. E., Lowry, S. F., Xiao, W., Moldawer, L. L., Davis, R. W., Tompkins, R. G., Camp, D. G., 2nd, and Smith, R. D. (2005) *Mol. Cell Proteomics* 4(5), 700-709
19. Zang, L., Palmer Toy, D., Hancock, W. S., Sgroi, D. C., and Karger, B. L. (2004) *J. Proteome Res.* 3(3), 604-612
20. Kuster, B., and Mann, M. (1999) *Anal. Chem.* 71(7), 1431-1440
21. Takao, T., Hori, H., Okamoto, K., Harada, A., Kamachi, M., and Shimonishi, Y. (1991) *Rapid Commun. Mass Spectrom.* 5(7), 312-315
22. Shevchenko, A., Chernushevich, I., Ens, W., Standing, K. G., Thomson, B., Wilm, M., and Mann, M. (1997) *Rapid Commun. Mass Spectrom.* 11(9), 1015-1024
23. Gevaert, K., Staes, A., Van Damme, J., De Groot, S., Hugelier, K., Demol, H., Martens, L., Goethals, M., and Vandekerckhove, J. (2005) *Proteomics* 5(14), 3589-3599
24. Chen, X., Cushman, S. W., Pannell, L. K., and Hess, S. (2005) *J. Proteome Res.* 4(2), 570-577
25. Stockwin, L. H., Blonder, J., Bumke, M. A., Lucas, D. A., Chan, K. C., Conrads, T. P., Issaq, H. J., Veenstra, T. D., Newton, D. L., and Rybak, S. M. (2006) *J. Proteome Res.* 5(11), 2996-3007
26. Lane, C. S., Wang, Y., Betts, R., Griffiths, W. J., and Patterson, L. H. (2007) *Mol. Cell Proteomics*
27. Korbel, S., Schumann, M., Bittorf, T., and Krause, E. (2005) *Rapid Comm. Mass Spectrom.* 19(16), 2259-2271
28. Bantscheff, M., Dumpelfeld, B., and Kuster, B. (2004) *Rapid Commun. Mass. Spectrom.* 18(8), 869-876
29. Jia, J. Y., Lamer, S., Schumann, M., Schmidt, M. R., Krause, E., and Haucke, V. (2006) *Mol. Cell. Proteomics* 5(11), 2060-2071
30. Miyagi, M., and Rao, K. C. (2007) *Mass Spectrom. Rev* 26(1), 121-136
31. Veith, P. D., Talbo, G. H., Slakeski, N., Dashper, S. G., Moore, C., Paolini, R. A., and Reynolds, E. C. (2002) *Biochem. J.* 363(Pt 1), 105-115
32. Qian, W. J., Liu, T., Monroe, M. E., Strittmatter, E. F., Jacobs, J. M., Kangas, L. J., Petritis, K., Camp, D. G., 2nd, and Smith, R. D. (2005) *J. Proteome Res* 4(1), 53-62
33. Perkins, D. N., Pappin, D. J., Creasy, D. M., and Cottrell, J. S. (1999) *Electrophoresis* 20(18), 3551-3567
34. Xia, Q., Hendrickson, E. L., Zhang, Y., Wang, T., Taub, F., Moore, B. C., Porat, I., Whitman, W. B., Hackett, M., and Leigh, J. A. (2006) *Mol. Cell. Proteomics* 5(5), 868-881
35. Quackenbush, J. (2001) *Nat. Rev. Genet.* 2(6), 418-427
36. Yu, C. S., Chen, Y. C., Lu, C. H., and Hwang, J. K. (2006) *Proteins* 64(3), 643-651
37. Richardson, A. J., Calder, A. G., and Stewart, C. S. (1989) *Letters in Applied Microbiology* 9, 5-8
38. O'Toole, G. A., and Kolter, R. (1998) *Mol Microbiol* 28(3), 449-461
39. Capestany, C. A., Kuboniwa, M., Jung, I. Y., Park, Y., Tribble, G. D., and Lamont, R. J. (2006) *Infect. Immun.* 74(5), 3002-3005
40. Lopez-Ferrer, D., Ramos-Fernandez, A., Martinez-Bartolome, S., Garcia-Ruiz, P., and Vazquez, J. (2006) *Proteomics* 6 Suppl 1, S4-S11
41. Staes, A., Demol, H., Van Damme, J., Martens, L., Vandekerckhove, J., and Gevaert, K. (2004) *J Proteome Res* 3(4), 786-791
42. Patwardhan, A. J., Strittmatter, E. F., Camp, D. G., 2nd, Smith, R. D., and Pallavicini, M. G. (2006) *Proteomics* 6(9), 2903-2915
43. Smalley, J. W., Birss, A. J., McKee, A. S., and Marsh, P. D. (1993) *J Gen Microbiol* 139(9), 2145-2150
44. McKee, A. S., McDermid, A. S., Baskerville, A., Dowsett, A. B., Ellwood, D. C., and Marsh, P. D. (1986) *Infect. Immun.* 52(2), 349-355
45. Dashper, S. G., Butler, C. A., Lissel, J. P., Paolini, R. A., Hoffmann, B., Veith, P. D., O'Brien-Simpson, N. M., Snelgrove, S. L., Tsiros, J. T., and Reynolds, E. C. (2005) *J. Biol. Chem.* 280(30), 28095-28102
46. Li, J., Steen, H., and Gygi, S. P. (2003) *Mol. Cell. Proteomics* 2(11), 1198-1204
47. Dashper, S. G., Brownfield, L., Slakeski, N., Zilm, P. S., Rogers, A. H., and Reynolds, E. C. (2001) *J. Bacteriol.* 183(14), 4142-4148
48. Hoskisson, P. A., and Hobbs, G. (2005) *Microbiology* 151(Pt 10), 3153-3159
49. Piper, M. D., Daran-Lapujade, P., Bro, C., Regenberg, B., Knudsen, S., Nielsen, J., and Pronk, J. T. (2002) *J. Biol. Chem.* 277(40), 37001-37008
50. Siroy, A., Cosette, P., Seyer, D., Lemaitre-Guillier, C., Vallenet, D., Van Dorsselaer, A., Boyer-Mariotte, S., Jouenne, T., and De, E. (2006) *J. Proteome Res.* 5(12), 3385-3398

51. Hood, B. L., Lucas, D. A., Kim, G., Chan, K. C., Blonder, J., Issaq, H. J., Veenstra, T. D., Conrads, T. P., Pollet, I., and Karsan, A. (2005) *J Am Soc Mass Spectrom* 16(8), 1221-1230
52. Yao, X., Afonso, C., and Fenselau, C. (2003) *J Proteome Res* 2(2), 147-152
53. Eckel-Passow, J. E., Oberg, A. L., Therneau, T. M., Mason, C. J., Mahoney, D. W., Johnson, K. L., Olson, J. E., and Bergen, H. R., 3rd. (2006) *Bioinformatics* 22(22), 2739-2745
54. Storms, H. F., van der Heijden, R., Tjaden, U. R., and van der Greef, J. (2006) *Rapid Commun. Mass Spectrom.* 20(23), 3491-3497
55. Zenobi, R., and Knochenmuss, R. (1998) *Mass Spectrom. Rev.* 17(5), 337-366
56. Seers, C. A., Slakeski, N., Veith, P. D., Nikolof, T., Chen, Y. Y., Dashper, S. G., and Reynolds, E. C. (2006) *J. Bacteriol.* 188(17), 6376-6386
57. Curtis, M. A., Kuramitsu, H. K., Lantz, M., Macrina, F. L., Nakayama, K., Potempa, J., Reynolds, E. C., and Aduse-Opoku, J. (1999) *J. Periodontal Res.* 34(8), 464-472
58. O'Brien-Simpson, N. M., Paolini, R. A., Hoffmann, B., Slakeski, N., Dashper, S. G., and Reynolds, E. C. (2001) *Infect. Immun.* 69(12), 7527-7534
59. O'Brien-Simpson, N. M., Veith, P. D., Dashper, S. G., and Reynolds, E. C. (2003) *Curr. Protein Pept. Sci.* 4(6), 409-426
60. Abe, N., Kadowaki, T., Okamoto, K., Nakayama, K., Ohishi, M., and Yamamoto, K. (1998) *J. Biochem.* (Tokyo) 123(2), 305-312
61. Potempa, J., Pike, R., and Travis, J. (1995) *Infect. Immun.* 63(4), 1176-1182
62. Pathirana, R. D., O'Brien-Simpson, N. M., Brammar, G. C., Slakeski, N., and Reynolds, E. C. (2007) *Infect. Immun.* 75(3), 1436-1442
63. Chen, Y. Y., Cross, K. J., Paolini, R. A., Fielding, J. E., Slakeski, N., and Reynolds, E. C. (2002) *J. Biol. Chem.* 277(26), 23433-23440
64. Zhang, Y., Wang, T., Chen, W., Yilmaz, O., Park, Y., Jung, I. Y., Hackett, M., and Lamont, R. J. (2005) *Proteomics* 5(1), 198-211
65. Sato, K., Sakai, E., Veith, P. D., Shoji, M., Kikuchi, Y., Yukitake, H., Ohara, N., Naito, M., Okamoto, K., Reynolds, E. C., and Nakayama, K. (2005) *J. Biol. Chem.* 280(10), 8668-8677
66. Nguyen, K. A., Travis, J., and Potempa, J. (2007) *J. Bacteriol.* 189(3), 833-843
67. Dashper, S. G., Cross, K. J., Slakeski, N., Lissel, P., Aulakh, P., Moore, C., and Reynolds, E. C. (2004) *Oral Microbiol. Immunol.* 19(1), 50-56
68. Lewis, J. P., Dawson, J. A., Hannis, J. C., Muddiman, D., and Macrina, F. L. (1999) J. Bacteriol. 181(16), 4905-4913
69. Shi, Y., Ratnayake, D. B., Okamoto, K., Abe, N., Yamamoto, K., and Nakayama, K. (1999) *J. Biol. Chem.* 274 (25), 17955-17960
70. Sroka, A., Sztukowska, M., Potempa, J., Travis, J., and Genco, C. A. (2001) *J. Bacteriol.* 183(19), 5609-5616
71. Simpson, W., Olczak, T., and Genco, C. A. (2000) *J Bacteriol* 182(20), 5737-5748
72. Lewis, J. P., Plata, K., Yu, F., Rosato, A., and Anaya, C. (2006) *Microbiology* 152(Pt 11), 3367-3382
73. Olczak, T., Siudeja, K., and Olczak, M. (2006) *Protein Expr. Purif.* 49(2), 299-306
74. Olczak, T., Simpson, W., Liu, X., and Genco, C. A. (2005) *FEMS Microbiol. Rev.* 29(1), 119-144
75. Veith, P. D., Chen, Y. Y., and Reynolds, E. C. (2004) *Infect. Immun.* 72(6), 3655-3657
76. Shibata, Y., Hiratsuka, K., Hayakawa, M., Shiroza, T., Takiguchi, H., Nagatsuka, Y., and Abiko, Y. (2003) *Biochem. Biophys. Res. Commun.* 300(2), 351-356
77. Tatusov, R. L., Fedorova, N. D., Jackson, J. D., Jacobs, A. R., Kiryutin, B., Koonin, E. V., Krylov, D. M., Mazumder, R., Mekhedov, S. L., Nikolskaya, A. N., Rao, B. S., Smirnov, S., Sverdlov, A. V., Vasudevan, S., Wolf, Y. I., Yin, J. J., and Natale, D. A. (2003) *BMC Bioinformatics* 4, 41
78. Ratnayake, D. B., Wai, S, N., Shi, Y., Amako, K., Nakayama, H., and Nakayama, K. (2000) *Microbiology* 146 1119-1127
79. Smalley, J. W., Birss, A. J., McKee, A. S., and Marsh, P. D. (1991) *FEMS Microbiol. Lett.* 69(1), 63-67
80. Dashper, S. G., Hendtlass, A., Slakeski, N., Jackson, C., Cross, K. J., Brownfield, L., Hamilton, R., Barr, I., and Reynolds, E. C. (2000) *J Bacteriol* 182(22), 6456-6462
81. Takahashi, N., Sato, T., and Yamada, T. (2000) *J. Bacteriol.* 182(17), 4704-4710
82. Takahashi, N., and Sato, T. (2001) *J Dent Res* 80(5), 1425-1429
83. Litwin, C. M., and Calderwood, S. B. (1993) *Clin Microbiol Rev* 6(2), 137-149
84. Gygi, S. P., Rochon, Y., Franza, B. R., and Aebersold, R. (1999) *Mol. Cell. Biol.* 19(3), 1720-1730
85. Baughn, A. D., and Malamy, M. H. (2003) *Microbiology* 149(Pt 6), 1551-1558
86. Macy, J., Probst, I., and Gottschalk, G. (1975) *J Bacteriol* 123(2), 436-442
87. Baughn, A. D., and Malamy, M. H. (2002) *Proc Natl Acad Sci USA* 99(7), 4662-4667
88. Mayrand, D., and McBride, B. C. (1980) *Infect Immun* 27(1), 44-50
89. Smith, M. A., Mendz, G. L., Jorgensen, M. A., and Hazell, S. L. (1999) *Int J Biochem Cell Biol* 31(9), 961-975
90. Kroger, A., Geisler, V., Lemma, E., Theis, F., and Lenger, R. (1992) *Archives of Microbiology* 158(5), 311-314
91. Shah, H., and Williams, R. (1987) *Current Microbiology* 15, 241-246
92. Klein, R. A., Linstead, D. J., and Wheeler, M. V. (1975) *Parasitology* 71(1), 93-107
93. Turrens, J. F. (1989) *Biochem J* 259(2), 363-368
94. Mendz, G. L., Hazell, S. L., and Srinivasan, S. (1995) *Arch Biochem Biophys* 321(1), 153-159
95. Mendz, G. L., Meek, D. J., and Hazell, S. L. (1998) *J Membr Biol* 165(1), 65-76
96. Mileni, M., MacMillan, F., Tziatzios, C., Zwicker, K., Haas, A. H., Mantele, W., Simon, J., and Lancaster, C. R. (2006) *Biochem J* 395(1), 191-201
97. Nealson, K., and D, S. (1994) *Annual review of microbiology* 48, 311-343
98. Sellars, M. J., Hall, S. J., and Kelly, D. J. (2002) *J Bacteriol* 184(15), 4187-4196
99. O'Toole, G. A., Gibbs, K. A., Hager, P. W., Phibbs, P. V., Jr., and Kolter, R. (2000) *J Bacteriol* 182(2), 425-431
100. Whiteley, M., Bangera, M. G., Bumgarner, R. E., Parsek, M. R., Teitzel, G. M., Lory, S., and Greenberg, E. P. (2001) *Nature* 413(6858), 860-864
101. Romeo, T., Gong, M., Liu, M. Y., and Brun-Zinkernagel, A. M. (1993) *J Bacteriol* 175(15), 4744-4755
102. Sabnis, N. A., Yang, H., and Romeo, T. (1995) *J Biol Chem* 270(49), 29096-29104
103. Mercante, J., Suzuki, K., Cheng, X., Babitzke, P., and Romeo, T. (2006) *J Biol Chem* 281(42), 31832-31842
104. Altier, C., Suyemoto, M., and Lawhon, S. D. (2000) *Infect Immun* 68(12), 6790-6797

105. Lawhon, S. D., Frye, J. G., Suyemoto, M., Porwollik, S., McClelland, M., and Altier, C. (2003) *Mol Microbiol* 48(6), 1633-1645
106. Hefford, M. A., D'Aoust, S., Cyr, T. D., Austin, J. W., Sanders, G., Kheradpir, E., and Kalmokoff, M. L. (2005) *Can. J. Microbiol.* 51(3), 197-208
107. Pancholi, V., and Fischetti, V. A. (1992) *J. Exp. Med.* 176(2), 415-426
108. Taylor, J. M., and Heinrichs, D. E. (2002) *Mol. Microbiol.* 43(6), 1603-1614
109. Maeda, K., Nagata, H., Yamamoto, Y., Tanaka, M., Tanaka, J., Minamino, N., and Shizukuishi, S. (2004) *Infect. Immun.* 72(3), 1341-1348
110. Gustaysson, N., Diez, A., and Nystrom, T. (2002) *Mol. Microbiol.* 43(1), 107-117
111. Kvint, K., Nachin, L., Diez, A., and Nystrom, T. (2003) *Curr. Opin. Microbiol.* 6(2), 140-145
112. Kuramitsu, H. K., Chen, W., and Ikegami, A. (2005) *J. Periodontol.* 76(11 Suppl), 2047-2051

---

The invention claimed is:

1. A method of inhibiting or treating *P. gingivalis* infection and/or periodontal disease in a subject suffering from *P. gingivalis* infection and/or periodontal disease, comprising administering to the subject by oral or nasal administration or by injection an effective amount of a composition comprising a polypeptide selected from the group consisting of polypeptides having the amino acid sequence of SEQ ID NO: 72 (accession number AAQ66654) and variants of SEQ ID NO: 72 consisting of conservative substitutions to SEQ ID NO: 72, wherein the variants are at least 90% identical to SEQ ID NO: 72, and induce the production of an antibody that specifically binds to the polypeptide of SEQ ID NO: 72.

2. The method of claim 1, wherein the composition further comprises an adjuvant and/or a pharmaceutically acceptable carrier.

3. The method of claim 1, wherein the polypeptide has the amino acid sequence of SEQ ID NO:72 (accession number AAQ66654).

4. The method of claim 1, wherein the polypeptide is selected from said variants that are at least 95% identical to SEQ ID NO: 72.

* * * * *